US010271552B2

(12) United States Patent
Schwarz et al.

(10) Patent No.: US 10,271,552 B2
(45) Date of Patent: Apr. 30, 2019

(54) HETEROCYCLIC COMPOUNDS AS PESTICIDES

(71) Applicant: Bayer CropScience Aktiengesellschaft, Monheim am Rhein (DE)

(72) Inventors: Hans-Georg Schwarz, Dorsten (DE); Anne Decor, Langenfeld (DE); Joerg Greul, Leverkusen (DE); Axel Trautwein, Duesseldorf (DE); Eike Kevin Heilmann, Duesseldorf (DE); Reiner Fischer, Monheim (DE); Peter Loesel, Leverkusen (DE); Olga Malsam, Roesrath (DE); Daniela Portz, Vettweiss (DE); Kerstin Ilg, Cologne (DE); Herbert Sommer, Leichlingen (DE); Sascha Eilmus, Leichlingen (DE); Melanie Scharwey, Leichlingen (DE); Anton Lishchynskyi, Duesseldorf (DE); Sven Geibel, Velbert (DE); Ulrich Goergens, Ratingen (DE); Simon Anthony Herbert, Berlin (DE); Andreas Turberg, Haan (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/741,758

(22) PCT Filed: Jul. 5, 2016

(86) PCT No.: PCT/EP2016/065766
§ 371 (c)(1),
(2) Date: Jan. 3, 2018

(87) PCT Pub. No.: WO2017/005717
PCT Pub. Date: Jan. 12, 2017

(65) Prior Publication Data
US 2018/0213782 A1 Aug. 2, 2018

(30) Foreign Application Priority Data
Jul. 6, 2015 (EP) .................................... 15175382

(51) Int. Cl.
| | |
|---|---|
| C07D 285/08 | (2006.01) |
| C07D 417/04 | (2006.01) |
| C07D 417/12 | (2006.01) |
| C07D 417/14 | (2006.01) |
| A01N 43/82 | (2006.01) |

(52) U.S. Cl.
CPC ........... *A01N 43/82* (2013.01); *C07D 285/08* (2013.01); *C07D 417/04* (2013.01); *C07D 417/12* (2013.01); *C07D 417/14* (2013.01)

(58) Field of Classification Search
CPC .. C07D 285/08; C07D 417/04; C07D 417/12; C07D 417/14
See application file for complete search history.

(56) References Cited

FOREIGN PATENT DOCUMENTS

| | | |
|---|---|---|
| EP | 0455356 A1 | 11/1991 |
| EP | 1254135 A2 | 8/2014 |
| WO | 0140223 A2 | 6/2001 |
| WO | 2015073797 A1 | 5/2015 |
| WO | 2016/071499 A1 | 5/2016 |

OTHER PUBLICATIONS

PCT International Search Report for PCT/EP2016/065766, dated Sep. 5, 2016.
Borghini A et al: "QSAR study on thiazole and thiadiazole analogues as antagonists for the adenoside A1 and A3 receptors", Bioorganic & Medicinal Chemistry. vol. 13, No. 18, Sep. 2005, p. 5330-5337.
Database Registry Chemical Abstracts Service, RN 190935-80-9, May 2016, p. 1.
Muijlwijk-Koezen Van J E et al: "Thiazole and Thiadiazole Analogues as a Novel Class of Adenosine Receptor Antagonists", Journal of Medicinal Chemistry, vol. 44, No. 5, Mar. 2001, pp. 749-762.
Database WPI, "5-Amino-1,2,4-thiadiazole (I)" Week 201064, Thomson Scientific, London, GB, Feb. 9, 2015. p. 1-2.

*Primary Examiner* — Laura L Stockton
(74) *Attorney, Agent, or Firm* — McBee Moore Woodward & Vanik IP, LLC

(57) ABSTRACT

The present application relates to thiadiazole compounds, compositions containing such compounds, their use for controlling animal pests including arthropods, insects and nematodes, and to processes and intermediates for the preparation of the thiadiazole compounds.

31 Claims, No Drawings

HETEROCYCLIC COMPOUNDS AS PESTICIDES

CROSS REFERENCE TO RELATED APPLICATIONS

This application is a § 371 National State Application of PCT/EP2016/065766, filed Jul. 5, 2016, which claims priority to European Application No. 15175382.9 filed Jul. 6, 2015.

BACKGROUND OF THE INVENTION

Field of the Invention

The present application relates to thiadiazole compounds, compositions containing such compounds, their use for controlling animal pests including arthropods, insects and nematodes, and to processes and intermediates for the preparation of the thiadiazole compounds.

Description of a Related Art

Certain thiadiazole compounds and their use for controlling pests are known from WO 01/40223 A2. Thiadiazole compounds with a pyridine moiety in the 3-position of the thiadiazole ring system and their use for controlling parasites are disclosed in WO 2015/073797 A1.

Crop protection compositions, which also include pesticides, have to meet many demands, for example in relation to efficacy, persistence, spectrum, resistance breaking properties, pollinator and beneficial safety of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection compositions cannot be considered to be complete, and there is a constant need for novel compounds having properties which, compared to the known compounds, are improved at least in respect of individual aspects.

SUMMARY

It was an object of the present invention to provide compounds which widen the spectrum of the pesticides in various aspects.

This object, and further objects which are not stated explicitly but can be discerned or derived from the connections discussed herein, are achieved by compounds of formula (I) and salts of compounds of formula (I)

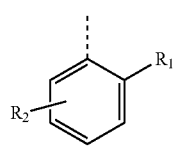

(I)

in which
A represents a radical from the group consisting of

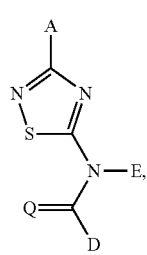

A-1

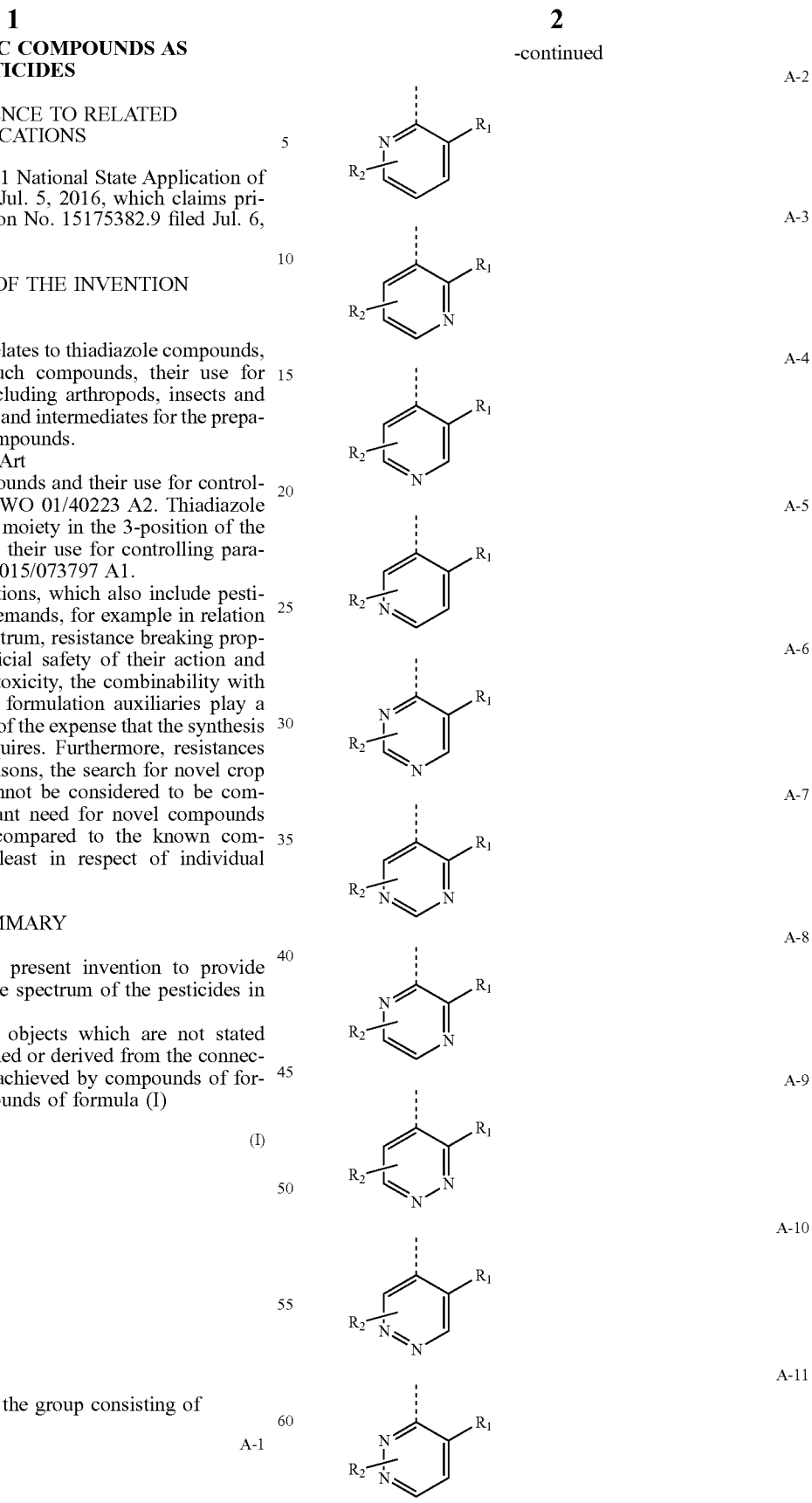

in which the broken line represents the bond to the thiadiazole ring,

D represents a radical from the group consisting of

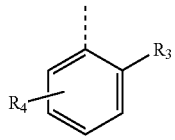 B-1

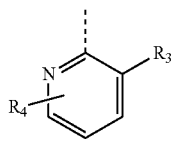 B-2

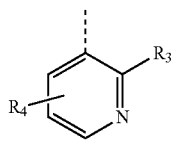 B-3

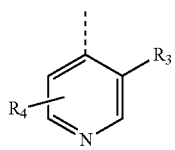 B-4

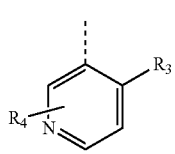 B-5

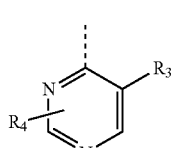 B-6

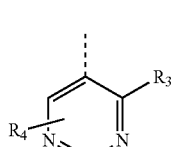 B-7

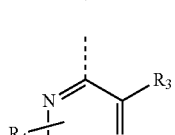 B-8

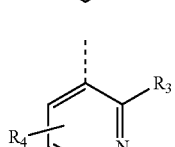 B-9

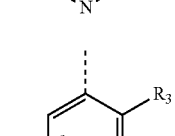 B-10

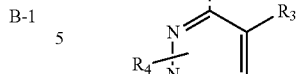 B-11

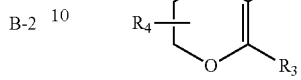 B-12

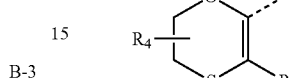 B-13

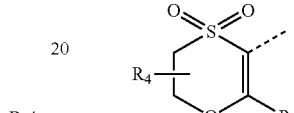 B-14

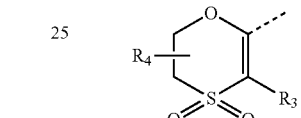 B-15 in which the broken line represents the bond to the carbon atom in C=Q,

E represents hydrogen, $C_1$-$C_6$-alkyl, $C_3$-$C_6$-cycloalkyl, $C_2$-$C_6$-haloalkyl, $C_3$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_1$-$C_6$-alkoxy-$C_1$-$C_6$-alkyl, $C_1$-$C_6$-alkoxycarbonyl, a metal ion, an ammonium ion or represents C(=O)-D, Q represents oxygen or sulfur, $R_1$ represents halogen, cyano, nitro, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_6$-alkenylthio, $C_3$-$C_6$-alkynylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $R_2$ represents hydrogen, halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $R_3$ represents halogen, cyano, nitro, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, $C_3$-$C_6$-alkenoxy, $C_3$-$C_6$-haloalkenoxy, $C_3$-$C_6$-alkynoxy, $C_3$-$C_6$-cycloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl and $R_4$ represents hydrogen, halogen, nitro, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl.

DETAILED DESCRIPTION OF A PREFERRED EMBODIMENT

It has been found that compounds of the formula (I) have pronounced biological properties and are suitable especially for controlling animal pests, in particular insects and arachnids, encountered in agriculture, in forests, in the protection of stored products and materials and in the hygiene sector and for controlling arthropodal parasites on animals, in particular warm-blooded animals.

Preferred are compounds of formula (I) in which

A represents a radical from the group consisting of

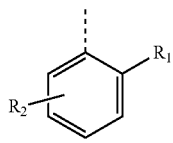
A-1

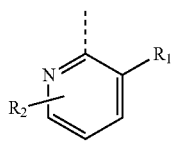
A-2

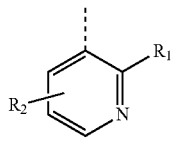
A-3

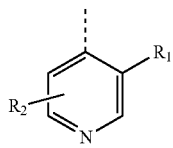
A-4

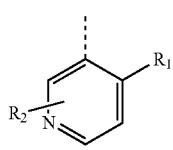
A-5

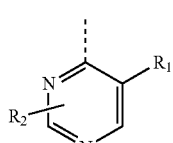
A-6

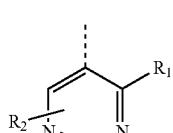
A-7

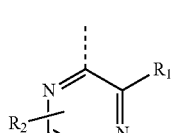
A-8

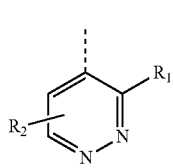
A-9

-continued

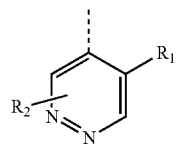
A-10

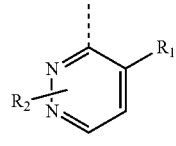
A-11 in which the broken line represents the bond to the thiadiazole ring,

D represents a radical from the group consisting of

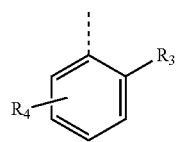
B-1

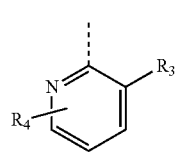
B-2

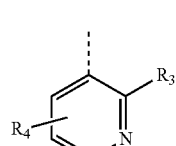
B-3

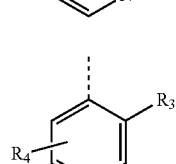
B-4

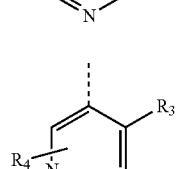
B-5

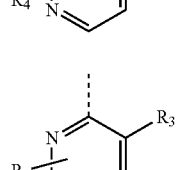
B-6

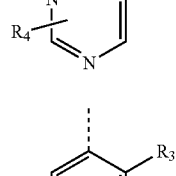
B-7

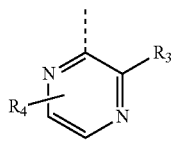 B-8

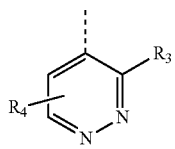 B-9

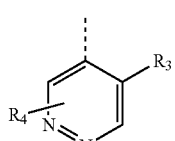 B-10

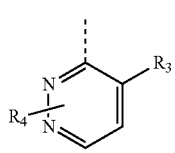 B-11

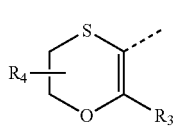 B-12

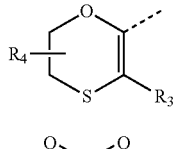 B-13

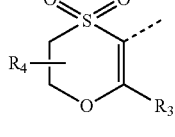 B-14

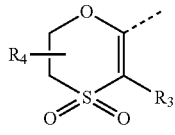 B-15 in which the broken line represents the bond to the carbon atom in C=Q,

E represents hydrogen, $C_1$-$C_4$-alkyl, $C_3$-$C_6$-cycloalkyl, $C_2$-$C_4$-haloalkyl, $C_3$-$C_4$-alkenyl, $C_3$-$C_4$-alkynyl, $C_3$-$C_6$-cycloalkyl-$C_1$-$C_4$-alkyl, cyano-$C_1$-$C_4$-alkyl, $C_1$-$C_4$-alkylcarbonyl, $C_1$-$C_4$-alkoxy-$C_1$-$C_4$-alkyl, $C_1$-$C_4$-alkoxycarbonyl, an alkali metal ion, an earth alkali metal ion, an ammonium ion or represents C(=O)-D, Q represents oxygen or sulfur, $R_1$ represents halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_6$-alkenylthio, $C_3$-$C_6$-alkynylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $R_2$ represents hydrogen, halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $R_3$ represents halogen, cyano, nitro, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, $C_3$-$C_6$-alkenoxy, $C_3$-$C_6$-haloalkenoxy, $C_3$-$C_6$-alkynoxy, $C_3$-$C_6$-cycloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $R_4$ represents hydrogen, halogen, nitro, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl.

Particularly preferred are compounds of formula (I) in which

A represents a radical from the group consisting of

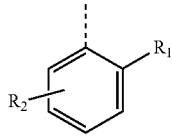 A-1

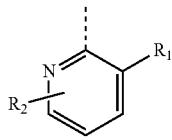 A-2

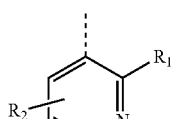 A-3

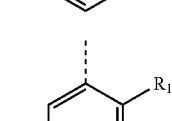 A-4

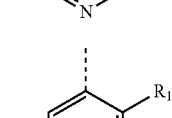 A-5 in which the broken line represents the bond to the thiadiazole ring,

D represents a radical from the group consisting of

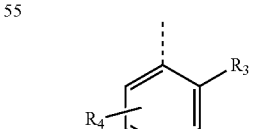 B-1

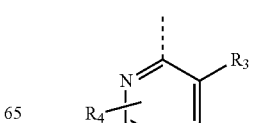 B-2

-continued

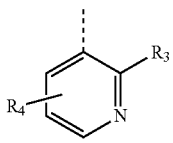
B-3

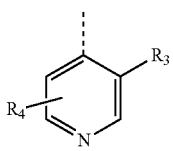
B-4

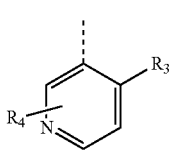
B-5

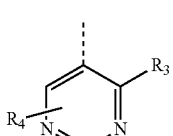
B-7

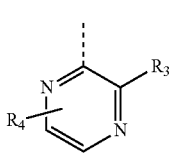
B-8

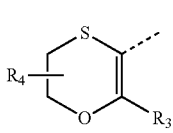
B-12 in which the broken line represents the bond to the carbon atom in C=Q,

E represents hydrogen, $C_1$-$C_4$-alkyl, $C_2$-$C_4$-haloalkyl, cyano-$C_1$-$C_4$-alkyl, $C_1$-$C_4$-alkylcarbonyl, $C_1$-$C_4$-alkoxy-$C_1$-$C_4$-alkyl, $C_1$-$C_4$-alkoxycarbonyl, an alkali metal ion, an earth alkali metal ion, an ammonium ion or represents C(=O)-D, Q represents oxygen or sulfur, $R_1$ represents halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $R_2$ represents hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $R_3$ represents halogen, cyano, nitro, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, $C_1$-$C_4$-alkoxy, $C_1$-$C_4$-haloalkoxy, $C_3$-$C_4$-alkenoxy, $C_3$-$C_4$-haloalkenoxy, $C_3$-$C_4$-alkynoxy, $C_3$-$C_6$-cycloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $R_4$ represents hydrogen, halogen, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl.

Very particularly preferred are compounds of the formula (I) in which

A represents a radical from the group consisting of

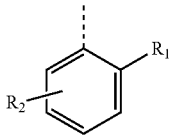
A-1

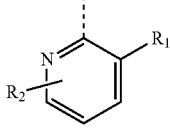
A-2

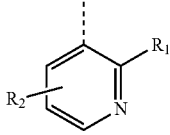
A-3 in which the broken line represents the bond to the thiadiazole ring,

D represents a radical from the group consisting of

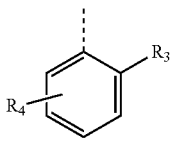
B-1

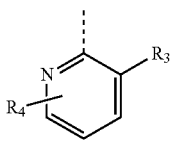
B-2

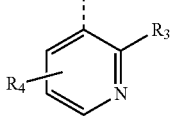
B-3

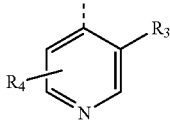
B-4

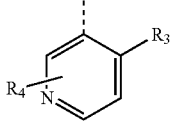
B-5

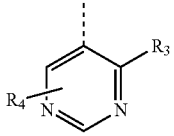
B-7

-continued

B-8

[structure with R3, R4, two N atoms]

B-12

[structure with S, O, R3, R4]

in which the broken line represents the bond to the carbon atom in C=Q,

E represents hydrogen, methyl, ethyl, difluormethyl, trifluormethyl, cyanomethyl, a Li-, Na-, K-, Mg-, Ca-ion, an ammonium ion of formula $$R_8\underset{R_7}{\overset{R_5}{\underset{|}{N^+}}}R_6$$

wherein $R_5$, $R_6$, $R_7$ and $R_8$ independently represent hydrogen, $C_1$-$C_4$-alkyl or benzyl,
or
E represents C(=O)-D,
Q represents oxygen or sulfur,
$R_1$ represents fluorine, chlorine, bromine, iodine, cyano, nitro, methyl, ethyl, n-propyl, i-propyl, difluoromethyl, trifluoromethyl, chloro-difluoromethyl, pentafluoroethyl, cyclopropyl, methoxy, ethoxy difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl,
$R_2$ represents hydrogen, fluorine, chlorine, bromine, iodine, cyano, nitro, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl,
$R_3$ represents fluorine, chlorine, bromine, iodine, cyano, nitro, methyl, ethyl, difluoromethyl, trifluoromethyl, chloro-difluoromethyl, pentafluoroethyl, cyclopropyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl and $R_4$ represents hydrogen, fluorine, chlorine, bromine, iodine, nitro, cyano, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl.

Very particularly preferred are also compounds of the formula (I) in which
A represents a radical from the group consisting of

A-1

[phenyl structure with $R_1$, $R_2$]

A-2

[pyridyl structure with $R_1$, $R_2$]

A-3

[pyridyl structure with $R_1$, $R_2$]

in which the broken line represents the bond to the thiadiazole ring,
D represents a radical from the group consisting of

B-1

[phenyl structure with $R_3$, $R_4$]

B-2

[pyridyl structure with $R_3$, $R_4$]

B-3

[pyridyl structure with $R_3$, $R_4$]

B-7

[pyrimidine structure with $R_3$, $R_4$]

-continued

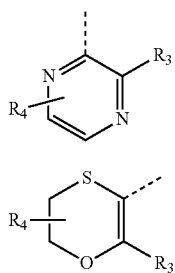

B-8

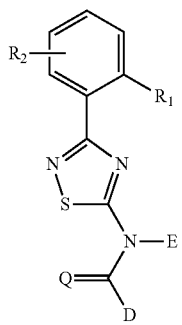

B-12 in which the broken line represents the bond to the carbon atom in C=Q,

E represents hydrogen, methyl, ethyl, a Li-, Na-, K-, Mg-, Ca-ion, or

E represents C(=O)-D,

Q represents oxygen, $R_1$ represents fluorine, chlorine, bromine, iodine, cyano, methyl, ethyl, n-propyl, i-propyl, difluoromethyl, trifluoromethyl, chloro-difluoromethyl, pentafluoroethyl, $R_2$ represents hydrogen, fluorine, chlorine, bromine, iodine, cyano, difluoromethyl, trifluoromethyl, chloro-difluoromethyl, pentafluoroethyl, $R_3$ represents fluorine, chlorine, bromine, iodine, nitro, methyl, ethyl, difluoromethyl, trifluoromethyl, chloro-difluoromethyl, pentafluoroethyl, methoxy, ethoxy and $R_4$ represents hydrogen, fluorine, chlorine, bromine, iodine.

A particularly preferred group of compounds are compounds of formula (I-1)

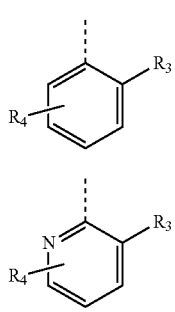

(I-1)

in which

D represents a radical from the group consisting of

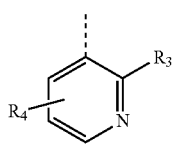

B-1

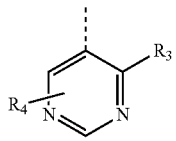

B-2

-continued

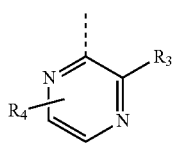

B-3

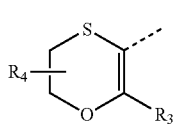

B-7

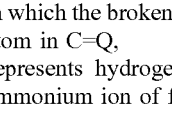

B-8

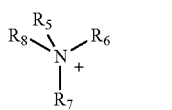

B-12 in which the broken line represents the bond to the carbon atom in C=Q,

E represents hydrogen; a Li-, Na-, K-, Mg-, Ca-ion, an ammonium ion of formula

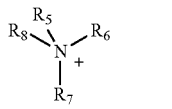

wherein $R_5$, $R_6$, $R_7$ and $R_8$ independently represent hydrogen, methyl, ethyl or benzyl, Q represents oxygen, $R_1$ represents fluorine, chlorine, bromine, iodine, cyano, nitro, methyl, ethyl, n-propyl, i-propyl, difluoromethyl, trifluoromethyl, chloro-difluoromethyl, pentafluoroethyl, cyclopropyl, methoxy, ethoxy, -difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl, $R_2$ represents hydrogen, fluorine, chlorine, bromine, iodine, cyano, nitro, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl, $R_3$ represents fluorine, chlorine, bromine, iodine, cyano, nitro, methyl, ethyl, difluoromethyl, trifluoromethyl, chloro-difluoromethyl, pentafluoroethyl, cyclopropyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl, and $R_4$ represents hydrogen, fluorine, chlorine, bromine, iodine, nitro, cyano, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl.

Another particularly preferred group of compounds are compounds of formula (I-1)

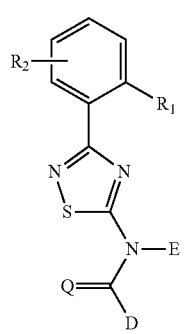
(I-1)

in which
D represents a radical from the group consisting of

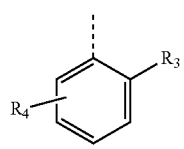
B-1

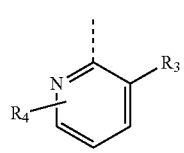
B-2

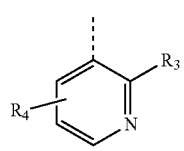
B-3

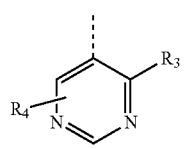
B-7

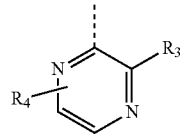
B-8

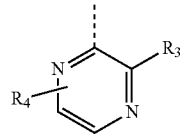
B-12 in which the broken line represents the bond to the carbon atom in C=Q,

E represents hydrogen,

Q represents oxygen, $R_1$ represents fluorine, chlorine, bromine, iodine, cyano, methyl, ethyl, n-propyl, i-propyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy, $R_2$ represents hydrogen, fluorine, chlorine, bromine, iodine, cyano, difluoromethyl, trifluoromethyl, chloro-difluoromethyl, pentafluoroethyl, $R_3$ represents fluorine, chlorine, bromine, iodine, nitro, methyl, ethyl, difluoromethyl, trifluoromethyl, chloro-difluoromethyl, pentafluoroethyl, methoxy, ethoxy, and $R_4$ represents hydrogen, fluorine, chlorine, bromine, iodine.

Another particularly preferred group of compounds are compounds of formula (I-2)

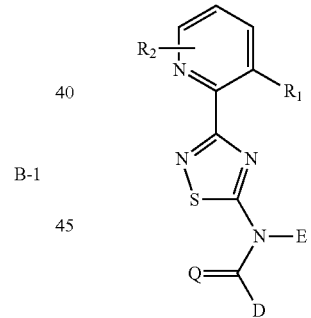
(I-2)

in which
D represents a radical from the group consisting of

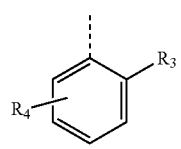
B-1

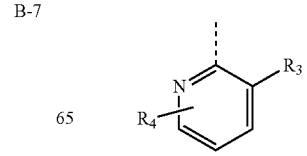
B-2

-continued

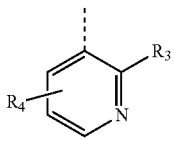
B-3

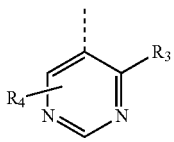
B-7

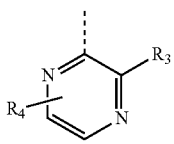
B-8

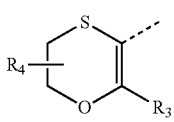
B-12 in which the broken line represents the bond to the carbon atom in C=Q,

E represents hydrogen, a Li-, Na-, K-, Mg-, Ca-ion, an ammonium ion of formula

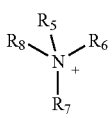

wherein $R_5$, $R_6$, $R_7$ and $R_8$ independently represent hydrogen, methyl, ethyl or benzyl, Q represents oxygen, $R_1$ represents fluorine, chlorine, bromine, iodine, cyano, nitro, methyl, ethyl, n-propyl, i-propyl, difluoromethyl, trifluoromethyl, chloro-difluoromethyl, pentafluoroethyl, cyclopropyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl, $R_2$ represents hydrogen, fluorine, chlorine, bromine, iodine, cyano, nitro, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl, $R_3$ represents fluorine, chlorine, bromine, iodine, cyano, nitro, methyl, ethyl, difluoromethyl, trifluoromethyl, chloro-difluoromethyl, pentafluoroethyl, cyclopropyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl, and $R_4$ represents hydrogen, fluorine, chlorine, bromine, iodine, nitro, cyano, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, trifluoroethylsulphonyl.

Another particularly preferred group of compounds are compounds of formula (I-2)

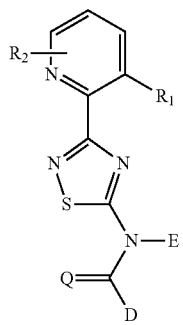
(I-2)

in which

D represents a radical from the group consisting of

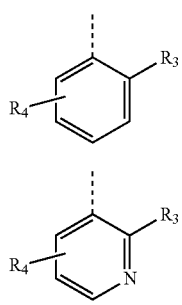
B-1

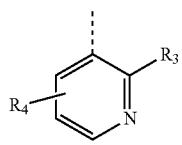
B-3 in which the broken line represents the bond to the carbon atom in C=Q,

E represents hydrogen,

Q represents oxygen, $R_1$ represents fluorine, chlorine, bromine, iodine, $R_2$ represents hydrogen, fluorine, chlorine, bromine, iodine, difluoromethyl, trifluoromethyl, chloro-difluoromethyl, pentafluoroethyl, $R_3$ represents fluorine, chlorine, bromine, iodine, difluoromethyl, trifluoromethyl, chloro-difluoromethyl, pentafluoroethyl, and $R_4$ represents hydrogen.

Another particularly preferred group of compounds are compounds of formula (I-3)

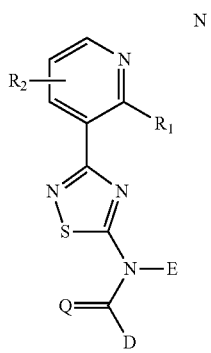

(I-3)

in which
D represents a radical from the group consisting of

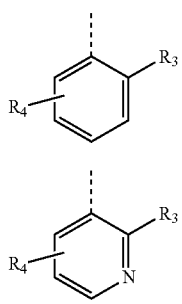

B-1

B-3 in which the broken line represents the bond to the carbon atom in C=Q,
E represents hydrogen,
Q represents oxygen,
$R_1$ represents fluorine, chlorine, bromine, iodine,
$R_2$ represents hydrogen,
$R_3$ represents fluorine, chlorine, bromine, iodine, difluoromethyl, trifluoromethyl, chloro-difluoromethyl, pentafluoroethyl, and
$R_4$ represents hydrogen.

In the above definitions, unless stated otherwise, halogen is selected from the group of fluorine, chlorine, bromine and iodine, preferably in turn from the group of fluorine, chlorine and bromine.

Halogen-substituted radicals, for example haloalkyl, are mono- or polyhalogenated, up to the maximum number of possible substituents. In the case of polyhalogenation, the halogen atoms may be identical or different. Halogen denotes fluorine, chlorine, bromine and iodine, in particular fluorine, chlorine and bromine.

The term "alkenoxy" is synonymous with "alkenyloxy", "alkynoxy" is synonymous with "alkynyloxy".

Saturated or unsaturated hydrocarbyl radicals, such as alkyl or alkenyl, may in each case be straight-chain or branched as far as possible, including in combination with heteroatoms, as, for example, in alkoxy.

Optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

In a preferred group of compounds of formula (I) A represents A-1.
In another preferred group of compounds of formula (I) A represents A-2.
In another preferred group of compounds of formula (I) A represents A-3.
In another preferred group of compounds of formula (I) D represents B-1.
In another preferred group of compounds of formula (I) D represents B-2.
In another preferred group of compounds of formula (I) D represents B-3.
In another preferred group of compounds of formula (I) D represents B-8.
In another preferred group of compounds of formula (I) A represents A-1 and D represents B-1.
In another preferred group of compounds of formula (I) A represents A-1 and D represents B-2.
In another preferred group of compounds of formula (I) A represents A-1 and D represents B-3.
In another preferred group of compounds of formula (I) A represents A-1 and D represents B-8.
In another preferred group of compounds of formula (I) A represents A-2 and D represents B-1.
In another preferred group of compounds of formula (I) A represents A-2 and D represents B-3.
In another preferred group of compounds of formula (I) A represents A-3 and D represents B-1.
In another preferred group of compounds of formula (I) A represents A-3 and D represents B-3.
In another preferred group of compounds of formula (I) $R_2$ must be not represent hydrogen in A-2, if $R_1$ is fluorine in A-2.
In a preferred group of compounds of formula (I-2) $R_2$ must be not represent hydrogen, if $R_1$ is fluorine.

It has additionally been found that compounds of the formula (I) can be obtained by the processes described below.

Accordingly, the invention also relates to processes for preparing compounds of the formula (I) in which Q represents oxygen and E represents hydrogen. In the groups of compounds below, the individual radicals A and D have the meanings given above.

Compounds of formula (I) wherein E represents $E^a$ ($E^a$=H) and Q=oxygen can be obtained from the amine of formula (II) either by amide coupling with a carboxylic acid of formula (III) or by reaction with an acyl chloride of formula (IV) (synthesis scheme 1).

In case of the amide reaction (route A), in addition to the acid (III) and the amine (II) a base such as ethyl-N,N-diisopropylamine and a coupling agent such as bromo(tri-1-pyrrolidinyl)phosphonium hexafluorophosphate (PY-BrOP) can be used in a solvent such as dichloromethane. Alternatively coupling agents such as 1-[bis(dimethylamino)methylene]-1H-1,2,3-triazolo[4,5-b]pyridinium 3-oxid hexafluorophosphate) (HATU) can be used in a solvent such as dimethylformamide with or without a catalytic amount of 4-(N,N-dimethylamino)pyridine, at a temperature of e.g. 80° C.

In case of the reaction with an acyl chloride (route B) a base is used in systems such as
- ethyl-N,N-diisopropylamine in acetonitrile, with or without heating,
- ethyl-N,N-diisopropylamine in chloroform with or without 4-(N,N-dimethylamino)pyridine,
- triethylamine in dichloromethane at room temperature,
- sodium hydride in tetrahydrofuran at room temperature Acyl chlorides of formula (IV) are commercially available or can be prepared from the corresponding carboxylic acids of formula (III) using a chlorinated agent such as thionyl chloride in a solvent such as toluene.

Synthesis Scheme 1

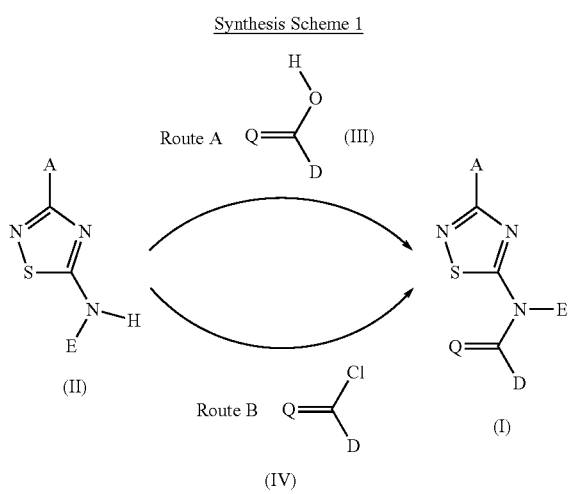

Compounds of formula (I) wherein E represents $E^b$ ($E^b$ being a metal ion or ammonium ion) and Q represents oxygen can be obtained from compounds of formula (I) wherein E represents H using a strong base, for example sodium methoxide as shown in synthesis scheme 2.

Compounds of formula (I) wherein E represents $E^c$ ($E^c$ being $C_1$-$C_6$-alkyl), can be obtained by alkylation of the NH of the amide function using a base such as sodium hydride in a solvent such as dimethylformamide with a bromo- or iodo-$C_1$-$C_6$-alkyl reagent.

Compounds of formula (I) wherein E represents $E^d$ ($E^d$ being COAr), can be obtained by over-benzoylation using the amine of formula (II) and an excess of base e.g. ethyl-N,N-diisopropylamine and an excess of benzoyl chloride ClCOD.

Synthesis Scheme 2

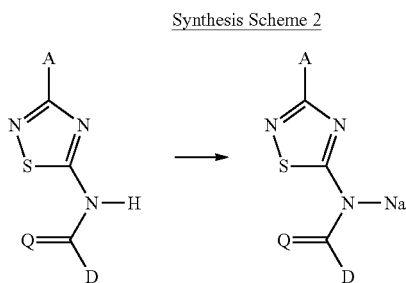

Some amines of formula (II) are commercially available, for example the following ones:
3-(2-chlorophenyl)-1,2,4-thiadiazol-5-amine; 3-[2-(trifluoromethyl)phenyl]-1,2,4-thiadiazol-5-amine; 3-(3-chloropyridin-2-yl)-1,2,4-thiadiazol-5-amine and 3-[3-chloro-5-(trifluoromethyl)pyridin-2-yl]-1,2,4-thiadiazol-5-amine.

Novel amines of formula (II-2) such as 3-(2,6-difluorophenyl)-1,2,4-thiadiazol-5-amine or
3-(2-chloropyridin-3-yl)-1,2,4-thiadiazol-5-amine can be obtained as shown in synthesis scheme 3.

Synthesis Scheme 3

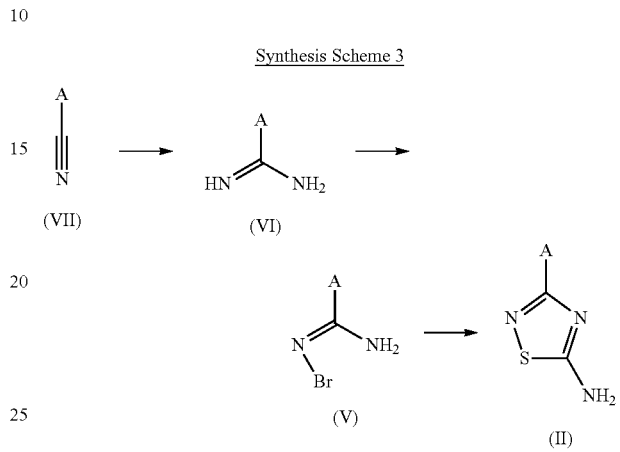

Nitriles of formula (VII) can react with lithium hexamethyldisilazide (LiHMDS) in a solvent such as tetrahydrofuran to give amidines of formula (VI). Alternatively the nitriles of formula (VII) can be transformed into amidines of formula (VI) using a mixture of trimethylaluminium and ammonium chloride in a solvent such as toluene to which the nitrile (VII) is added dropwise at a temperature such as 0° C. The reaction mixture is then heated to e.g. 80° C. In some cases, the amidine is commercially available.

Amidines of formula (VI) can be brominated with e.g. N-bromosuccinimide to give the brominated intermediates of formula (V). Intermediates of formula (V) can be cyclized to yield the thiadiazole-amines of formula (II) using an agent such as potassium thiocyanate in a solvent such as methanol. Alternatively the amidines of formula (VI) can be transformed into thiadiazole-amines of formula (II) without isolating the intermediates of formula (V) in a one pot process. The reaction is performed in presence of a base such as triethylamine, using first a brominating agent such as bromine in a solvent such as methanol e.g. at 0° C. subsequently followed by addition of potassium thiocyanate.

Compounds of formula (I) wherein E represents $E^a$ ($E^a$=H) can also be obtained by reaction of the boronic acid of formula (VIII) with the bromo-thiadiazole adduct of formula (IX) (Suzuki coupling, see synthesis scheme 4) using for example the X-phos aminobiphenyl palladium chloride precatalyt as well as a base, e.g. potassium phosphate in a solvent mixture such as tetrahydrofuran/water, at a temperature of e.g. 60° C. The bromo-thiadiazole of formula (IX) can be obtained by amide coupling between the carboxylic acid of formula (III) and the amine of formula (X) in the presence of a coupling agent such as HATU and a base such as ethyl-N,N-diisopropylamine, at a temperature of e.g. 80° C. Bromothiadiazol-amines of formula (X) can be obtained by reaction of ammonia with 3-bromo-5-chlorothiadiazole (XI).

Synthesis Scheme 4

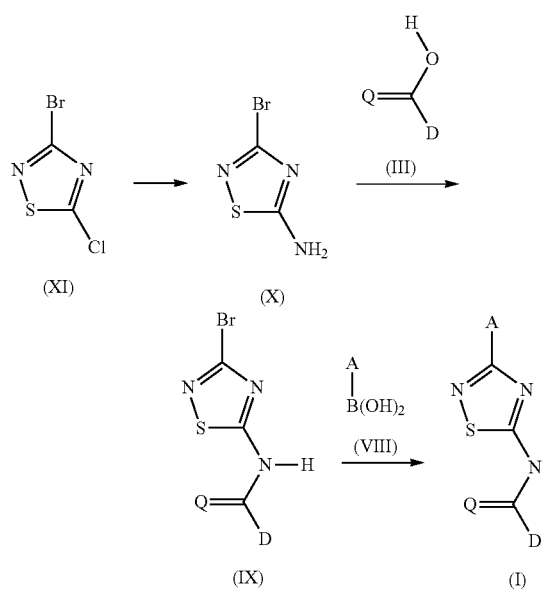

In some particular cases, compounds of formula (I) wherein E represents $E^a$ ($E^a$=H) have been obtained by Langlois trifluoromethylation reaction using sodium trifluoromethanesulfinate, copper (II) triflate and t-butylhydroperoxide in a solvent such as acetonitrile. This is the case for compounds I-1-62, I-1-65 and I-1-66 as depicted in Table 1. In other particular cases compounds of formula (I) wherein E represents $E^a$ ($E^a$=H) were obtained by iodination with a iodo source such as N-iodosuccinimide using palladium acetate followed by cyanation using for example copper (I) cyanide. This is the case for compounds I-1-67 and I-1-78 (see Table 1).

The processes according to the invention for the preparation of compounds of the formula (I) are preferably performed using a diluent. Useful diluents for performance of the processes according to the invention are, as well as water, all inert solvents. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, benzene, toluene, xylene, esters (for example methyl, ethyl, butyl and isobutyl acetate, dimethyl, dibutyl and ethylene carbonate); amides (for example hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

It is of course also possible to perform the process according to the invention in mixtures of the solvents and diluents mentioned.

When performing the process according to the invention, the reaction temperatures can be varied within a relatively wide range. In general, the temperatures employed are between −30° C. and +150° C., preferably between −10° C. and +100° C.

The process according to the invention is generally performed under atmospheric pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a relatively large excess. The reaction is generally carried out in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the preparation examples).

The basic reaction auxiliaries used to perform the process according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, 2-picoline, 3-picoline, pyrimidine, acridine, N,N,N',N'-tetramethylenediamine, N,N,N', N'-tetraethylenediamine, quinoxaline, N-propyldiisopropylamine, N-ethyldiisopropylamine, N,N'-dimethylcyclohexylamine, 2,6-lutidine, 2,4-lutidine or tri-ethylenediamine).

The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesul-phonic acid).

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded herefrom are methods for the surgical or therapeutic treatment of the human or animal body and diagnostic methods carried out on the human or animal body.

The invention furthermore relates to the use of the compounds of the formula (I) as pesticides, in particular crop protection agents.

In the context of the present application, the term "pesticide" in each case also always comprises the term "crop protection agent".

The compounds of the formula (I), having good plant tolerance, favourable homeotherm toxicity and good environmental compatibility, are suitable for protecting plants and plant organs against biotic and abiotic stressors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

Within the context of the present patent application, the term "hygiene" is understood to mean any and all measures, procedures and practices which aim to prevent disease, in particular infectious disease, and which serve to protect the health of humans and animals and/or to protect the environment, and/or which maintain cleanliness. In accordance with the invention, this especially includes measures for cleaning, disinfection and sterilisation of, for example, textiles or hard surfaces, especially surfaces of glass, wood, concrete, porcelain, ceramics, plastic or also of metal(s), and for ensuring that these are kept free of hygiene pests and/or their faeces. On the other hand, excluded from the scope of the invention in this regard are surgical or therapeutic treatment procedures applicable to the human body or to the bodies of animals and diagnostic procedures which are carried out on the human body or on the bodies of animals.

The term "hygiene sector" thus covers all areas, technical fields and industrial applications in which these hygiene measures, procedures and practices are important, in relation for example to hygiene in kitchens, bakeries, airports, bathrooms, swimming pools, department stores, hotels, hospitals, stables etc.

The term "hygiene pest" is therefore understood to mean one or more animal pests whose presence in the hygiene sector is problematic, in particular for health reasons. It is therefore a primary objective to avoid or minimize the presence of hygiene pests, and/or exposure to them, in the hygiene sector. This can be achieved in particular through the application of a pesticide that can be used both to prevent infestation and to tackle an infestation which is already present. Preparations which avoid or reduce exposure to pests can also be used. Hygiene pests include, for example, the organisms mentioned below.

The term "hygiene protection" thus covers all actions to maintain and/or improve these hygiene measures, procedures and practices.

The compounds of the formula (I) can preferably be used as pesticides. They are active against normally sensitive and resistant species and against all or some stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus (=Polyphagotarsonemus latus), Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri (=Metatetranychus citri), Panonychus ulmi (=Metatetranychus ulmi), Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Peri-*

*planeta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=*Hyperodes*) spp., *Lixus* spp., *Luperodes* spp., *Luperomorpha xanthodera, Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor,* *Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chio-*

*naspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus vibumi, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus pemiciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta*

*padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata*; pests from the phylum of the Mollusca, for example from the class of the Bivalvia, for example *Dreissena* spp., and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platylminthes and Nematoda, for example *Aelurostrongylus* spp., *Amidostomum* spp., *Ancylostoma* spp, for example *Ancylostoma duodenale, Ancylostoma ceylanicum, Acylostoma braziliensis, Angiostrongylus* spp., *Anisakis* spp., *Anoplocephala* spp., *Ascaris* spp., *Ascaridia* spp., *Baylisascaris* spp., *Brugia* spp., for example *Brugia malayi, Brugia timori, Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., for example *Dictyocaulus filaria, Diphyllobothrium* spp., for example *Diphyllobothrium latum, Dipylidium* spp., *Dirofilaria* spp., *Dracunculus* spp., for example *Dracunculus medinensis, Echinococcus* spp., for example *Echinococcus granulosus, Echinococcus multilocularis, Echinostoma* spp., *Enterobius* spp., *Enterobius vermicularis, Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., for example *Hymenolepis nana, Hyostrongylus* spp., *Litomosoides* spp., *Loa* spp., for example *Loa Loa, Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, for example *Onchocerca volvulus, Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., for example *Strongyloides fuelleborni, Strongyloides stercoralis, Strongylus* spp., *Syngamus* spp., *Taenia* spp., for example *Taenia saginata, Taenia solium, Teladorsagia* spp., *Thelazia* spp., *Toxascaris* spp., *Toxocara* spp., *Trichinella* spp., for example *Trichinella spiralis, Trichinella nativa, Trichinella britovi, Trichinella nelsoni, Trichinella pseudopsiralis, Trichobilharzia* spp., *Trichostrongylus* spp., *Trichuris* spp., for example *Trichuris trichiura, Uncinaria* spp., *Wuchereria* spp., for example *Wuchereria bancrofti;* plant pests from the phylum of the Nematoda, i.e. phytoparasitic nematodes, in particular *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hirschmaniella* spp., *Hoplolaimus* spp., *Longidorus* spp., for example *Longidorus africanus*, *Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema* index.

Furthermore, it is possible to control, from the subkingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are prepared either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms is usually between 0.00000001 and 95% by weight of the compound of the formula (I), preferably between 0.00001 and 1% by weight, based on the weight of the use form. The compounds are employed in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, cyclodiene-organochlorines, for example chlordane and endosulfan or phenylpyrazoles (fiproles), for example ethiprole and fipronil.

(3) Sodium channel modulators/voltage-gated sodium channel blockers such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinergic acetylcholine receptor (nAChR) agonists, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Allosteric activators of the nicotinergic acetylcholine receptor (nAChR) such as, for example, spinosyns, e.g. spinetoram and spinosad.

(6) Chloride channel activators, such as, for example, avermectins/milbemycins, for example abamectin, emamectin benzoate, lepimectin and milbemectin.

(7) Juvenile hormone imitators such as, for example, juvenile hormone analogues, e.g. hydroprene, kinoprene and methoprene or fenoxycarb or pyriproxyfen.

(8) Active compounds with unknown or nonspecific mechanisms of action such as, for example, alkyl halides, e.g. methyl bromide and other alkyl halides; or chloropicrine or sulphuryl fluoride or borax or tartar emetic.

(9) Selective antifeedants, for example pymetrozine or flonicamid.

(10) Mite growth inhibitors, for example clofentezine, hexythiazox and diflovidazin or etoxazole.

(11) Microbial disruptors of the insect gut membrane, for example Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron or organotin compounds, for example azocyclotin, cyhexatin and fenbutatin oxide or propargite or tetradifon.

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocylam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone or acequinocyl or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase such as, for example, tetronic and tetramic acid derivatives, e.g. spirodiclofen, spiromesifen and spirotetramat.

(24) Complex-IV electron transport inhibitors such as, for example, phosphines, e.g. aluminium phosphide, calcium phosphide, phosphine and zinc phosphide or cyanide.

(25) Complex II electron transport inhibitors, such as, for example, cyenopyrafen and cyflumetofen.

(28) Ryanodine receptor effectors, such as, for example, diamides, e.g. chlorantraniliprole, cyantraniliprole and flubendiamide, further active compounds such as, for example, Afidopyropen, Afoxolaner, Azadirachtin, Benclothiaz, Benzoximate, Bifenazate, Broflanilide, Bromopropylate, Chinomethionat, Cryolite, Cyclaniliprole, Cycloxaprid, Cyhalodiamide Dicloromezotiaz, Dicofol, Diflovidazin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, Lotilaner, Meperfluthrin, Paichongding, Pyflubumide, Pyridalyl, Pyrifluquinazon, Pyriminostrobin, Sarolaner, Tetramethylfluthrin, Tetraniliprole, Tetrachlorantraniliprole, Tioxazafen, Thiofluoximate, Triflumezopyrim and iodomethane; furthermore preparations based on Bacillus firmus (I-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl] piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbony}amino)-5-cyano-3-methylbenzoyl]-2-methy hydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969, butyl [2-(2,4-dichlorophenyl)-3-oxo-4-oxaspiro[4.5]dec-1-en-1-yl] carbonate (known from CN 102060818), 3E)-3-[1-[(6-chloro-3-pyridyl)methyl]-2-pyridylidene]-1,1,1-trifluoropropan-2-one (known from WO2013/144213), N-(methylsulfonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926), 5-bromo-4-chloro-N-[4-chloro-2-methyl-6-(methylcarbamoyl)phenyl]-2-(3-chloro-2-pyridyl)pyrazole-3-carboxamide (known from CN103232431).

Fungicides

The active ingredients specified herein by their Common Name are known and described, for example, in The Pesticide Manual (16th Ed. British Crop Protection Council) or can be searched in the internet (e.g. www.alanwood.net/pesticides).

All named fungicidal mixing partners of the classes (1) to (15) can, if their functional groups enable this, optionally form salts with suitable bases or acids. All named mixing partners of the classes (1) to (15) can include tautomeric forms, where applicable.

1) Inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-({5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl] 1H-imidazole-1-carbothioate, (1.65) Pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-yl thiocyanate, (1.68) 5-(allylsulfanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl]methyl}-1H-1,2,4-triazol-5-yl thiocyanate, (1.74) 5-(allylsulfanyl)-1-{[rel(2R,3S)-3-(2-chlorophenyl)-2-(2,4-difluorophenyl)oxiran-2-yl]methyl}-1H-1,2,4-triazole, (1.75) 5-(allylsulfanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1- chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) Isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) Fenaminostrobin, (3.28) 5-methoxy-2-methyl-4-(2-{[({(1E)-1-[3-(trifluoromethyl)phenyl]ethylidene}amino)

oxy]methyl}phenyl)-2,4-dihydro-3H-1,2,4-triazol-3-one, (3.29) methyl (2E)-2-{2-[({cyclopropyl[(4-methoxyphenyl)imino]methyl}sulfanyl)methyl]phenyl}-3-methoxyacrylate, (3.30) N-(3-ethyl-3,5,5-trimethylcyclohexyl)-3-formamido-2-hy droxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of the mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable to have a multisite action, for example (5.01) bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable to induce a host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of the ATP production, for example (8.01) fentin acetate, (8.02) fentin chloride, (8.03) fentin hydroxide, (8.04) silthiofam.

9) Inhibitors of the cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of the melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of the nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazol, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of the signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable to act as an uncoupler, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulfate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and its salts, (15.041) propamocarb-fosetylate, (15.042) propanosine-sodium, (15.043) pyrimorph, (15.044) pyrrolnitrine, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5 S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) Oxathiapiprolin, (15.055) 1-(4-methoxyphenoxy)-3,3-dimethylbutan-2-yl 1H-imidazole-1-carboxylate, (15.056) 2,3,5,6-tetrachloro-4-(methylsulfonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4- chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulfonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amine, (15.073) 5-methyl-6-octyl[1,2,4]triazolo[1,5-a]pyrimidin-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N-{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulfate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulfonyl)valinamide, (15.094) 4-oxo-4-[(2-phenylethyl)amino]butanoic acid, (15.095) but-3-yn-1-yl{6-[({[(Z)-(1-methyl-1H-tetrazol-5-yl)(phenyl)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) Abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2- bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulfanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulfanyl]phenoxy}phenyl)-N-ethyl-N-methylimidoformamide, (15.152) N'-(2,5-dimethyl-4-{3-[(2,2,2-trifluoroethyl)sulfanyl]phenoxy}phenyl)-N-ethyl-N-methylimidoformamide, (15.153) N'-(2,5-dimethyl-4-{3-[(2,2,3,3-tetrafluoropropyl)sulfanyl]phenoxy}phenyl)-N-ethyl-N-methylimidoformamide, (15.154) N'-(2,5-dimethyl-4-{3-[(pentafluoroethyl)sulfanyl]phenoxy}phenyl)-N-ethyl-N-methylimidoformamide, (15.155) N'-(4-{[3-(difluoromethoxy)phenyl]sulfanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulfanyl}phenyl)-N-ethyl-N-methylimidoformamide, (15.157) N'-(2,5-dimethyl-4-{[3-(2,2,2-trifluoroethoxy)phenyl]sulfanyl}phenyl)-N-ethyl-N-methylimidoformamide, (15.158) N'-(2,5-dimethyl-4-{[3-(2,2,3,3-tetrafluoropropoxy)phenyl]sulfanyl}phenyl)-N-ethyl-N-methylimidoformamide, (15.159) N'-(2,5-dimethyl-4-{[3-(pentafluoroethoxy)phenyl]sulfanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydrro-,2-oxazol-5-yl}-3-chlorophenyl methanesulfonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-y-yloxy)phenyl]-4,5-dihydro-1,2-oxazol-3-yl}-,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as spore-forming bacteria, root-colonising bacteria and bacteria which act as biological insecticides, fungicides or nematicides.

Examples of such bacteria which are employed or can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain I-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are employed or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KVO1, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accesion No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM 1-952).

Examples of viruses which are employed or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., *Streptomyces* spp.

Examples of plant extracts and products formed by microorganisms including proteins and secondary metabolites which are employed or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, Dryopteris filix-mas, *Equisetum arvense*, Fortune Aza, Fungastop, Heads Up (*Chenopodium quinoa* saponin extract), Pyrethrum/Pyrethrins, *Quassia amara*, Quercus, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, in particular oilseed rape powder or mustard powder.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, pepper, cucumber, melon, carrot, watermelon, onion, lettuce, spinach, leek, beans, *Brassica oleracea* (e.g. cabbage) and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plants should be understood to mean all developmental stages, such as seeds, seedlings, young (immature) plants up to mature plants. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants or harvested plant parts and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), furthermore increased resistance of the plants against phytopathogenic fungi, bacteria and/or viruses owing, for example, to systemic acquired resistance (SAR), systemin, phytoalexins, elicitors and also resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants. In the case of paddy rice crops, this can also be done by metering the compound of the formula (I) in a solid application form (for example as granules) into a flooded paddy field.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape, vegetables and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water to a certain stage of the rice embryo ('pigeon breast stage'), stimulating the germination and a more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions.

Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term endoparasites includes in particular helminths and protozoans, such as coccidia. Ectoparasites are typically and preferably arthropods, in particular insects and acarids.

In the field of veterinary medicine the compounds of the formula (I) are suitable, with favourable homeotherm toxicity, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffaloes, rabbits, reindeers, fallow deers, and in particular cattle and pigs; or poultry such as turkeys, ducks, geese, and in particular chickens; fish and crustaceans, for example in aquaculture; and also insects such as bees.

Domestic animals include, for example, mammals, such as hamsters, guinea pigs, rats, mice, chinchillas, ferrets and in particular dogs, cats, cage birds, reptiles, amphibians and aquarium fish.

According to a preferred embodiment, the compounds of the formula (I) are administered to mammals.

According to another preferred embodiment, the compounds of the formula (I) are administered to birds, namely cage birds and in particular poultry.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the compounds of the formula (I) are effective in reducing the incidence of the respective parasite in an animal infected with such parasites to innocuous levels. More specifically, "controlling", as used herein, means that the compound of the formula (I) is effective in killing the respective parasite, inhibiting its growth, or inhibiting its proliferation.

Arthropods include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; as well as nuisance and hygiene pests from the order of the Blattarida.

Arthropods furthermore include:

from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi-host ticks); from the order of mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombicula* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa Include:

Mastigophora (*Flagellata*) such as, for example, Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example, *Giardia lamblia, G. canis.*;

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (Sporozoa) such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E.* spec., *E. stiedai, E. suis, E. tenella, E. truncata, E. truttae, E. zuemii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadidae, for example, *Toxoplasma gondii, Hammondia heydomii, Neospora caninum, Besnoitia besnoitii*; such as Sarcocystidae, for example, *Sarcocystis bovicanis, S. bovihominis, S. ovicanis, S. ovifelis, S. neurona, S.* spec., *S. suihominis*, such as Leucozoidae, for example, *Leucozytozoon simondi*, such as Plasmodiidae, for example, *Plasmodium berghei, P. falciparum, P. malariae, P. ovale, P. vivax, P.* spec., such as Piroplasmea, for example, *Babesia argentina, B. bovis, B. canis, B.* spec., *Theileria parva, Theileria* spec., such as Adeleina, for example, *Hepatozoon canis*, H. spec.

Pathogenic endoparasites, which are helminths, include Platyhelmintha (e.g. Monogenea, cestodes and trematodes), nematodes, Acanthocephala, and Pentastoma, including:

Monogenea: e.g.: *Gyrodactylus* spp., *Dactylogyrus* spp., *Polystoma* spp.;

Cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.;

from the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.;

Nematodes: Trichinellida zum Beispiel: *Trichuris* spp., *Capillaria* spp., *Paracapillaria* spp., *Eucoleus* spp., *Trichomosoides* spp., *Trichinella* spp.;

from the order of the Tylenchida for example: *Micronema* spp., *Strongyloides* spp.;

from the order of the Rhabditida for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, administration of the compounds of the formula (I) is carried out by methods generally known in the art, such as enterally, parenterally, dermally or nasally in the form of suitable preparations. Administration can be carried out prophylactically or therapeutically.

Thus, one embodiment of the present invention refers to the use of a compound of the formula (I) as medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, in particular a helminthicidal agent or antiprotozoic agent, for example in animal husbandry, in animal breeding, in animal housing and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in stables or in the hygiene sector.

Anthelmintic Mixing Components

The following anthelmintic mixing components may be mentioned by way of example:

Anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole; from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole; from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:

1) Mosquitoes

*Anopheles*: malaria, filariasis;

*Culex*: Japanese encephalitis, filariasis, other viral diseases, transmission of worms;

*Aedes*: yellow fever, dengue fever, filariasis, other viral diseases;

Simuliidae: transmission of worms, in particular *Onchocerca volvulus*;

2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the sense of the present invention are insects, for example aphids, flies, leafhoppers or thrips, which are capable of transmitting plant viruses to plants. Other vectors capable of transmitting plant viruses are spider mites, lice, beetles and nematodes.

Further examples of vectors in the sense of the present invention are insects and arachnids such as mosquitoes, in particular of the genera *Aedes, Anopheles*, for example *A. gambiae, A. arabiensis, A. funestus, A. dirus* (malaria) and *Culex*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids and mites encountered in enclosed spaces such as dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The Preparation and Use Examples which follow illustrate the invention without limiting it. cl PREPARATION EXAMPLES Synthesis Example 1

N-[3-(2,6-difluorophenyl)-1,2,4-thiadiazol-5-yl]-2,6-difluorobenzamide (Compound I-1-1 in Table 1)

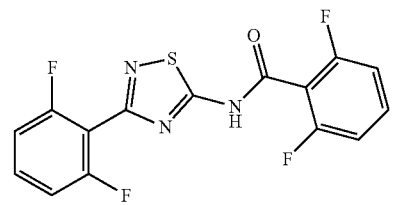 [SMILES: O=C(Nc1nc(-c2c(F)cccc2F)ns1)c1c(F)cccc1F]

3-(2,6-Difluorophenyl)-1,2,4-thiadiazol-5-amine (200 mg) was initially charged in acetonitrile. Diisopropylethylamine (303 mg) and 2,6-difluorobenzoyl chloride (215 mg) were added and the reaction mixture was heated at reflux for 15 hours. The reaction mixture was evaporated. Some ethyl acetate was added. The organic phase was washed with water, dried and evaporated. The residue was purified by column chromatography on silica gel using the mobile phase cyclohexane/ethyl acetate (gradient cyclohexane-ethyl acetate from 50%-50% to 0%-100%). This afforded 270 mg of the title compound.

HPLC-MS: mass (m/z): 354.0 (M+H)+

$^1$H-NMR (400.0 MHz, $d_6$-DMSO): see peak list for compound I-1-1 (Table 4) Synthesis scheme for 3-(2,6-difluorophenyl)-1,2,4-thiadiazol-5-amine

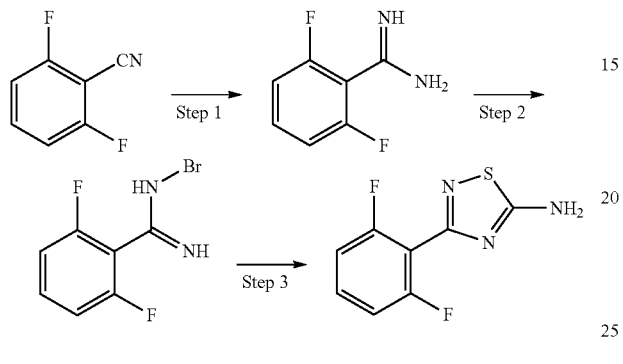

Step 1: Preparation of 2,6-difluorobenzenecarboximidamide

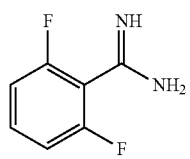

To a solution of 2,6-difluorobenzonitrile (20 g) in diethyl ether (200 mL) was added lithium bis(trimethylsilyl)amide (240 mL, 1M in THF) at 0° C. The reaction mixture was stirred overnight at room temperature. After that, methyl tert-butyl ether (150 mL) was added and the reaction was stirred for 10 min. The reaction mixture was diluted with water (50 mL) and extracted with ethyl acetate (2×50 mL). The aqueous layer was basified (pH: 12-14) and extracted with ethyl acetate (2×50 mL). The combined organic layer was dried over sodium sulphate and concentrated under reduced pressure to afford the title compound (16 g) as a white solid.

$^1$H-NMR (400.0 MHz, $d_6$-DMSO): δ=7.46-7.38 (m, 1H), 7.13-7.08 (m, 2H), 6.51 (s large, 3H).

Step 2: Preparation of N-bromo-2,6-difluorobenzenecarboximidamide

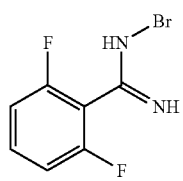 [SMILES: N=C(NBr)c1c(F)cccc1F]

To a solution of 2,6-difluorobenzenecarboximidamide (16 g) in carbon tetrachloride (160 mL), N-bromosuccinimide (18 g) was added at 0° C. and the reaction mixture was stirred for 1 hour. The reaction mixture was filtered through a pad of celite and the filtrate was concentrated under reduced pressure to afford the title compound (12 g) as a pale yellow solid.

HPLC-MS: mass (m/z): 235.0 (M+H)+

Step 3: Preparation of 3-(2,6-difluorophenyl)-1,2,4-thiadiazol-5-amine

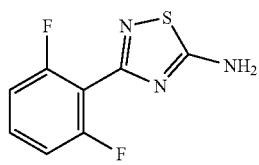 [SMILES: Nc1nc(-c2c(F)cccc2F)ns1]

To a solution of 2,6-difluorobenzenecarboximidamide (12 g) in methanol (120 mL) was added potassium thiocyanate (10 g) at 0° C. over a period of 10 minutes and the reaction mixture was stirred for 3 hours. Methanol was removed under reduced pressure. The residue was diluted with water (50 mL) and extracted with ethyl acetate (2×50 mL). The combined organic layer was dried over sodium sulphate and concentrated under reduced pressure. The crude compound was purified by column chromatography to afford the title compound (6.5 g) as a white solid.

HPLC-MS: mass (m/z): 214.0 (M+H)+

$^1$H-NMR (400.0 MHz, $d_6$-DMSO): δ=8.11 (s, 2H), 7.57-7.50 (m, 1H), 7.22-7.16 (m, 2H).

Synthesis Example 2

2-Bromo-N-[3-(2,6-difluorophenyl)-1,2,4-thiadiazol-5-yl]benzamide (Compound I-1-5 in Table 1)

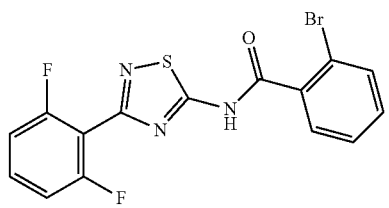 [SMILES: O=C(Nc1nc(-c2c(F)cccc2F)ns1)c1ccccc1Br]

3-(2,6-Difluorophenyl)-1,2,4-thiadiazol-5-amine (100 mg) was initially placed in tetrahydrofuran. Sodium hydride (20.63 mg) was added in portion and the reaction mixture was stirred at room temperature for one hour. 2-Bromobenzoyl chloride in tetrahydrofuran (113 mg) was added dropwise and the reaction mixture was stirred overnight at room temperature. The reaction was quenched with 1 mL of methanol. The residue was purified first by column chromatography on silica gel using the mobile phase cyclohexane/ethyl acetate followed by preparative HPLC. This afforded 102 mg of the title compound.

HPLC-MS: mass (m/z): 396.9

$^1$H-NMR (400.0 MHz, $d_6$-DMSO): see peak list for compound I-1-5 (Table 4)

Synthesis Example 3

2-Bromo-N-[3-(2-chlorophenyl)-1,2,4-thiadiazol-5-yl]benzamide (Compound I-1-21 in Table 1)

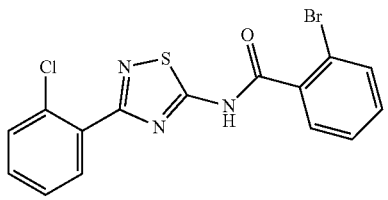 [SMILES: O=C(Nc1nc(-c2ccccc2Cl)ns1)c1ccccc1Br]

3-(2-Chlorophenyl)-1,2,4-thiadiazol-5-amine (150 mg) was placed in 2 mL of dichloromethane. Trimethylamine (359 mg) and 2-bromobenzoyl chloride (156 mg) in 1 mL of dichloromethane were added at 0° C. The reaction mixture was stirred overnight at room temperature. The reaction mixture was diluted with dichloromethane and washed with water. The organic phase was dried over sodium sulphate and evaporated. The residue obtained was purified by column chromatography on silica gel using the mobile phase cyclohexane/ethyl acetate (100%-0% to 0%-100%). This afforded 182 mg of the title compound.

HPLC-MS: mass (m/z): 393.9 (M+H)$^+$ $^1$H-NMR (400.0 MHz, CD3CN): see peak list for compound I-1-21 (Table 4)

Synthesis Example 4

2-Chloro-N-[3-(2,6-difluorophenyl)-1,2,4-thiadiazol-5-yl]nicotinamide (Compound I-1-29 in Table 1)

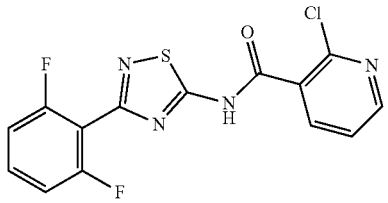 [SMILES: O=C(Nc1nc(-c2c(F)cccc2F)ns1)c1cccnc1Cl]

3-(2,6-Difluorophenyl)-1,2,4-thiadiazol-5-amine (100 mg) was placed in chloroform. Diisopropylethylamine (182 mg) was added. 2-Chloronicotinoyl chloride (99 mg) was added as well as 4-(N,N-dimethylamino)pyridine (0.6 mg). The reaction mixture was stirred at room temperature overnight. Some water was added. After extraction with dichloromethane the organic phase was dried over sodium sulfate and evaporated. The residue obtained was purified by silica gel chromatography with cyclohexane-ethylacetate as eluents. This afforded 118 mg of the title compound.

HPLC-MS: mass (m/z): 352.9 (M+H)$^+$ $^1$H-NMR (400.0 MHz, d6-DMSO): see peak list for compound I-1-29 (Table 4)

Synthesis Example 5

Sodium [3-(2,6-difluorophenyl)-1,2,4-thiadiazol-5-yl]{[2-(trifluoromethyl)pyridin-3-yl]carbonyl}azanide (Compound I-1-30 in Table 1)

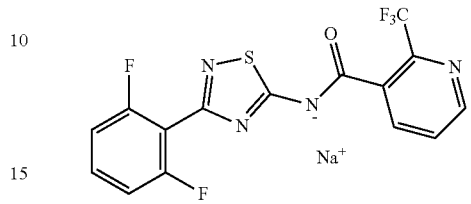

N-[3-(2,6-Difluorophenyl)-1,2,4-thiadiazol-5-yl]-2-(trifluoromethyl)nicotinamide (48 mg) was solubilized in 2 mL of methanol. One equivalent of sodium methoxide was added. The reaction mixture was stirred at room temperature for 1 hour. The reaction mixture was then evaporated leading to the title compound (50 mg).

HPLC-MS: mass (m/z): 386.0 ([M-Na$^+$+H$^+$]+H)$^+$ $^1$H-NMR (400.0 MHz, d$_6$-DMSO): see peak list for compound I-1-30 (Table 4)

Synthesis Example 6

N-[3-(2,6-Difluorophenyl)-1,2,4-thiadiazol-5-yl]-2-(trifluoromethyl)-N-{[2-(trifluoromethyl)pyridin-3-yl]carbonyl}nicotinamide (Compound I-1-31 in Table 1)

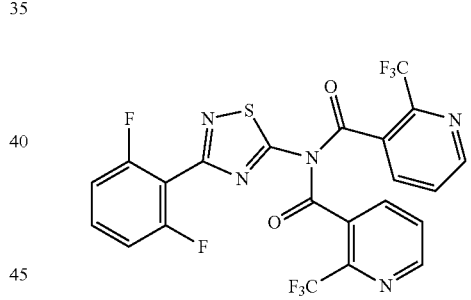

3-(2,6-Difluorophenyl)-1,2,4-thiadiazol-5-amine (1 equiv) was placed in chloroform. Diisopropylethylamine (3 equiv) was added. 2-(Trifluoromethyl)nicotinoyl chloride (1.2 equiv) and dimethylaminopyridine (0.01 equiv) were added at room temperature. The reaction mixture was stirred overnight at room temperature. Some water was added. After extraction with chloroform the organic phase was evaporated. The residue obtained was purified by silica gel chromatography and then by HPLC. This afforded the title compound (5.5% yield) as well as N-[3-(2,6-difluorophenyl)-1,2,4-thiadiazol-5-yl]-2-(trifluoromethyl)nicotinamide (compound I-1-6, 36% yield).

HPLC-MS: mass (m/z): 560.0 (M+H)$^+$ $^1$H-NMR (400.0 MHz, d6-DMSO): see peak list for compound I-1-31 (Table 4)

Compound I-1-6 was also be obtained by cleavage of compound I-1-31 in methanol using 10% sodium hydroxide with stirring at room temperature for 1 hour, followed by purification by preparative HPLC. Analytical data for compound I-1-6 are provided in Table 4.

Synthesis Example 7

N-[3-(2,6-Difluorophenyl)-1,2,4-thiadiazol-5-yl]-N-ethyl-2-(trifluoromethyl)nicotinamide (Compound I-1-34 in Table 1)

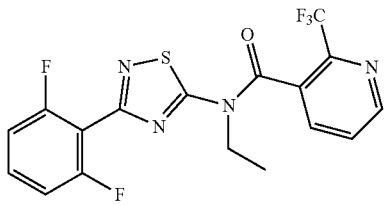 [SMILES: CCN(C(=O)c1cccnc1C(F)(F)F)c1nc(-c2c(F)cccc2F)ns1]

N-[3-(2,6-Difluorophenyl)-1,2,4-thiadiazol-5-yl]-2-(trifluoromethyl)nicotinamide (Compound I-1-6, 100 mg) was placed in 2 mL of dimethylformamide under argon. Sodium hydride (9 mg) was added and the reaction mixture was stirred at room temperature for 10 minutes. Ethyliodide (0.031 mL) was added and the reaction mixture was stirred overnight at room temperature. Purification by preparative HPC afforded 35.8 mg of the title compound.

HPLC-MS: mass (m/z): 415.1 (M+H)$^+$ $^1$H-NMR (400.0 MHz, d$_6$-DMSO): see peak list for compound I-1-34 (Table 4)

Synthesis Example 8

N-[3-(2,6-Difluorophenyl)-1,2,4-thiadiazol-5-yl]-2-ethylnicotinamide (Compound I-1-36 in Table 1)

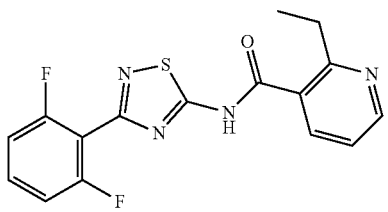 [SMILES: CCc1ncccc1C(=O)Nc1nc(-c2c(F)cccc2F)ns1]

To 2-ethylnicotinic acid (227 mg) in dimethylformamide was added 1-[bis(dimethylamino)methylene]-1H-1,2,3-triazolo[4,5-b]pyridinium 3-oxid hexafluorophosphate) (HATU) (571 mg) and diisopropylethylamine (364 mg). The reaction mixture was stirred at room temperature for 15 minutes. 3-(2,6-difluorophenyl)-1,2,4-thiadiazol-5-amine (200 mg) and 4-(N,N-dimethylamino)pyridine (11 mg) were added. The reaction was heated at 80° C. and stirred overnight. HPLC purification afforded 188 mg of the title compound.

HPLC-MS: mass (m/z): 347.1 (M+H)$^+$ $^1$H-NMR (400.0 MHz, d$_6$-DMSO): see peak list for compound I-1-36 (Table 4)

Synthesis Example 9

N-{3-[2-(Trifluoromethoxy)phenyl]-1,2,4-thiadiazol-5-yl}-2-(trifluoromethyl)nicotinamide (Compound I-1-55 in Table 1)

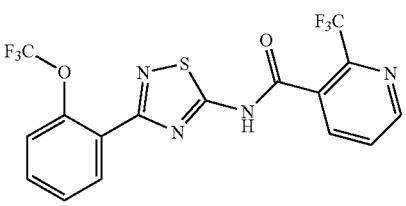

N-(3-Bromo-1,2,4-thiadiazol-5-yl)-2-(trifluoromethyl)nicotinamide (100 mg), [2-(trifluoromethoxy)phenyl]boronic acid (175 mg), potassium phosphate (112 mg) and X-Phos aminobiphenyl palladium chloride precatalyst (22 mg) were placed in a mixture of degassed tetrahydrofuran/water (2 mL/0.2 mL). The reaction mixture was heated at 60° C. overnight. After cooling down and purification by preparative HPLC, 73.5 mg of the title compound were obtained.

HPLC-MS: mass (m/z): 435.0 (M+H)$^+$ $^1$H-NMR (400.0 MHz, d$_6$-DMSO): see peak list for compound I-1-55 (Table 4)

Synthesis scheme for N-(3-bromo-1,2,4-thiadiazol-5-yl)-2-(trifluoromethyl)nicotinamide

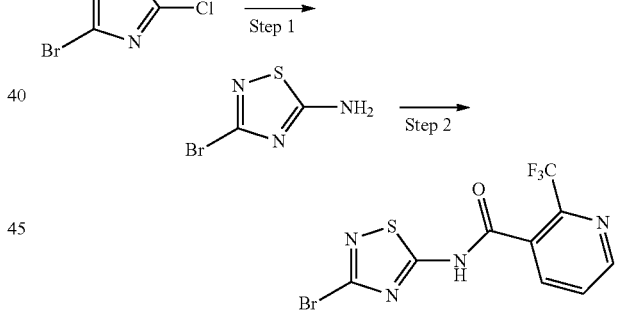

Step 1: Preparation of 3-bromo-1,2,4-thiadiazol-5-amine

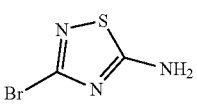

To a solution of 3-bromo-5-chloro-1,2,4-thiadiazole (5 g) in ethanol (15 mL) was added an aqueous ammonia solution (26%, 2 equiv). The reaction mixture was heated at 70° C. for 3 hours. It was then cooled down and an aqueous solution of sodium hydrogenecarbonate was added. The precipitate was filtered off, washed with water and dried. This afforded 2.88 g of the title compound.

HPLC-MS: mass (m/z): 182.0
$^1$H-NMR (400.0 MHz, d$_6$-DMSO): 8.37 (br s, 2H)

Preparation of N-(3-bromo-1,2,4-thiadiazol-5-yl)-2-(trifluoromethyl)nicotinamide

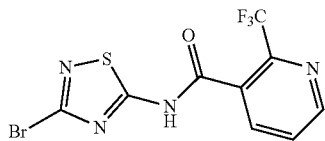 [SMILES: O=C(Nc1nc(Br)ns1)c1cccnc1C(F)(F)F]

To 2-(trifluoromethyl)nicotinamide (11.9 g) in dimethylformamide (97 mL) was added 1-[bis(dimethylamino)methylene]-1H-1,2,3-triazolo[4,5-b]pyridinium 3-oxid hexafluorophosphate) (HATU) (23.7 g) and diisopropylethylamine (20.3 mL). The reaction mixture was stirred at room temperature for 15 minutes. 3-bromo-1,2,4-thiadiazol-5-amine (7 g) and 4-(N,N-dimethyl)aminopyridine (475 mg) were added. The reaction was heated at 80° C. and stirred overnight.

A solution of aqueous monosodium phosphate (5%) was added. The reaction mixture was extracted 4 times with chloroform. The organic phases were combined, dried and evaporated. The residue obtained was purified by column chromatography on silica gel using the mobile phase cyclohexane/acetone. This afforded 5.12 g of the title compound.

HPLC-MS: mass (m/z): 352.9; 354.9
$^1$H-NMR (400.0 MHz, d$_6$-DMSO): δ=14.20 (s, 1H), 8.96 (d, 1H), 8.41 (d, 1H), 7.96 (dd, 1H)

Synthesis Example 10

N-{3-[2-(trifluoromethoxy)phenyl]-1,2,4-thiadiazol-5-yl}-2-(trifluoromethyl)benzamide

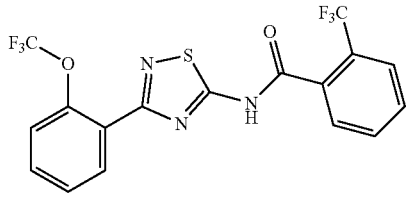 [SMILES: O=C(Nc1nc(-c2ccccc2OC(F)(F)F)ns1)c1ccccc1C(F)(F)F]

N-{3-[2-(Trifluoromethoxy)phenyl]-1,2,4-thiadiazol-5-yl}-2-(trifluoromethyl)benzamide was obtained analogously to synthesis example 9 starting with N-(3-bromo-1,2,4-thiadiazol-5-yl)-2-(trifluoromethyl)benzamide.

HPLC-MS: mass (m/z): 434.0 (M+H)$^+$
$^1$H-NMR (400.0 MHz, d$_6$-DMSO): see peak list for compound I-1-70 (Table 4)

Preparation of N-{3-[2-(trifluoromethoxy)phenyl]-1,2,4-thiadiazol-5-yl}-2-(trifluoromethyl)benzamide

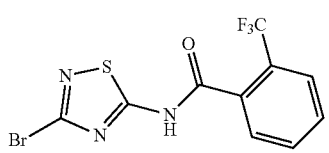 [SMILES: O=C(Nc1nc(Br)ns1)c1ccccc1C(F)(F)F]

N-(3-Bromo-1,2,4-thiadiazol-5-yl)-2-(trifluoromethyl)benzamide (4.3 g) was obtained analogously to synthesis example 9 starting with 2-(trifluoromethyl)benzoic acid (6.1 g) and 3-bromo-1,2,4-thiadiazol-5-amine (3.6 g).

HPLC-MS: mass (m/z): 353.9
$^1$H-NMR (400.0 MHz, d$_6$-DMSO): δ=14.06 (s, 1H), 7.95 (d, 1H), 7.89 (m, 3H)

Synthesis Example 11

N-{3-[2-Chloro-3-(trifluoromethyl)phenyl]-1,2,4-thiadiazol-5-yl}-2-(trifluoromethyl)nicotinamide (Compound I-1-62 in Table 1)

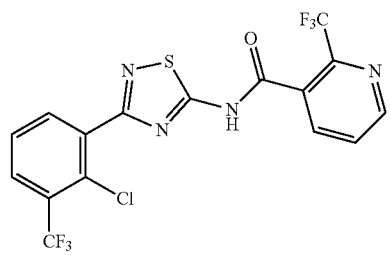 [SMILES: O=C(Nc1nc(-c2cccc(C(F)(F)F)c2Cl)ns1)c1cccnc1C(F)(F)F]

To the mixture of N-[3-(2-chlorophenyl)-1,2,4-thiadiazol-5-yl]-2-(trifluoromethyl)nicotinamide (Compound I-1-43, 100 mg), sodium trifluoromethanesulfinate (487 mg) and copper (II) triflate (38 mg), under argon, was added acetonitrile (5 mL). To the resulting mixture, at vigorous stirring, was added tert-butylhydroperoxide (0.75 mL, 70 wt. % in H$_2$O) over 1 hour by a syringe pump. After stirring for additional 12 hours the reaction mixture was filtered. The resulting filtrate was concentrated to ca. 2 mL. Preparative HPLC separation afforded 11 mg of the title compound.

HPLC-MS: mass (m/z): 453.0 (M+H)$^+$
$^1$H-NMR (400.0 MHz, d$_6$-DMSO): 14.1 (bs, 1H), 9.0 (dd, 4.8, 1H), 8.4 (dd, 8.0, 1H), 8.1 (dd, 1H), 8.0 (dd, 1H), 7.9 (dd, 1H), 7.7 (m, 1H).

Synthesis Example 12

N-{3-[2,6-Bis(trifluoromethyl)phenyl]-1,2,4-thiadiazol-5-yl}-2-(trifluoromethyl)nicotinamide (Compound I-1-65 in Table 1)

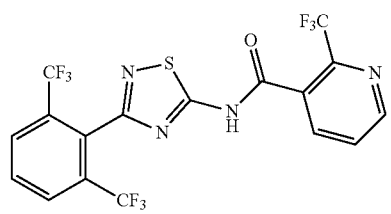 [SMILES: O=C(Nc1nc(-c2c(C(F)(F)F)cccc2C(F)(F)F)ns1)c1cccnc1C(F)(F)F]

To the mixture of 2-(trifluoromethyl)-N-{3-[2-(trifluoromethyl)phenyl]-1,2,4-thiadiazol-5-yl}nicotinamide (Compound I-1-20, 70 mg), sodium trifluoromethanesulfinate (313 mg) and copper (II) triflate (18 mg), under argon, was added acetonitrile (2 mL). To the resulting mixture, at vigorous stirring, was added tert-butylhydroperoxide (0.28 mL, 70 wt. % in H$_2$O) over 30 minutes by a syringe pump. The reaction mixture was stirred for 18 hours and then additional sodium trifluoromethanesulfinate (313 mg) and tert-butylhydroperoxide (0.28 mL, 70 wt. % in H$_2$O) were added. After stirring for additional 15 hours the reaction mixture was filtered. The resulting filtrate was concentrated to ca. 1 mL. Preparative HPLC separation afforded 1 mg of the title compound.

HPLC-MS: mass (m/z): 487.1 (M+H)$^+$ $^1$H-NMR (400.0 MHz, d$_6$-DMSO): 14.07 (bs, 1H), 8.96 (d, 1H), 8.49 (d, 1H), 8.28 (d, 2H), 8.03 (t, 1H), 7.93 (dd, 1H).

N-{3-[2,4-Bis(trifluoromethyl)phenyl]-1,2,4-thiadiazol-5-yl}-2-(trifluoromethyl)nicotinamide (Compound I-1-66 in Table 1)

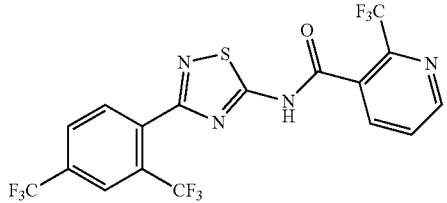 [SMILES: O=C(Nc1nc(-c2ccc(C(F)(F)F)cc2C(F)(F)F)ns1)c1cccnc1C(F)(F)F]

This compound (2 mg) was also isolated from the previous reaction transforming compound Compound I-1-20 into compound I-1-65 and compound I-1-66.

HPLC-MS: mass (m/z): 487.1 (M+H)$^+$ $^1$H-NMR (400.0 MHz, d$_6$-DMSO): 14.09 (bs, 1H), 8.97 (d, 4.8 Hz, 1H), 8.45 (d, 7.9 Hz, 1H), 8.24-8.27 (m, 2H), 8.15 (d, 8.4 Hz, 1H), 7.94 (dd, 7.9, 4.8 Hz, 1H).

Synthesis Example 13

N-[3-(2-Cyanophenyl)-1,2,4-thiadiazol-5-yl]-2-(trifluoromethyl)nicotinamide (Compound I-1-67 in Table 1)

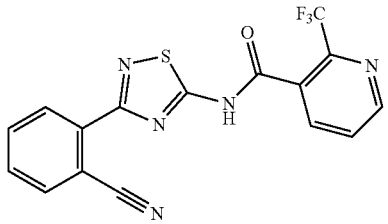 [SMILES: N#Cc1ccccc1-c1nsc(NC(=O)c2cccnc2C(F)(F)F)n1]

To a mixture of N-(3-phenyl-1,2,4-thiadiazol-5-yl)-2-(trifluoromethyl)nicotinamide (100 mg, compound obtained by amide coupling with the corresponding amine) in a 5 ml crimp sealable flask, N-iodosuccinimide (141 mg), Pd (OAc)$_2$, (24 mg) and acetonitrile (2 ml) were added. The mixture was heated in a sealed flask (5 mL) at 110° C. overnight. At room temperature a 10% aqueous solution of Na$_2$SO$_3$ (25 mL) was added, the resulting suspension was extracted with dichloromethane (3×50 mL), the organic phases combined, filtered through a water repellant filter and the solvent removed under reduced pressure. The crude material was taken up in dimethylsulfoxide (2 ml) and transferred to a 5 ml crimp sealable flask. Copper (I) cyanide (32 mg) was added and the mixture heated at 140° C. for 1 hour. Water (20 ml) was added, and the resulting precipitate collected by filtration. Further purification was performed using preparative HPLC, affording the title compound as a white solid (10.1 mg).

HPLC-MS: mass (m/z): 376.0 (M+H)$^+$ $^1$H-NMR (400.0 MHz, CD$_3$OD): 9.0 (d, 1H), 8.4 (d, 1H), 8.3 (dd, 1H), 8.0 (dd, 1H), 7.9 (dd, 1H), 7.9 (dt, 1H), 7.7 (dt, 1H).

N-[3-(2,6-Dicyanophenyl)-1,2,4-thiadiazol-5-yl]-2-(trifluoromethyl)nicotinamide (Compound I-1-78 in Table 1)

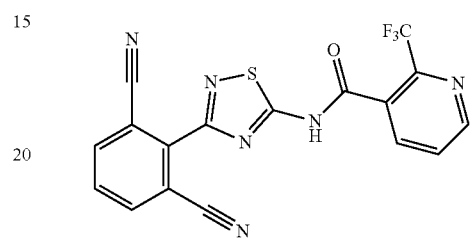

Compound I-1-78 was obtained as a second product in the previous reaction transforming N-(3-phenyl-1,2,4-thiadiazol-5-yl)-2-(trifluoromethyl)nicotinamide (100 mg) into compound I-1-67 (mono-nitrile) and compound I-1-78 (bis-nitrile). It was obtained after purification by preparative HPLC (4 mg).

HPLC-MS: mass (m/z): 401.1 (M+H)$^+$ $^1$H-NMR (400.0 MHz, CD$_3$OD): 8.9 (dd, 1H), 8.3 (dd, 1H), 8.2 (d, 2H), 7.8 (m, 2H)

Synthesis Example 14

N-{3-[3-Chloro-5-(trifluoromethyl)pyridin-2-yl]-1,2,4-thiadiazol-5-yl}-2-(trifluoromethyl)nicotinamide (Compound I-2-3 in Table 2)

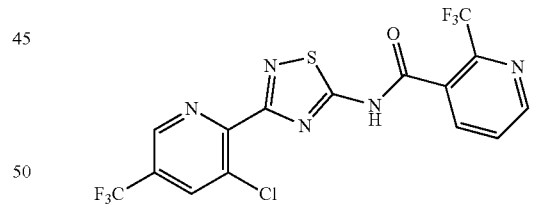

2-(Trifluoromethyl)nicotinic acid (168 mg), bromo-tris-pyrrolidino phosphoniumhexafluorophosphate (513 mg) and 3-[3-chloro-5-(trifluoromethyl)pyridin-2-yl]-1,2,4-thiadiazol-5-amine (206 mg) and diisopropylethylamine (189 mg) were placed in dichloromethane (7 mL). The reaction mixture was stirred overnight at room temperature. Some water was added. After extraction with dichloromethane the organic phase was dried and evaporated. The residue obtained was purified first by silica gel chromatography and then by preparative HPLC. This afforded 65 mg of the title compound.

HPLC-MS: mass (m/z): 353.9 (M+H)$^+$ $^1$H-NMR (400.0 MHz, d6-DMSO): see peak list for compound I-2-3 (Table 2)

Synthesis Example 15

2-Chloro-N-[3-(3-chloropyridin-2-yl)-1,2,4-thiadiazol-5-yl]benzamide (Compound I-2-6 in Table 2)

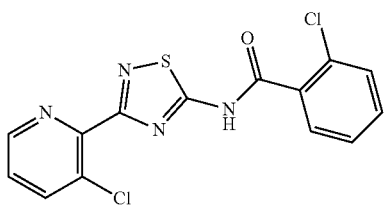 [SMILES: O=C(Nc1nc(-c2ncccc2Cl)ns1)c1ccccc1Cl]

Compound I-2-6 (66 mg) was obtained analogously to compound I-1-21 using diisopropylethylamine as a base and the appropriate starting thiadiazol-amine adduct.

HPLC-MS: mass (m/z): 351.0, 352.9

¹H-NMR (400.0 MHz, d6-DMSO): 13.82 (s, 1H), 8.67 (d, 1H), 8.15 (d, 1H), 7.79 (d, 1H), 7.65-7.59 (m, 3H), 7.52 (t, 1H).

Synthesis scheme for 3-(3-chloropyridin-2-yl)-1,2,4-thiadiazol-5-amine

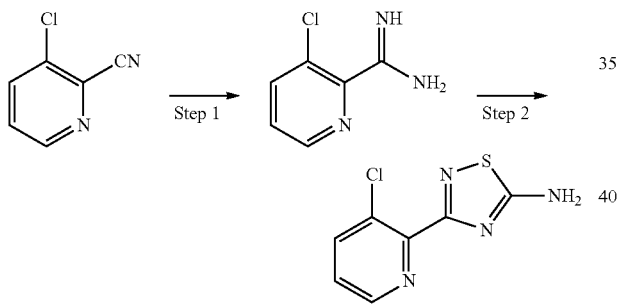

Step 1: Preparation of 3-chloropyridine-2-carboximidamide

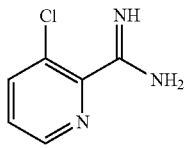

To a solution of ammonium chloride (7.70 g) in toluene (200 mL) a solution of trimethylaluminium in 2M in hexane (20.8 g, 144 mmol) was added dropwise at 0° C. and the mixture was stirred for 30 minutes. 3-chloropyridine-2-carbonitrile (10.0 g) was then added. The reaction was heated to 80° C. and stirred at this temperature until gas evolution stopped. After completion of the reaction, the reaction mixture was cooled to 0° C., quenched with methanol (10 mL), and filtered through a pad of silica gel.

The filtrate was evaporated under reduced pressure. This afforded 8.43 g of the title compound.

Step 2: Preparation of 3-(3-chloropyridin-2-yl)-1,2,4-thiadiazol-5-amine

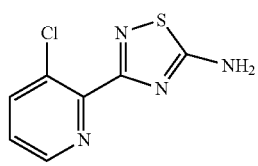 [SMILES: Nc1nc(-c2ncccc2Cl)ns1]

At 0° C. trimethylamine (10.7 g) was added to a solution of 3-chloropyridine-2-carboximidamide (5.50 g) in methanol (100 mL) followed by dropwise addition of bromine (5.64 g). The reaction mixture was stirred for 30 minutes at 0° C. before potassium thiocyanate (3.77 g) was added. The reaction was stirred overnight at room temperature and then evaporated under reduced pressure. The residue was washed with water, dried in air, and re-crystallized from acetonitrile to obtain 3.15 g of the title compound.

Synthesis Example 16

N-[3-(2-Chloropyridin-3-yl)-1,2,4-thiadiazol-5-yl]-2-(trifluoromethyl)benzamide (Compound I-3-1 in Table 3)

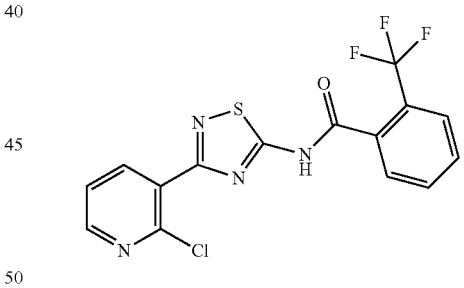

Compound I-3-1 (17 mg) was obtained analogously to compound compound I-1-36 (Synthetic Example 8) using the appropriate starting thiadiazol-amine (100 mg).

HPLC-MS: mass (m/z): 385.0 (M+H)⁺

¹H-NMR (400.0 MHz, d6-DMSO): see peak list for compound I-3-1 (Table 3)

The appropriate thiadiazol-amine adduct was obtained analogously to 3-(3-chloropyridin-2-yl)-1,2,4-thiadiazol-5-amine using the 2 steps protocole previously described in Synthetic Example 15, starting with 2-chloronicotinonitrile.

The compounds of formulae (I-1), (1-2) and (1-3) described in Tables 1, 2 and 3 are likewise preferred compounds which were obtained according to or analogously to the Synthesis Examples described above.

TABLE 1

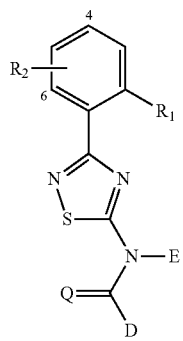

(I-1)

| Compound No. | D | E | $R_1$ | $R_2$ | Q |
|---|---|---|---|---|---|
| I-1-1 Synthesis Example 1 | 2,6-difluorophenyl | H | F | 6-F | O |
| I-1-2 | 2-fluorophenyl | H | F | 6-F | O |
| I-1-3 | 2-chlorophenyl | H | F | 6-F | O |
| I-1-4 | 2-trifluoromethyl phenyl | H | F | 6-F | O |
| I-1-5 Synthesis Example 2 | 2-bromophenyl | H | F | 6-F | O |
| I-1-6 | 3-(2-trifluoromethyl) pyridinyl | H | F | 6-F | O |
| I-1-7 | 3-(2-trifluoromethyl) pyrazinyl | H | F | 6-F | O |
| I-1-8 | 2-iodophenyl | H | F | 6-F | O |
| I-1-9 | 2-difluoromethyl phenyl | H | F | 6-F | O |
| I-1-10 | 2-nitrophenyl | H | F | 6-F | O |
| I-1-11 | 2-trifluoromethyl-3-fluorophenyl | H | F | 6-F | O |
| I-1-12 | 2-trifluoromethyl-6-fluorophenyl | H | F | 6-F | O |
| I-1-13 | 2-(3-trifluoromethyl) pyridinyl | H | F | 6-F | O |
| I-1-14 | 3-(2-difluoromethyl) pyridinyl | H | F | 6-F | O |
| I-1-15 | 2,6-difluorophenyl | H | $CF_3$ | H | O |
| I-1-16 | 2-bromophenyl | H | $CF_3$ | H | O |
| I-1-17 | 2-chlorophenyl | H | $CF_3$ | H | O |
| I-1-18 | 2-trifluoromethyl phenyl | H | $CF_3$ | H | O |
| I-1-19 | 2-(3-trifluoromethyl) pyridinyl | H | $CF_3$ | H | O |
| I-1-20 | 3-(2-trifluoromethyl) pyridinyl | H | $CF_3$ | H | O |
| I-1-21 Synthesis Example 3 | 2-bromophenyl | H | Cl | H | O |
| I-1-22 | 2-chlorophenyl | H | Cl | H | O |
| I-1-23 | 2-trifluoromethyl phenyl | H | Cl | H | O |
| I-1-24 | 2-(3-chloro)pyridinyl | H | Cl | H | O |
| I-1-25 | 2-fluorophenyl | H | Cl | H | O |
| I-1-26 | 2-iodophenyl | H | Cl | H | O |
| I-1-27 | 2-trifluoromethyl-6-fluorophenyl | H | Cl | H | O |
| I-1-28 | 2-fluorophenyl | H | CN | H | O |
| I-1-29 Synthesis Example 4 | 3-(2-chloro) pyridinyl | H | F | 6-F | O |
| I-1-30 Synthesis Example 5 | 3-(2-trifluoromethyl) pyridinyl | Na | F | 6-F | O |
| I-1-31 Synthesis Example 6 | 3-(2-trifluoromethyl) pyridinyl | CO-3-(2-$CF_3$) pyridinyl | F | 6-F | O |
| I-1-32 | 3,5-(2-trifluoromethyl) pyrimidinyl | H | F | 6-F | O |
| I-1-33 | 3-(2-methoxy) pyridinyl | H | F | 6-F | O |

TABLE 1-continued (I-1)

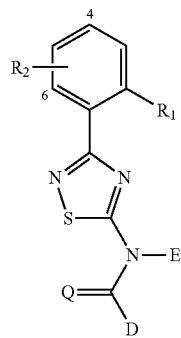

| Compound No. | D | E | $R_1$ | $R_2$ | Q |
|---|---|---|---|---|---|
| I-1-34 Synthesis Example 7 | 3-(2-trifluoromethyl) pyridinyl | Et | F | 6-F | O |
| I-1-35 | 2-(trifluoromethyl)-4,5-dihydro-3,6-oxathiinyl | H | F | 6-F | O |
| I-1-36 Synthesis Example 8 | 3-(2-ethyl) pyridinyl | H | F | 6-F | O |
| I-1-37 | 3-(2-pentafluoroethyl) pyridinyl | H | F | 6-F | O |
| I-1-38 | 2-(2,2,2-trifluoroethyl)-3-pyridinyl | H | F | 6-F | O |
| I-1-39 | 2-(difluoromethyl)-4,5-dihydro-3,6-oxathiinyl | H | F | 6-F | O |
| I-1-40 | 3-(2-methyl) pyrazinyl | H | F | 6-F | O |
| I-1-41 | 2-methylphenyl | H | Cl | H | O |
| I-1-42 | 3-(2-chloro) pyridinyl | H | Cl | H | O |
| I-1-43 | 3-(2-trifluoromethyl) pyridinyl | H | Cl | H | O |
| I-1-44 | 3-(2-trifluoromethyl) pyrazinyl | H | Cl | H | O |
| I-1-45 | 3-(2-methoxy) pyridinyl | H | Cl | H | O |
| I-1-46 | 3-(2-pentafluoroethyl) pyridinyl | H | Cl | H | O |
| I-1-47 | 2-(2,2,2-trifluoroethyl)-3-pyridinyl | H | Cl | H | O |
| I-1-48 | 3-(ethyl) pyridinyl | H | Cl | H | O |
| I-1-49 | 2-(methyl)-4,5-dihydro-3,6-oxathiinyl | H | $CF_3$ | H | O |
| I-1-50 | 3,6-(2-trifluoromethyl) pyrazinyl | H | $CF_3$ | H | O |
| I-1-51 | 3-(2-chloro) pyridinyl | H | $CF_3$ | H | O |
| I-1-52 | 3-(2-pentafluoroethyl) pyridinyl | H | $CF_3$ | H | O |
| I-1-53 | 3-(2-trifluoromethyl) pyridinyl | H | $CH_3$ | H | O |
| I-1-54 | 3-(2-trifluoromethyl) pyridinyl | H | $OCH_3$ | H | O |

TABLE 1-continued

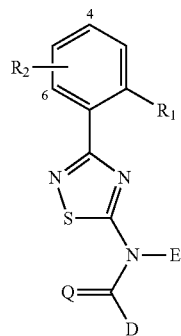

(I-1)

| Compound No. | D | E | R₁ | R₂ | Q |
|---|---|---|---|---|---|
| I-1-55 Synthesis Example 9 | 3-(2-trifluoromethyl)pyridinyl | H | OCF₃ | H | O |
| I-1-56 | 3-(2-trifluoromethyl)pyridinyl | H | F | 4-F | O |
| I-1-57 | 3-(2-trifluoromethyl)pyridinyl | H | F | H | O |
| I-1-58 | 3-(2-trifluoromethyl)pyridinyl | H | C₂H₅ | H | O |
| I-1-58 | 3-(2-trifluoromethyl)pyridinyl | H | C₂H₅ | H | O |
| I-1-59 | 3-(2-trifluoromethyl)pyridinyl | H | CH(CH₃)₂ | H | O |
| I-1-60 | 3-(2-trifluoromethyl)pyridinyl | H | CF₃ | 4-F | O |
| I-1-61 | 3-(2-trifluoromethyl)pyridinyl | H | CF₃ | 3-F | O |
| I-1-62 Synthesis Example 11 | 3-(2-trifluoromethyl)pyridinyl | H | Cl | 3-CF₃ | O |
| I-1-63 | 3-(2-trifluoromethyl)pyridinyl | H | Cl | 6-Cl | O |
| I-1-64 | 3-(2-trifluoromethyl)pyridinyl | H | CF₃ | 5-F | O |
| I-1-65 Synthesis Example 12 | 3-(2-trifluoromethyl)pyridinyl | H | CF₃ | 6-CF₃ | O |
| I-1-66 Synthesis Example 12 | 3-(2-trifluoromethyl)pyridinyl | H | CF₃ | 4-CF₃ | O |
| I-1-67 Synthesis Example 13 | 3-(2-trifluoromethyl)pyridinyl | H | CN | H | O |
| I-1-68 | 2-trifluoromethyl phenyl | H | CH₃ | H | O |
| I-1-69 | 2-trifluoromethyl phenyl | H | CF₃ | 5-F | O |
| I-1-70 Synthesis Example 10 | 2-trifluoromethyl phenyl | H | OCF₃ | H | O |
| I-1-71 | 2-trifluoromethyl phenyl | H | F | 4-F | O |
| I-1-72 | 2-trifluoromethyl phenyl | H | OCH₃ | H | O |

TABLE 1-continued

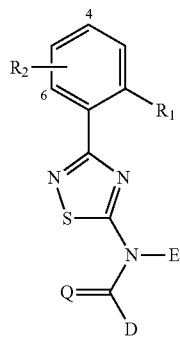

(I-1)

| Compound No. | D | E | R₁ | R₂ | Q |
|---|---|---|---|---|---|
| I-1-73 | 2-trifluoromethyl phenyl | H | F | H | O |
| I-1-74 | 2-trifluoromethyl phenyl | H | CH(CH₃)₂ | H | O |
| I-1-75 | 2-trifluoromethyl phenyl | H | CF₃ | 4-F | O |
| I-1-76 | 2-trifluoromethyl phenyl | H | CF₃ | 3-F | O |
| I-1-77 | 2-trifluoromethyl-3-chloro phenyl | H | F | 6-F | O |
| I-1-78 Synthesis Example 13 | 3-(2-trifluoromethyl) pyridinyl | H | CN | 6-CN | O |

TABLE 2

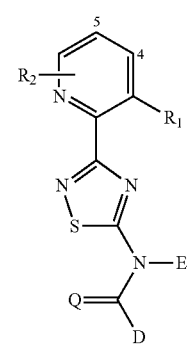

(I-2)

| Compound No. | D | E | R₁ | R₂ | Q |
|---|---|---|---|---|---|
| I-2-1 | 2-fluorophenyl | H | Cl | 5-CF₃ | O |
| I-2-2 | 2-trifluoromethyl phenyl | H | Cl | 5-CF₃ | O |
| I-2-3 Synthesis Example 14 | 3-(2-trifluoromethyl) pyridinyl | H | Cl | 5-CF₃ | O |
| I-2-4 | 2-trifluoromethyl phenyl | H | Cl | H | O |
| I-2-5 | 3-(2-trifluoromethyl) pyridinyl | H | Cl | H | O |
| I-2-6 Synthesis Example 15 | 2-chloro phenyl | H | Cl | H | O |
| I-2-7 | 3-(2-trifluoromethyl) pyridinyl | H | F | 5-F | O |

TABLE 3

(I-3)

| Compound No. | D | E | R₁ | R₂ | Q |
|---|---|---|---|---|---|
| I-3-1 | 2-trifluoromethyl phenyl | H | Cl | H | O |
| I-3-2 | 3-(2-trifluoromethyl) pyridinyl | H | Cl | H | O |
| I-3-3 | 3-(2-chloro) pyridinyl | H | Cl | H | O |
| I-3-4 | | H | Cl | H | O |
| I-3-5 | 2-iodo phenyl | H | Cl | H | O |

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$(intensity$_1$);$\delta_2$(intensity$_2$); ... ;
$\delta_i$(intensity$_i$); ... ;S$_n$(intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

TABLE 4

Example I-1-1:
HPLC-MS: mass (m/z): 354.0 (M + H)$^+$
$^1$H-NMR(400.0 MHz, d$_6$-DMSO): δ = 14.136(5.3); 8.316(0.4); 7.758(0.7); 7.738(2.0); 7.721(3.1); 7.701(2.1); 7.682(2.0); 7.666(2.8); 7.661(2.6); 7.645(5.2); 7.628(2.9); 7.624(3.1); 7.607(1.5); 7.358(5.9); 7.337(10.9); 7.320(11.6); 7.307(3.3); 7.300(16.0); 7.279(7.7); 7.270(1.9); 7.249(1.0); 7.228(0.5); 4.038(0.5); 4.021(0.4); 3.329(329.8); 2.681(0.6); 2.676(1.3); 2.672(1.7); 2.667(1.3); 2.663(0.6); 2.525(5.9); 2.512(100.3); 2.507(197.4); 2.503(257.0); 2.498(183.8); 2.494(87.3); 2.339(0.6); 2.334(1.3); 2.330(1.7); 2.325(1.2); 2.321(0.6); 1.989(1.7); 1.398(6.1); 1.253(0.7); 1.193(0.5); 1.175(1.0); 1.158(0.5); 1.122(0.4); 0.146(0.6); 0.008(4.8); 0.000(129.8); −0.009(4.3); −0.150(0.5)

Example I-1-2:
HPLC-MS: mass (m/z): 336.0 (M + H)$^+$
$^1$H-NMR(400.0 MHz, d$_6$-DMSO): δ = 13.744(4.1); 7.894(2.7); 7.889(3.0); 7.875(5.4); 7.871(5.7); 7.856(3.1); 7.852(3.1); 7.736(1.3); 7.731(1.3); 7.723(1.5); 7.717(3.0); 7.714(2.7); 7.697(3.2); 7.692(1.8); 7.683(1.8); 7.678(2.7); 7.662(2.8); 7.657(2.6); 7.645(1.9); 7.641(5.3); 7.636(1.9); 7.624(2.7); 7.620(3.1); 7.603(1.5); 7.455(4.1); 7.434(3.7); 7.429(4.7); 7.419(5.1); 7.408(4.0); 7.400(8.4); 7.381(3.8); 7.324(1.6); 7.317(9.5); 7.303(2.0); 7.296(16.0); 7.289(2.2); 7.276(7.8); 7.268(1.6); 3.333(268.7); 2.676(0.9); 2.672(1.2); 2.667(0.9); 2.525(3.8); 2.512(72.5); 2.507(142.4); 2.503(185.4); 2.498(133.3); 2.494(64.0); 2.334(0.9); 2.330(1.2); 2.325(0.9); 1.397(0.5); 1.176(0.4); 0.146(0.4); 0.008(3.0); 0.000(77.8); −0.009(2.6); −0.150(0.4)

Example I-1-3:
HPLC-MS: mass (m/z): 352.0 (M + H)$^+$
$^1$H-NMR(400.0 MHz, d$_6$-DMSO): δ = 13.845(1.1); 7.788(1.1); 7.785(1.1); 7.769(1.4); 7.765(1.4); 7.660(0.6); 7.654(0.8); 7.634(1.9); 7.630(2.0); 7.617(0.7); 7.608(0.9); 7.587(0.4); 7.537(0.7); 7.533(0.7); 7.518(1.0); 7.515(1.0); 7.501(0.5); 7.497(0.5); 7.321(0.3); 7.314(1.8); 7.300(0.5); 7.293(3.0); 7.273(1.5); 3.331(115.1); 3.328(118.2); 2.676(0.5); 2.671(0.7); 2.667(0.5); 2.524(2.4); 2.519(3.8); 2.511(41.7); 2.507(83.0); 2.502(108.5); 2.497(77.0); 2.493(35.9); 2.333(0.5); 2.329(0.7); 2.324(0.5); 1.989(0.8); 1.398(16.0); 1.175(0.5); 0.008(2.1); 0.000(58.1); −0.009(1.7)

Example I-1-4:
HPLC-MS: mass (m/z): 386.0 (M + H)$^+$
$^1$H-NMR(400.0 MHz, d$_6$-DMSO): δ = 13.953(8.1); 7.948(4.9); 7.931(10.7); 7.913(7.3); 7.879(2.8); 7.863(6.1); 7.840(6.0); 7.818(4.7); 7.799(1.5); 7.679(1.3); 7.663(2.7); 7.658(2.6); 7.642(5.2); 7.626(2.8); 7.621(3.1); 7.605(1.4); 7.325(1.7); 7.318(9.4); 7.297(16.0); 7.277(7.9); 7.269(1.6); 3.324(37.2); 2.676(0.7); 2.672(1.0); 2.667(0.8); 2.542(1.7); 2.507(115.8); 2.502(151.6); 2.498(112.5); 2.334(0.7); 2.329(1.0); 2.325(0.7); 2.087(6.1); 0.008(2.4); 0.000(60.5); −0.009(2.7)

Example I-1-5:
HPLC-MS: mass (m/z): 396.9
$^1$H-NMR(400.0 MHz, d$_6$-DMSO): δ = 13.832(7.0); 7.806(6.2); 7.803(5.2); 7.787(7.7); 7.783(7.0); 7.756(5.6); 7.751(6.6); 7.737(5.7); 7.732(7.0); 7.679(1.4); 7.663(2.9); 7.658(2.6); 7.646(2.0); 7.642(5.7); 7.637(2.0); 7.625(2.7); 7.620(3.2); 7.604(1.5); 7.581(2.3); 7.578(2.8); 7.562(6.9); 7.559(6.9); 7.544(7.4); 7.542(8.1); 7.537(6.7); 7.523(6.2); 7.518(6.0); 7.504(2.4); 7.499(1.9); 7.327(1.2); 7.324(1.6); 7.316(9.8); 7.303(2.1); 7.296(16.0); 7.289(2.2); 7.275(8.0); 7.267(1.4); 3.326(14.3); 3.176(1.5); 3.165(1.4); 2.677(0.4); 2.672(0.5); 2.668(0.3); 2.525(1.4); 2.512(28.2); 2.508(56.1); 2.503(73.1); 2.499(52.2); 2.494(24.7); 2.334(0.4); 2.330(0.5); 2.326(0.3); 0.146(0.3); 0.008(2.9); 0.000(75.0); −0.009(2.6); −0.150(0.3)

Example I-1-6:
HPLC-MS: mass (m/z): 387.0 (M + H)$^+$
$^1$H-NMR(400.0 MHz, d$_6$-DMSO): δ = 14.085(6.7); 8.959(6.2); 8.947(6.1); 8.450(5.8); 8.430(6.2); 7.952(5.0); 7.940(5.1); 7.932(4.9); 7.920(4.6); 7.684(1.3); 7.668(2.8); 7.663(2.7); 7.652(2.1); 7.647(5.4); 7.631(2.8); 7.626(3.2); 7.610(1.4); 7.329(1.9); 7.322(9.4); 7.301(16.0); 7.281(7.8); 7.273(1.7); 3.326(21.4); 2.678(0.4); 2.674(0.5); 2.669(0.4); 2.509(60.9); 2.504(79.3); 2.500(59.6); 2.336(0.4); 2.331(0.5); 2.327(0.4); 2.076(1.0); 0.008(0.5); 0.000(10.0); −0.008(0.5)

TABLE 4-continued

Example I-1-7:
HPLC-MS: mass (m/z): 388.0 (M + H)+
$^1$H-NMR(400.0 MHz, $d_6$-DMSO): δ = 19.989(0.4); 14.289(2.5); 9.200(0.6); 9.171(9.3); 9.128(7.8); 8.313(2.6); 7.682(1.1); 7.666(2.8); 7.661(2.7); 7.645(5.2); 7.625(3.1); 7.608(1.4); 7.320(9.1); 7.300(16.0); 7.279(7.7); 7.199(0.5); 7.071(0.5); 6.944(0.5); 5.754(0.5); 3.432(0.5); 3.407(0.6); 3.391(0.8); 3.318(842.9); 3.185(0.4); 2.675(5.7); 2.670(7.6); 2.666(5.7); 2.574(0.8); 2.506(974.5); 2.501(1267.3); 2.497(924.6); 2.333(5.5); 2.328(7.4); 2.324(5.5); 1.235(0.8); 0.146(0.6); 0.008(5.1); 0.000(126.9); −0.008(5.0); −0.150(0.7)

Example I-1-8:
HPLC-MS: mass (m/z): 443.8 (M + H)+
$^1$H-NMR(601.6 MHz, $d_6$-DMSO): δ = 13.769(3.4); 8.314(0.4); 8.012(2.5); 8.000(2.6); 7.674(2.0); 7.671(2.1); 7.661(2.6); 7.659(2.6); 7.654(1.0); 7.651(0.9); 7.640(1.5); 7.629(0.9); 7.626(1.0); 7.615(0.4); 7.573(1.4); 7.560(2.6); 7.558(2.5); 7.546(1.3); 7.339(1.2); 7.336(1.2); 7.326(1.9); 7.324(1.9); 7.313(1.5); 7.308(3.0); 7.294(4.9); 7.280(2.5); 4.035(0.5); 4.023(0.4); 3.325(59.5); 3.323(54.0); 3.322(54.4); 3.320(79.6); 2.613(0.9); 2.610(0.7); 2.523(1.3); 2.520(1.7); 2.517(1.6); 2.508(47.0); 2.505(104.3); 2.502(148.2); 2.499(108.3); 2.496(50.8); 2.386(1.0); 1.989(1.9); 1.398(16.0); 1.187(0.5); 1.175(1.1); 1.163(0.6); 0.005(0.6); 0.000(20.5); −0.006(0.7)

Example I-1-9:
HPLC-MS: mass (m/z): 368.0 (M + H)+
$^1$H-NMR(400.0 MHz, $d_6$-DMSO): δ = 13.919(6.7); 8.316(1.2); 7.981(5.0); 7.962(5.8); 7.844(3.1); 7.827(7.5); 7.811(3.8); 7.795(5.9); 7.776(2.9); 7.753(3.7); 7.736(4.7); 7.718(2.0); 7.680(1.8); 7.663(3.4); 7.659(2.8); 7.647(2.1); 7.642(5.6); 7.637(2.1); 7.626(2.8); 7.621(3.4); 7.605(2.0); 7.588(0.8); 7.582(0.9); 7.564(0.5); 7.521(2.3); 7.384(5.2); 7.327(1.9); 7.319(9.9); 7.298(16.0); 7.278(8.1); 7.270(1.6); 7.247(2.5); 7.045(0.3); 6.906(0.7); 6.769(0.3); 6.286(0.3); 3.557(0.4); 3.540(0.3); 3.323(386.7); 2.680(1.3); 2.675(2.7); 2.671(3.7); 2.666(2.7); 2.662(1.3); 2.541(2.8); 2.524(13.3); 2.511(216.9); 2.506(432.4); 2.502(567.6); 2.497(405.6); 2.493(192.0); 2.337(1.3); 2.333(2.7); 2.328(3.7); 2.324(2.6); 2.319(1.2); 2.189(1.0); 1.989(1.1); 1.459(0.4); 1.442(0.4); 1.398(3.3); 1.268(1.5); 1.251(1.4); 1.204(1.1); 1.187(2.4); 1.175(1.1); 1.170(1.2); 1.159(1.9); 1.142(1.7); 1.104(0.7); 1.091(0.6); 1.047(0.6); 0.931(0.6); 0.146(2.7); 0.008(26.8); 0.000(645.6); −0.009(22.4); −0.025(0.8); −0.031(0.5); −0.150(2.8)

Example I-1-10:
HPLC-MS: mass (m/z): 363.0 (M + H)+
$^1$H-NMR(400.0 MHz, $d_6$-DMSO): δ = 13.971(6.2); 8.316(0.7); 8.263(5.3); 8.243(6.0); 7.974(1.3); 7.957(5.0); 7.954(5.0); 7.941(15.0); 7.936(13.4); 7.923(3.0); 7.917(1.0); 7.907(0.4); 7.889(4.2); 7.883(3.2); 7.872(3.3); 7.868(4.6); 7.862(2.9); 7.852(2.7); 7.846(2.3); 7.679(1.3); 7.663(2.9); 7.658(2.6); 7.646(2.1); 7.641(5.3); 7.637(2.1); 7.625(2.7); 7.620(3.1); 7.604(1.4); 7.326(1.8); 7.318(9.5); 7.298(16.0); 7.277(7.8); 7.269(1.6); 3.322(125.2); 2.676(1.4); 2.671(1.8); 2.666(1.4); 2.541(38.9); 2.524(4.8); 2.511(112.5); 2.506(220.1); 2.502(284.4); 2.497(204.0); 2.493(98.2); 2.333(1.4); 2.329(1.9); 2.324(1.4); 2.074(0.4); 1.175(0.5); 1.158(0.5); 0.146(1.4); 0.008(15.4); 0.000(322.2); −0.009(12.4); −0.034(0.4); −0.150(1.4)

Example I-1-11:
HPLC-MS: mass (m/z): 404.0 (M + H)+
$^1$H-NMR(400.0 MHz, $d_6$-DMSO): δ = 14.036(7.0); 8.316(0.7); 7.958(1.5); 7.944(2.0); 7.937(3.4); 7.924(3.4); 7.917(2.5); 7.904(2.2); 7.775(3.0); 7.747(3.5); 7.724(7.7); 7.704(5.0); 7.681(1.4); 7.665(2.9); 7.660(2.5); 7.648(2.1); 7.643(5.3); 7.639(2.0); 7.627(2.7); 7.622(3.1); 7.606(1.4); 7.329(1.4); 7.326(2.0); 7.318(9.6); 7.304(2.7); 7.298(16.0); 7.277(7.8); 7.269(1.5); 3.322(102.6); 2.676(1.3); 2.671(1.7); 2.667(1.2); 2.662(0.6); 2.542(62.1); 2.511(104.2); 2.507(198.0); 2.502(253.2); 2.498(179.5); 2.493(85.0); 2.338(0.6); 2.333(1.2); 2.329(1.6); 2.324(1.2); 0.146(1.3); 0.008(17.2); 0.000(304.2); −0.009(11.2); −0.029(0.4); −0.150(1.3)

Example I-1-12:
HPLC-MS: mass (m/z): 403.9 (M + H)+
$^1$H-NMR(400.0 MHz, $d_6$-DMSO): δ = 14.253(8.3); 7.923(0.9); 7.903(2.7); 7.892(1.8); 7.884(4.2); 7.869(3.1); 7.857(4.4); 7.833(13.6); 7.812(5.2); 7.689(1.4); 7.672(2.8); 7.668(2.6); 7.656(1.9); 7.651(5.2); 7.647(1.9); 7.635(2.7); 7.630(3.1); 7.614(1.4); 7.334(1.7); 7.327(9.4); 7.313(2.1); 7.306(16.0); 7.285(7.6); 7.278(1.5); 5.760(3.2); 3.336(6.5); 3.024(0.5); 2.781(0.4); 2.676(0.4); 2.529(1.2); 2.516(20.1); 2.511(40.3); 2.507(52.9); 2.502(38.1); 2.498(18.2); 1.232(0.3); 0.000(4.8)

Example I-1-13:
HPLC-MS: mass (m/z): 387.0 (M + H)+
$^1$H-NMR(400.0 MHz, $d_6$-DMSO): δ = 14.077(4.4); 9.018(5.5); 9.007(5.4); 8.493(4.6); 8.473(4.9); 8.316(2.4); 7.934(3.0); 7.922(3.2); 7.915(3.1); 7.903(2.6); 7.683(1.3); 7.667(2.8); 7.662(2.5); 7.645(5.2); 7.629(2.8); 7.624(3.0); 7.608(1.3); 7.328(1.9); 7.321(9.4); 7.300(16.0); 7.280(7.8); 7.272(1.5); 3.382(0.5); 3.322(663.8); 2.675(5.5); 2.671(7.4); 2.666(5.3); 2.662(2.6); 2.603(0.5); 2.541(9.3); 2.524(20.1); 2.511(433.8); 2.506(860.9); 2.502(1118.2); 2.497(788.5); 2.493(366.9); 2.453(0.9); 2.333(5.3); 2.328(7.1); 2.324(5.1); 2.319(2.4); 2.074(0.7); 0.146(0.4); 0.008(3.9); 0.000(104.4); −0.008(3.5); −0.150(0.5)

Example I-1-14:
HPLC-MS: mass (m/z): 369.0 (M + H)+
$^1$H-NMR(400.0 MHz, $d_6$-DMSO): δ = 14.022(4.5); 8.909(5.8); 8.905(6.2); 8.897(6.2); 8.893(6.1); 8.388(5.5); 8.368(5.8); 8.316(1.0); 7.796(4.3); 7.784(4.3); 7.777(4.2); 7.764(4.0); 7.682(1.3); 7.666(2.8); 7.661(2.6); 7.649(1.9); 7.644(5.3); 7.628(2.7); 7.623(3.1); 7.607(1.4); 7.385(3.0); 7.328(1.6); 7.321(9.5); 7.300(16.0); 7.280(7.9); 7.272(1.5); 7.250(6.6); 7.116(3.3); 3.325(125.0); 2.995(0.9); 2.675(1.7); 2.671(2.3); 2.667(1.7); 2.541(22.1); 2.524(5.6); 2.511(131.5); 2.506(261.9); 2.502(342.7); 2.498(247.9); 2.493(120.4); 2.333(1.6); 2.329(2.2); 2.324(1.7); 1.469(0.4); 0.146(1.9); 0.008(15.4); 0.000(399.5); −0.008(14.8); −0.150(2.0)

Example I-1-15:
HPLC-MS: mass (m/z): 385.9 (M + H)+
$^1$H-NMR(400.0 MHz, $d_6$-DMSO): δ = 14.060(11.4); 8.316(1.6); 7.928(7.7); 7.908(9.5); 7.857(3.6); 7.842(11.2); 7.837(15.6); 7.818(8.7); 7.799(3.5); 7.773(4.8); 7.753(6.3); 7.737(4.8); 7.721(4.9); 7.703(3.0); 7.700(3.0); 7.683(1.3); 7.668(0.4); 7.650(0.4); 7.401(0.6); 7.359(8.9); 7.338(16.0); 7.317(7.7); 7.299(0.5); 7.278(0.5); 4.038(0.6); 4.020(0.8); 3.395(0.4); 3.377(0.5); 3.324(420.5); 2.680(1.3); 2.676(2.6); 2.671(3.6); 2.667(2.6); 2.541(22.2); 2.524(9.7); 2.520(15.7); 2.511(205.4); 2.507(417.9); 2.502(550.4); 2.498(392.5); 2.493(184.3); 2.338(1.2); 2.333(2.5); 2.329(3.5); 2.324(2.5); 2.320(1.2); 1.989(2.5); 1.398(8.4); 1.244(0.6); 1.227(0.6); 1.193(0.8); 1.179(1.0); 1.175(1.8); 1.157(0.9); 1.138(0.4); 1.121(1.3); 1.104(1.2); 0.146(1.3); 0.008(10.9); 0.000(313.4); −0.009(9.7); −0.150(1.3)

Example I-1-16:
HPLC-MS: mass (m/z): 428.0 (M + H)+
$^1$H-NMR(400.0 MHz, $d_6$-DMSO): δ = 13.767(10.4); 8.316(1.8); 7.923(6.9); 7.904(8.2); 7.842(2.3); 7.829(16.0); 7.823(11.0); 7.813(8.6); 7.801(6.5); 7.797(6.1); 7.782(7.4); 7.778(7.3); 7.766(3.9); 7.751(10.3); 7.746(12.0); 7.732(8.8); 7.728(9.8); 7.656(0.5); 7.636(0.5); 7.575(2.3); 7.572(2.8); 7.556(6.8); 7.553(6.8); 7.538(8.2); 7.517(4.9); 7.512(4.6); 7.498(1.8); 7.494(1.5); 7.430(0.4); 7.324(0.4); 7.305(0.4); 7.279(0.4); 3.464(0.3); 3.449(0.4); 3.432(0.3); 3.358(1.1); 3.324(929.0); 3.285(0.6); 3.076(0.4); 2.680(2.1); 2.675(4.4); 2.671(5.8); 2.666(4.2); 2.662(2.0); 2.541(3.8); 2.524(17.7); 2.511(333.2); 2.506(660.5); 2.502(861.2); 2.497(613.5); 2.493(289.0); 2.337(2.0); 2.333(4.1); 2.328(5.7); 2.324(4.1); 2.319(1.9); 1.989(0.4); 1.466(2.7); 1.449(2.7); 1.398(6.1); 1.199(0.5); 1.190(0.5); 1.176(1.5); 1.160(1.3); 1.106(1.2); 1.040(1.3); 1.024(1.2); 0.146(5.2); 0.043(0.4); 0.034(0.7); 0.008(51.6); 0.000(1193.8); −0.009(43.1); −0.039(0.8); −0.066(0.4); −0.150(5.3)

TABLE 4-continued

Example I-1-17:
HPLC-MS: mass (m/z): 383.9 (M + H)⁺
¹H-NMR(400.0 MHz, d₆-DMSO): δ = 13.786(8.5); 7.926(6.9); 7.906(8.2); 7.850(0.9); 7.844(2.2); 7.832(16.0); 7.825(10.4); 7.816(8.3); 7.796(2.6); 7.789(6.7); 7.786(7.0); 7.770(11.3); 7.766(10.6); 7.751(3.8); 7.749(4.1); 7.734(2.2); 7.728(1.6); 7.657(2.5); 7.654(3.8); 7.637(11.3); 7.633(14.2); 7.628(7.1); 7.615(8.2); 7.611(7.5); 7.595(3.2); 7.591(3.0); 7.562(0.4); 7.539(5.8); 7.535(5.5); 7.521(6.7); 7.517(6.3); 7.511(1.2); 7.503(4.1); 7.499(3.8); 7.495(0.8); 7.488(1.0); 7.420(0.5); 7.412(0.4); 7.402(2.0); 7.395(1.1); 7.393(0.9); 7.389(0.9); 7.386(1.1); 7.379(1.8); 7.301(0.9); 7.294(0.5); 7.291(0.5); 7.287(0.6); 7.278(0.6); 3.599(0.5); 3.582(0.7); 3.565(0.5); 3.475(0.5); 3.458(0.7); 3.441(0.5); 3.329(98.1); 3.077(2.4); 2.677(0.5); 2.672(0.7); 2.668(0.5); 2.543(0.4); 2.526(2.1); 2.512(38.2); 2.508(75.9); 2.503(99.1); 2.499(70.2); 2.494(32.7); 2.335(0.5); 2.330(0.6); 2.326(0.4); 1.469(4.0); 1.459(4.2); 1.452(4.0); 1.442(3.9); 1.427(0.6); 1.259(0.4); 1.234(0.4); 1.212(0.4); 1.194(0.9); 1.177(0.6); 1.166(0.8); 1.151(3.9); 1.134(3.6); 1.106(7.7); 1.050(0.8); 1.044(3.6); 1.033(0.9); 1.027(3.5); 0.146(0.7); 0.008(6.4); 0.000(150.5); −0.009(5.0); −0.150(0.7)

Example I-1-18:
HPLC-MS: mass (m/z): 418.0 (M + H)⁺
¹H-NMR(400.0 MHz, d₆-DMSO): δ = 13.883(7.2); 8.315(0.6); 8.053(0.6); 7.946(4.4); 7.925(14.3); 7.906(12.8); 7.874(2.7); 7.857(6.7); 7.832(16.0); 7.814(10.1); 7.795(3.9); 7.767(3.7); 7.748(4.3); 7.731(2.3); 7.698(0.4); 7.650(0.5); 7.628(0.6); 7.608(0.5); 7.458(0.3); 3.431(0.3); 3.324(277.7); 3.286(0.4); 3.268(0.3); 3.076(1.8); 2.670(2.2); 2.666(1.7); 2.540(1.2); 2.505(262.3); 2.501(334.4); 2.497(255.4); 2.328(2.2); 2.324(1.7); 1.467(1.2); 1.450(1.2); 1.426(0.5); 1.414(1.2); 1.397(1.2); 1.304(0.7); 1.287(0.7); 1.260(1.1); 1.242(1.0); 1.236(0.8); 1.221(0.3); 1.181(0.7); 1.164(1.4); 1.146(0.8); 1.105(5.7); 1.087(1.3); 1.080(1.4); 1.069(1.8); 1.051(2.0); 1.036(1.1); 0.936(0.4); 0.145(1.7); 0.007(14.7); −0.0005(324.0); −0.0010(326.9); −0.150(1.8)

Example I-1-19:
HPLC-MS: mass (m/z): 419.0 (M + H)⁺
¹H-NMR(400.0 MHz, d₆-DMSO): δ = 13.978(7.0); 9.023(9.2); 9.012(9.1); 9.011(9.1); 8.496(8.6); 8.494(8.8); 8.476(9.3); 8.474(9.2); 8.314(0.7); 7.940(6.8); 7.929(14.6); 7.920(7.2); 7.909(16.0); 7.864(4.4); 7.848(12.2); 7.845(12.6); 7.822(9.7); 7.803(4.1); 7.775(5.7); 7.773(5.7); 7.755(7.2); 7.738(2.8); 7.721(0.4); 5.754(4.5); 3.318(78.2); 3.182(0.6); 3.065(0.6); 2.681(0.6); 2.676(1.1); 2.672(1.5); 2.667(1.1); 2.512(82.2); 2.507(162.7); 2.503(219.5); 2.498(167.6); 2.494(85.1); 2.334(1.0); 2.329(1.4); 2.325(1.0); 1.234(0.7); 0.146(1.2); 0.008(12.5); 0.000(270.7); −0.008(11.7); −0.150(1.2)

Example I-1-20:
HPLC-MS: mass (m/z): 418.9 (M + H)⁺
¹H-NMR(400.0 MHz, d₆-DMSO): δ = 13.999(11.2); 8.948(8.3); 8.937(8.3); 8.444(7.6); 8.425(8.1); 8.314(1.3); 7.939(6.7); 7.927(14.9); 7.907(16.0); 7.880(0.4); 7.856(4.3); 7.836(14.8); 7.815(9.6); 7.796(3.9); 7.769(5.8); 7.750(6.9); 7.732(2.8); 3.316(102.3); 3.015(0.7); 2.675(2.5); 2.671(3.3); 2.666(2.6); 2.506(372.2); 2.501(493.7); 2.497(382.0); 2.332(2.3); 2.328(3.2); 2.324(2.5); 1.398(2.2); 0.146(2.7); 0.008(29.6); 0.000(559.3); −0.008(30.7); −0.044(0.3); −0.150(2.8)

Example I-1-21:
HPLC-MS: mass (m/z): 393.9 (M + H)⁺
¹H-NMR(400.0 MHz, CD3CN): δ = 11.163(0.5); 7.857(7.8); 7.853(6.2); 7.851(6.0); 7.839(10.2); 7.834(8.4); 7.768(7.6); 7.765(7.1); 7.749(9.8); 7.746(8.9); 7.673(6.8); 7.668(7.9); 7.655(7.8); 7.653(7.8); 7.649(9.3); 7.568(5.9); 7.564(7.5); 7.551(10.1); 7.548(11.3); 7.545(10.9); 7.532(10.2); 7.529(10.2); 7.514(8.0); 7.510(8.1); 7.507(9.0); 7.502(8.1); 7.493(4.4); 7.488(12.1); 7.483(8.7); 7.475(10.0); 7.469(11.4); 7.464(3.8); 7.456(16.0); 7.451(11.4); 7.438(9.9); 7.434(8.2); 7.419(3.3); 7.415(2.7); 5.448(1.2); 2.159(7.7); 2.115(1.7); 2.108(1.5); 2.102(1.2); 1.972(0.6); 1.965(3.0); 1.959(4.2); 1.953(26.8); 1.947(49.3); 1.941(67.0); 1.935(45.5); 1.929(23.1); 1.769(0.4); 1.436(1.1); 1.377(0.4); 1.372(0.7); 1.338(0.5); 1.283(0.6); 1.276(0.9); 1.268(0.5); 0.008(1.9); 0.000(43.5); −0.009(1.6)

Example I-1-22:
HPLC-MS: mass (m/z): 349.9 (M + H)⁺
¹H-NMR(400.0 MHz, CD3CN): δ = 11.219(0.4); 7.856(5.2); 7.851(4.3); 7.849(4.0); 7.837(6.9); 7.832(5.8); 7.720(4.3); 7.718(6.4); 7.715(4.5); 7.701(5.2); 7.699(6.5); 7.698(6.2); 7.696(5.3); 7.592(1.1); 7.584(11.0); 7.581(13.7); 7.574(11.4); 7.572(16.0); 7.569(8.9); 7.566(5.5); 7.561(5.6); 7.552(1.4); 7.547(5.1); 7.545(5.5); 7.542(6.7); 7.524(0.3); 7.515(1.0); 7.504(4.8); 7.494(5.4); 7.493(5.3); 7.490(3.6); 7.485(7.3); 7.483(4.3); 7.476(4.3); 7.472(8.7); 7.467(6.5); 7.464(3.7); 7.454(10.9); 7.448(8.2); 7.435(6.7); 7.431(5.6); 7.416(2.2); 7.413(1.8); 5.448(0.7); 2.169(6.7); 2.115(0.8); 2.109(0.7); 2.103(0.6); 2.096(0.4); 1.965(1.5); 1.959(2.1); 1.954(13.1); 1.947(24.3); 1.941(33.2); 1.935(22.8); 1.929(11.6); 1.371(0.5); 1.283(0.4); 1.275(0.6); 1.267(0.5); 0.008(1.0); 0.000(21.1); −0.009(0.7)

Example I-1-23:
HPLC-MS: mass (m/z): 384.0 (M + H)⁺
¹H-NMR(400.0 MHz, CD3CN): δ = 11.145(0.5); 7.903(2.5); 7.895(1.1); 7.888(3.5); 7.883(2.4); 7.855(3.9); 7.850(3.3); 7.837(4.8); 7.831(4.4); 7.807(2.6); 7.796(16.0); 7.793(15.3); 7.779(2.8); 7.769(1.7); 7.755(0.6); 7.569(2.9); 7.565(3.6); 7.551(3.7); 7.549(3.8); 7.546(5.0); 7.494(1.7); 7.489(2.2); 7.476(4.6); 7.471(4.2); 7.457(6.9); 7.452(6.6); 7.438(4.8); 7.434(4.1); 7.419(1.6); 7.416(1.5); 5.447(1.4); 2.145(6.7); 2.107(0.8); 2.101(0.6); 1.964(2.2); 1.958(2.7); 1.952(16.3); 1.946(29.6); 1.940(39.9); 1.934(27.2); 1.927(13.9); 1.679(0.7); 1.663(0.6); 1.268(0.3); 0.008(0.7); 0.000(16.8); −0.009(0.5)

Example I-1-24:
HPLC-MS: mass (m/z): 350.9 (M + H)⁺
¹H-NMR(400.0 MHz, CD3CN): δ = 11.728(2.0); 8.655(14.4); 8.652(14.5); 8.644(14.8); 8.640(14.2); 8.057(14.1); 8.054(13.9); 8.036(16.0); 8.033(15.0); 7.903(0.4); 7.889(11.2); 7.888(11.2); 7.884(9.0); 7.881(8.1); 7.871(14.6); 7.865(12.2); 7.855(0.4); 7.849(0.4); 7.657(15.5); 7.646(12.5); 7.637(14.1); 7.625(13.7); 7.568(8.3); 7.564(10.8); 7.551(9.5); 7.549(10.6); 7.546(13.7); 7.530(0.7); 7.491(4.7); 7.486(5.9); 7.473(14.3); 7.468(13.1); 7.457(15.9); 7.455(15.6); 7.452(15.1); 7.448(11.0); 7.439(14.8); 7.435(12.0); 7.420(4.8); 7.416(3.6); 5.448(3.6); 4.068(0.5); 4.050(0.6); 3.602(0.4); 2.158(50.4); 2.121(1.2); 2.114(1.1); 2.108(1.1); 2.102(0.8); 2.096(0.5); 1.972(2.9); 1.965(5.0); 1.959(5.9); 1.953(39.2); 1.947(72.2); 1.941(99.0); 1.935(67.9); 1.928(34.6); 1.775(0.5); 1.769(0.6); 1.763(0.4); 1.436(2.3); 1.371(3.3); 1.339(0.8); 1.284(1.2); 1.276(4.0); 1.265(1.4); 1.222(0.8); 1.204(1.4); 1.186(0.8); 0.008(1.8); 0.000(46.2); −0.009(1.6)

Example I-1-25:
HPLC-MS: mass (m/z): 351.9 (M + H)⁺
¹H-NMR(400.0 MHz, d₆-DMSO): δ = 14.075(8.2); 13.921(0.5); 8.316(2.5); 7.927(0.4); 7.875(8.2); 7.870(7.5); 7.856(10.3); 7.851(9.2); 7.756(1.3); 7.739(2.8); 7.735(2.9); 7.718(4.8); 7.698(3.0); 7.681(1.3); 7.658(0.5); 7.649(0.7); 7.638(6.9); 7.635(7.7); 7.618(9.6); 7.615(10.8); 7.607(1.1); 7.585(1.4); 7.559(4.1); 7.555(4.7); 7.541(9.2); 7.536(8.4); 7.522(6.9); 7.516(7.1); 7.514(9.0); 7.509(8.1); 7.495(9.9); 7.491(9.2); 7.476(3.7); 7.473(3.0); 7.426(0.4); 7.356(9.0); 7.335(16.0); 7.314(7.7); 7.274(0.3); 7.225(2.6); 7.204(4.6); 7.183(2.2); 3.687(0.6); 3.505(0.7); 3.487(0.5); 3.469(0.6); 3.396(0.3); 3.323(444.0); 3.163(0.5); 3.145(0.5); 3.024(0.6); 2.945(0.3); 2.857(0.5); 2.680(2.4); 2.676(5.0); 2.671(6.9); 2.666(4.9); 2.662(2.3); 2.572(0.9); 2.524(22.5); 2.511(404.6); 2.506(803.5); 2.502(1045.5); 2.497(740.9); 2.493(346.7); 2.338(2.4); 2.333(5.0); 2.329(6.8); 2.324(4.7); 2.320(2.2); 1.258(0.4); 1.235(1.6); 1.162(0.6); 1.145(1.2); 1.127(0.5); 1.023(0.5); 1.005(0.9); 0.987(0.4); 0.146(0.7); 0.008(6.3); 0.000(175.2); −0.009(5.6); −0.150(0.6)

TABLE 4-continued

Example I-1-26:
HPLC-MS: mass (m/z): 441.9 (M + H)$^+$
$^1$H-NMR(400.0 MHz, d$_6$-DMSO): δ = 8.316(1.0); 7.988(2.3); 7.969(2.7); 7.954(0.8); 7.850(2.6); 7.845(2.2); 7.832(3.3); 7.827(3.0); 7.690(0.4); 7.673(3.1); 7.669(3.4); 7.654(3.8); 7.650(3.8); 7.609(1.8); 7.590(2.6); 7.545(1.2); 7.526(2.8); 7.506(2.8); 7.492(3.6); 7.487(3.3); 7.473(2.6); 7.469(2.4); 7.455(1.1); 7.273(1.2); 7.234(0.4); 7.214(0.5); 4.055(1.2); 4.038(3.5); 4.020(3.6); 4.002(1.2); 3.322(144.1); 2.680(1.0); 2.675(2.0); 2.671(2.8); 2.666(2.0); 2.661(0.9); 2.524(8.4); 2.519(12.8); 2.511(154.9); 2.506(312.0); 2.501(410.2); 2.497(290.9); 2.492(135.5); 2.337(0.9); 2.333(1.9); 2.328(2.6); 2.324(1.8); 2.319(0.9); 1.989(16.0); 1.234(0.9); 1.193(4.4); 1.175(8.6); 1.157(4.3); 0.008(0.9); 0.000(25.5); −0.009(0.7)
Example I-1-27:
HPLC-MS: mass (m/z): 401.9 (M + H)$^+$
$^1$H-NMR(601.6 MHz, CD3CN): δ = 7.845(5.3); 7.842(4.6); 7.841(4.9); 7.832(6.9); 7.829(5.9); 7.765(1.3); 7.752(2.7); 7.742(2.4); 7.739(1.8); 7.729(1.7); 7.692(6.1); 7.679(3.9); 7.626(0.4); 7.624(0.3); 7.615(0.4); 7.612(0.8); 7.611(0.8); 7.606(0.6); 7.603(0.8); 7.602(0.8); 7.599(0.7); 7.598(0.8); 7.590(0.8); 7.589(0.8); 7.580(2.5); 7.576(2.9); 7.561(4.7); 7.557(5.2); 7.555(6.2); 7.545(6.3); 7.542(6.3); 7.517(0.4); 7.509(0.6); 7.507(0.7); 7.497(0.5); 7.496(0.5); 7.494(0.6); 7.474(2.8); 7.471(3.9); 7.461(6.5); 7.458(6.3); 7.449(5.1); 7.445(4.7); 7.441(6.4); 7.438(6.2); 7.435(0.5); 7.428(7.3); 7.426(7.0); 7.418(0.8); 7.416(3.0); 7.414(2.8); 7.405(0.5); 7.402(0.4); 7.396(0.5); 7.394(0.5); 7.384(0.6); 7.381(0.6); 7.369(0.4); 4.077(2.0); 4.065(6.1); 4.053(6.0); 4.041(2.1); 3.049(2.7); 2.993(2.2); 2.985(2.2); 2.800(1.8); 2.054(0.5); 2.050(0.8); 2.046(0.5); 1.971(28.0); 1.963(5.5); 1.955(9.1); 1.951(9.6); 1.947(53.3); 1.943(93.0); 1.939(132.5); 1.935(87.4); 1.931(46.6); 1.926(1.8); 1.922(0.9); 1.832(0.3); 1.828(0.6); 1.824(0.9); 1.820(0.6); 1.360(0.3); 1.340(0.9); 1.307(0.4); 1.285(1.5); 1.269(2.9); 1.263(1.1); 1.215(8.0); 1.204(16.0); 1.192(8.3); 0.893(0.3); 0.881(0.7); 0.869(0.5); 0.846(0.3); 0.096(0.5); 0.005(3.7); 0.000(142.5); −0.006(4.2); −0.100(0.5)
Example I-1-28:
HPLC-MS: mass (m/z): 343.1 (M + H)$^+$
$^1$H-NMR(400.0 MHz, d$_6$-DMSO): δ = 14.168(7.1); 8.314(1.3); 8.275(9.0); 8.273(9.6); 8.255(10.5); 8.253(10.2); 8.027(8.7); 8.010(9.2); 8.008(9.6); 7.900(4.7); 7.897(4.9); 7.881(9.3); 7.878(9.3); 7.862(5.5); 7.858(5.5); 7.759(1.1); 7.745(7.4); 7.742(8.6); 7.726(11.6); 7.723(13.6); 7.707(6.2); 7.704(7.0); 7.684(1.2); 7.359(8.9); 7.338(16.0); 7.317(7.7); 3.317(425.8); 2.680(1.3); 2.675(2.7); 2.671(3.8); 2.666(2.8); 2.662(1.4); 2.524(8.4); 2.519(13.2); 2.511(220.4); 2.506(471.4); 2.502(640.6); 2.497(463.4); 2.493(222.3); 2.425(0.3); 2.338(1.3); 2.333(2.7); 2.328(3.8); 2.324(2.8); 2.074(1.4); 0.008(2.0); 0.000(71.6); −0.009(2.4)
Example I-1-29:
HPLC-MS: mass (m/z): 352.9 (M + H)$^+$
$^1$H-NMR(400.0 MHz, d$_6$-DMSO): δ = 13.979(8.2); 8.631(6.0); 8.627(6.5); 8.619(6.5); 8.614(6.4); 8.313(0.5); 8.284(6.3); 8.279(6.5); 8.265(6.9); 8.260(6.7); 7.680(1.2); 7.664(2.8); 7.659(2.9); 7.649(7.7); 7.643(6.2); 7.637(8.3); 7.630(7.4); 7.618(6.9); 7.606(1.5); 7.324(1.7); 7.317(9.1); 7.297(16.0); 7.276(7.7); 3.316(93.5); 2.671(1.4); 2.506(158.6); 2.502(209.0); 2.498(166.2); 2.329(1.4); 0.000(10.2)
Example I-1-30:
HPLC-MS: mass (m/z): 386.0 ([M − Na$^+$ + H$^+$] + H)$^+$
$^1$H-NMR(400.0 MHz, d$_6$-DMSO): δ = 8.694(2.7); 8.685(2.7); 8.683(2.7); 8.529(0.5); 8.315(3.9); 8.144(2.5); 8.126(2.7); 8.124(2.7); 7.721(2.5); 7.709(2.5); 7.702(2.4); 7.690(2.2); 7.542(0.7); 7.525(1.4); 7.520(1.3); 7.509(1.0); 7.504(2.7); 7.500(1.0); 7.488(1.3); 7.483(1.6); 7.467(0.7); 7.209(0.4); 7.205(0.6); 7.195(4.2); 7.188(0.7); 7.184(0.8); 7.175(6.2); 7.166(0.9); 7.155(3.5); 7.144(0.5); 4.100(0.6); 4.088(0.5); 3.722(0.4); 3.327(32.2); 3.300(23.3); 3.206(0.4); 3.159(16.0); 2.675(0.9); 2.671(1.3); 2.667(0.9); 2.524(4.6); 2.519(7.0); 2.511(74.8); 2.506(151.2); 2.502(198.3); 2.497(143.0); 2.493(69.4); 2.333(0.8); 2.329(1.2); 2.324(0.8); 0.008(1.0); 0.000(28.1); −0.008(1.0)
Example I-1-31:
HPLC-MS: mass (m/z): 560.0 (M + H)$^+$
$^1$H-NMR(400.0 MHz, d$_6$-DMSO): δ = 14.074(0.7); 8.953(2.2); 8.938(13.6); 8.926(12.5); 8.855(1.7); 8.843(1.8); 8.627(10.7); 8.607(11.2); 8.444(1.6); 8.424(1.7); 8.315(0.7); 8.273(1.6); 8.253(1.7); 7.948(1.3); 7.935(1.3); 7.928(1.4); 7.916(1.2); 7.894(9.6); 7.882(9.8); 7.874(9.6); 7.862(9.1); 7.841(1.4); 7.829(1.4); 7.821(1.3); 7.809(1.2); 7.681(0.4); 7.661(0.9); 7.644(1.5); 7.623(1.0); 7.606(0.5); 7.597(1.3); 7.581(2.6); 7.576(2.6); 7.560(5.0); 7.543(2.7); 7.539(3.0); 7.523(1.3); 7.319(2.7); 7.298(4.7); 7.278(2.2); 7.184(8.8); 7.163(16.0); 7.142(7.5); 3.322(104.2); 2.672(1.7); 2.508(225.2); 2.504(296.0); 2.499(220.6); 2.334(1.3); 2.330(1.8); 2.326(1.3); 2.075(13.9); 0.146(1.4); 0.008(12.4); 0.000(283.6); −0.008(12.1); −0.150(1.4)
Example I-1-32:
HPLC-MS: mass (m/z): 388.0 (M + H)$^+$
$^1$H-NMR(400.0 MHz, d$_6$-DMSO): δ = 14.252(0.5); 9.670(7.1); 9.572(8.0); 7.693(0.5); 7.677(1.1); 7.672(1.0); 7.660(0.8); 7.655(2.2); 7.651(0.8); 7.639(1.1); 7.634(1.3); 7.618(0.6); 7.341(0.5); 7.337(0.7); 7.330(3.9); 7.309(6.6); 7.288(3.2); 7.281(0.6); 3.343(8.6); 2.513(14.3); 2.508(18.8); 2.504(13.6); 2.499(6.6); 2.079(16.0); 0.000(0.5)
Example I-1-33:
HPLC-MS: mass (m/z): 349.0 (M + H)$^+$
$^1$H-NMR(400.0 MHz, d$_6$-DMSO): δ = 13.223(1.2); 8.438(1.4); 8.434(1.6); 8.426(1.5); 8.421(1.5); 8.313(0.4); 8.185(1.5); 8.180(1.5); 8.166(1.6); 8.161(1.5); 7.661(0.7); 7.656(0.7); 7.640(1.4); 7.623(0.8); 7.618(0.7); 7.602(0.4); 7.320(0.4); 7.313(2.2); 7.292(3.8); 7.272(1.9); 7.218(1.5); 7.206(1.5); 7.199(1.5); 7.187(1.5); 3.995(16.0); 3.318(137.2); 2.675(0.8); 2.670(1.1); 2.666(0.8); 2.510(65.1); 2.506(133.9); 2.501(179.5); 2.497(133.1); 2.333(0.7); 2.328(1.0); 2.324(0.8); 0.000(6.1)
Example I-1-34:
HPLC-MS: mass (m/z): 415.1 (M + H)$^+$
$^1$H-NMR(600.1 MHz, d$_6$-DMSO): δ = 9.022(3.8); 9.014(3.9); 8.538(3.7); 8.525(3.9); 8.011(3.0); 8.003(3.1); 7.997(3.1); 7.989(2.9); 7.687(0.7); 7.676(1.6); 7.673(1.6); 7.662(3.0); 7.651(1.7); 7.648(1.8); 7.637(0.8); 7.332(1.0); 7.327(5.3); 7.314(9.1); 7.300(4.7); 4.006(1.5); 3.332(296.9); 2.617(0.4); 2.614(0.3); 2.526(0.7); 2.522(0.9); 2.519(0.9); 2.508(48.1); 2.505(65.9); 2.502(49.9); 2.388(0.4); 2.076(1.2); 1.234(7.5); 1.223(16.0); 1.211(7.4); 0.000(0.8)
Example I-1-35:
HPLC-MS: mass (m/z): 410.1 (M + H)$^+$
$^1$H-NMR(400.0 MHz, d$_6$-DMSO): δ = 19.971(0.3); 14.034(10.3); 12.734(0.3); 8.313(1.1); 8.129(0.9); 7.671(1.3); 7.651(3.8); 7.633(5.8); 7.615(4.4); 7.597(1.7); 7.580(0.3); 7.308(9.0); 7.287(16.0); 7.266(8.3); 4.464(14.4); 4.278(0.3); 3.408(0.4); 3.318(414.6); 3.199(0.4); 2.995(0.5); 2.890(0.7); 2.852(0.4); 2.730(0.7); 2.671(4.2); 2.640(0.4); 2.502(712.7); 2.498(712.8); 2.329(4.3); 2.074(1.0); 1.258(0.7); 1.244(0.6); 0.145(0.4); 0.000(43.0); −0.003(34.2)
Example I-1-36:
HPLC-MS: mass (m/z): 347.1 (M + H)$^+$
$^1$H-NMR(400.0 MHz, d$_6$-DMSO): δ = 13.801(3.7); 8.702(2.9); 8.698(3.2); 8.690(3.1); 8.686(3.0); 8.112(2.8); 8.108(2.9); 8.092(3.1); 8.088(2.9); 7.678(0.6); 7.662(1.3); 7.657(1.2); 7.646(1.0); 7.641(2.5); 7.624(1.3); 7.620(1.5); 7.604(0.7); 7.431(2.7); 7.419(2.7); 7.412(2.6); 7.399(2.5); 7.324(0.8); 7.317(4.4); 7.296(7.4); 7.275(3.6); 7.268(0.7); 3.340(79.0); 2.963(1.9); 2.944(6.1); 2.925(6.2); 2.907(2.0); 2.676(0.4); 2.671(0.5); 2.667(0.4); 2.511(31.3); 2.507(61.3); 2.502(82.1); 2.498(61.9); 2.333(0.4); 2.329(0.5); 2.074(2.8); 1.258(7.6); 1.239(16.0); 1.220(7.3); 0.008(1.4); 0.000(30.3); −0.008(1.2)

TABLE 4-continued

Example I-1-37:
HPLC-MS: mass (m/z): 437.1 (M + H)+
1H-NMR(400.0 MHz, d6-DMSO): δ = 14.026(7.7); 8.982(5.7); 8.970(5.8); 8.469(5.5); 8.465(5.8); 8.449(6.1); 8.445(6.0); 7.963(4.6); 7.951(4.6); 7.943(4.4); 7.931(4.2); 7.684(1.3); 7.668(2.7); 7.663(2.5); 7.652(1.8); 7.647(5.2); 7.630(2.7); 7.626(3.1); 7.610(1.3); 7.330(1.6); 7.323(9.4); 7.302(16.0); 7.281(7.7); 7.273(1.5); 3.322(130.9); 2.672(0.9); 2.667(0.6); 2.512(48.3); 2.508(101.7); 2.503(142.7); 2.499(108.4); 2.494(53.3); 2.330(0.8); 0.146(0.4); 0.008(3.1); 0.000(86.5); −0.008(3.2); −0.149(0.3)
Example I-1-38:
HPLC-MS: mass (m/z): 401.0 (M + H)+
1H-NMR(400.0 MHz, d6-DMSO): δ = 13.967(5.7); 8.812(4.0); 8.808(4.9); 8.800(4.5); 8.796(4.9); 8.309(3.8); 8.306(4.6); 8.289(4.2); 8.286(4.8); 7.684(0.8); 7.667(1.8); 7.663(2.0); 7.642(5.7); 7.630(5.5); 7.623(4.9); 7.610(4.3); 7.330(1.2); 7.323(5.8); 7.303(10.2); 7.282(4.9); 4.193(2.2); 4.165(6.9); 4.137(7.1); 4.109(2.4); 3.326(42.1); 2.673(0.4); 2.508(47.1); 2.504(66.5); 2.500(57.5); 2.331(0.4); 2.076(16.0); 0.008(1.8); 0.000(40.2)
Example I-1-39:
HPLC-MS: mass (m/z): 392.0 (M + H)+
1H-NMR(400.0 MHz, d6-DMSO): δ = 13.638(1.1); 8.314(0.8); 7.670(1.3); 7.653(2.8); 7.649(2.6); 7.637(1.9); 7.632(5.3); 7.628(2.0); 7.616(2.7); 7.611(3.1); 7.595(1.4); 7.312(1.6); 7.304(9.6); 7.284(16.0); 7.263(8.0); 7.255(1.5); 6.891(1.0); 6.761(2.2); 6.630(1.1); 4.466(8.0); 4.455(9.4); 4.444(8.3); 3.330(27.5); 3.237(8.1); 3.226(9.4); 3.215(7.8); 2.675(1.7); 2.671(2.4); 2.666(1.7); 2.524(5.5); 2.510(132.8); 2.506(279.6); 2.501(391.5); 2.497(291.6); 2.493(141.2); 2.333(1.7); 2.328(2.4); 2.324(1.7); 2.073(1.8); 0.146(1.3); 0.008(10.4); 0.000(291.3); −0.008(10.6); −0.150(1.3)
Example I-1-40:
HPLC-MS: mass (m/z): 334.2 (M + H)+
1H-NMR(400.0 MHz, d6-DMSO): δ = 13.741(1.6); 8.824(3.1); 8.819(3.2); 8.691(3.1); 8.314(0.4); 7.680(0.4); 7.661(0.9); 7.643(1.5); 7.626(1.0); 7.607(0.4); 7.318(2.5); 7.297(4.3); 7.277(2.1); 3.320(322.5); 2.827(16.0); 2.670(3.0); 2.611(0.4); 2.540(10.9); 2.501(501.2); 2.328(2.8); 1.258(0.3); 1.238(0.6); 0.000(44.6)
Example I-1-41:
HPLC-MS: mass (m/z): 330.1 (M + H)+
1H-NMR(400.0 MHz, CD3CN): δ = 7.853(1.7); 7.848(1.3); 7.846(1.2); 7.835(2.1); 7.829(1.9); 7.674(1.8); 7.657(1.8); 7.654(1.9); 7.564(1.3); 7.559(1.6); 7.546(1.4); 7.544(1.5); 7.541(2.2); 7.516(0.7); 7.513(0.8); 7.497(1.7); 7.494(1.8); 7.487(0.8); 7.481(1.2); 7.479(1.4); 7.475(1.3); 7.468(2.2); 7.463(2.1); 7.452(2.5); 7.451(1.2); 7.447(2.4); 7.444(1.9); 7.434(2.1); 7.430(1.8); 7.415(0.7); 7.411(0.5); 7.383(2.1); 7.370(1.5); 7.365(1.7); 7.364(1.7); 7.351(2.0); 7.332(0.9); 7.307(0.3); 7.305(0.3); 2.553(2.7); 2.508(16.0); 2.154(4.8); 1.964(0.6); 1.958(0.7); 1.952(5.1); 1.946(9.5); 1.940(13.1); 1.933(8.9); 1.927(4.6); 1.477(0.9); 1.371(0.4); 1.338(0.7); 1.283(0.9); 1.275(0.5); 1.268(1.7); 0.000(6.2)
Example I-1-42:
HPLC-MS: mass (m/z): 351.0, 352.9
1H-NMR(400.0MHz, d6-DMSO): δ = 20.010(0.4); 19.941(0.4); 13.924(8.7); 8.624(8.4); 8.613(9.4); 8.314(1.9); 8.272(8.9); 8.253(9.3); 7.867(8.7); 7.863(7.2); 7.849(10.3); 7.844(8.0); 7.644(7.3); 7.632(13.5); 7.624(9.1); 7.613(16.0); 7.594(0.5); 7.556(4.0); 7.538(9.0); 7.513(11.6); 7.493(9.6); 7.476(3.2); 3.477(0.5); 3.454(0.6); 3.319(975.8); 2.670(7.6); 2.611(0.8); 2.505(1061.9); 2.501(1229.8); 2.328(7.3); 1.988(0.5); 1.234(0.6); 0.147(0.6); 0.000(78.7); −0.007(10.4); −0.150(0.5)
Example I-1-43:
HPLC-MS: mass (m/z): 385.0 (M + H)+
1H-NMR(400.0 MHz, d6-DMSO): δ = 14.023(11.0); 8.952(11.2); 8.940(11.2); 8.431(10.5); 8.411(11.2); 8.314(1.4); 7.944(9.2); 7.932(9.2); 7.924(8.9); 7.912(8.5); 7.875(10.8); 7.870(10.7); 7.856(13.1); 7.851(12.6); 7.638(9.5); 7.635(11.2); 7.619(13.7); 7.616(16.0); 7.559(5.1); 7.554(6.1); 7.541(12.3); 7.536(11.5); 7.522(9.2); 7.514(12.6); 7.510(10.8); 7.495(12.5); 7.492(12.3); 7.477(4.6); 7.473(4.1); 3.317(184.7); 3.188(0.4); 2.675(2.2); 2.671(3.1); 2.666(2.3); 2.524(7.6); 2.511(194.1); 2.506(402.4); 2.502(539.8); 2.497(396.0); 2.493(196.2); 2.333(2.2); 2.329(3.1); 2.324(2.4); 2.074(6.3); 0.000(16.8)
Example I-1-44:
HPLC-MS: mass (m/z): 386.0 (M + H)+
1H-NMR(400.0 MHz, d6-DMSO): δ = 14.210(4.2); 9.187(12.5); 9.181(16.0); 9.144(16.0); 9.138(12.6); 8.314(0.7); 7.897(8.0); 7.892(8.0); 7.878(9.3); 7.873(9.2); 7.644(7.2); 7.641(8.2); 7.625(10.7); 7.622(12.0); 7.566(3.7); 7.562(4.5); 7.548(9.1); 7.543(8.7); 7.529(6.7); 7.521(9.5); 7.517(8.0); 7.502(9.4); 7.499(9.1); 7.483(3.4); 7.480(3.1); 3.862(0.4); 3.322(180.2); 2.676(1.2); 2.672(1.7); 2.667(1.3); 2.507(211.4); 2.503(278.3); 2.498(207.3); 2.329(1.7); 2.325(1.2); 2.074(1.2); 0.000(8.8)
Example I-1-45:
HPLC-MS: mass (m/z): 347.1 (M + H)+
1H-NMR(400.0 MHz, d6-DMSO): δ = 13.160(1.7); 8.437(1.6); 8.432(1.7); 8.425(1.7); 8.420(1.7); 8.179(1.6); 8.174(1.6); 8.161(1.7); 8.156(1.6); 7.870(1.4); 7.865(1.3); 7.851(1.6); 7.846(1.5); 7.634(1.2); 7.631(1.4); 7.615(1.7); 7.611(1.9); 7.554(0.6); 7.549(0.8); 7.536(1.6); 7.531(1.5); 7.517(1.3); 7.511(2.3); 7.507(1.4); 7.492(1.6); 7.489(1.5); 7.474(0.6); 7.217(1.6); 7.205(1.6); 7.199(1.6); 7.186(1.6); 3.998(16.0); 3.961(0.6); 3.562(0.6); 3.321(161.3); 2.675(0.6); 2.671(0.9); 2.666(0.6); 2.541(6.1); 2.524(2.1); 2.510(51.7); 2.506(106.3); 2.501(146.4); 2.497(108.5); 2.493(51.9); 2.333(0.6); 2.328(0.8); 2.324(0.7); 0.000(6.3)
Example I-1-46:
HPLC-MS: mass (m/z): 435.1 (M + H)+
1H-NMR(400.0 MHz, d6-DMSO): δ = 13.977(10.4); 8.985(12.2); 8.973(12.3); 8.455(11.6); 8.436(12.4); 8.216(0.4); 8.197(0.4); 7.963(8.9); 7.951(9.1); 7.943(8.8); 7.931(8.2); 7.881(9.9); 7.876(10.5); 7.862(11.3); 7.858(11.5); 7.643(10.1); 7.640(11.0); 7.623(15.1); 7.620(16.0); 7.595(0.5); 7.563(5.0); 7.558(5.8); 7.544(12.2); 7.540(11.4); 7.525(9.3); 7.519(14.2); 7.514(10.8); 7.499(12.7); 7.496(12.0); 7.481(4.6); 7.478(4.0); 3.339(22.1); 2.678(0.5); 2.547(20.0); 2.512(59.8); 2.508(79.9); 2.335(0.5); 0.000(11.1)
Example I-1-47:
HPLC-MS: mass (m/z): 399.1 (M + H)+
1H-NMR(400.0 MHz, d6-DMSO): δ = 13.924(4.7); 8.814(8.3); 8.810(8.8); 8.802(9.0); 8.798(8.6); 8.306(8.0); 8.302(8.1); 8.287(8.9); 8.283(8.3); 7.880(7.5); 7.876(7.0); 7.862(9.2); 7.857(8.6); 7.644(13.1); 7.632(7.9); 7.624(16.0); 7.612(7.2); 7.561(2.9); 7.557(3.5); 7.543(7.4); 7.538(7.2); 7.524(6.1); 7.519(10.8); 7.500(7.7); 7.497(7.4); 7.482(2.7); 7.479(2.5); 4.198(4.1); 4.170(12.7); 4.143(13.2); 4.115(4.5); 3.342(11.8); 2.715(0.5); 2.675(0.4); 2.545(119.1); 2.528(1.2); 2.510(44.5); 2.506(60.4); 2.501(45.4); 2.372(0.5); 2.333(0.3); 0.000(6.4)
Example I-1-48:
HPLC-MS: mass (m/z): 345.2 (M + H)+
1H-NMR(400.0 MHz, d6-DMSO): δ = 13.759(3.5); 8.705(3.0); 8.701(3.1); 8.693(3.2); 8.688(3.0); 8.111(2.8); 8.107(2.7); 8.092(3.0); 8.088(2.8); 7.866(2.7); 7.861(2.5); 7.848(3.3); 7.843(3.1); 7.637(2.4); 7.634(2.7); 7.617(3.3); 7.614(3.8); 7.556(1.3); 7.551(1.5); 7.537(3.2); 7.532(2.9); 7.518(2.5); 7.513(4.3); 7.509(2.8); 7.495(3.2); 7.491(2.8); 7.476(1.1); 7.473(0.9); 7.439(2.6); 7.426(2.6); 7.419(2.5); 7.407(2.4); 3.483(0.3); 3.361(73.5); 2.962(1.9); 2.944(6.0); 2.925(6.2); 2.906(2.1); 2.676(0.8); 2.671(1.1); 2.666(0.9); 2.541(40.7); 2.524(3.0); 2.506(145.6); 2.502(199.2); 2.497(147.4); 2.328(1.1); 2.324(0.9); 1.258(7.7); 1.239(16.0); 1.220(7.3); 0.000(5.1)

TABLE 4-continued

Example I-1-49:
HPLC-MS: mass (m/z): 388.0 (M + H)⁺
$^1$H-NMR(400.0 MHz, d$_6$-DMSO): δ = 7.903(0.8); 7.889(1.1); 7.880(1.3); 7.823(1.3); 7.819(1.6); 7.810(3.4); 7.801(2.2); 7.797(1.5); 7.788(0.5); 7.777(1.6); 7.768(1.2); 7.755(0.7); 5.754(2.3); 4.716(0.9); 4.702(2.0); 4.689(1.0); 4.271(0.3); 4.259(0.4); 4.248(0.4); 3.418(0.6); 3.414(0.7); 3.401(1.6); 3.384(1.8); 3.371(0.8); 3.367(0.7); 3.318(88.1); 2.957(0.4); 2.945(0.4); 2.934(0.4); 2.735(2.3); 2.718(3.7); 2.702(1.9); 2.675(0.6); 2.670(0.9); 2.666(0.6); 2.592(16.0); 2.524(2.2); 2.510(48.8); 2.506(101.5); 2.501(135.8); 2.497(98.1); 2.492(46.9); 2.333(0.6); 2.328(0.8); 2.324(0.6); 2.222(2.4); 1.710(0.9); 1.234(0.7); 0.008(0.6); 0.000(16.4); −0.009(0.5)

Example I-1-50:
HPLC-MS: mass (m/z): 420.0 (M + H)⁺
$^1$H-NMR(400.0 MHz, d$_6$-DMSO): δ = 14.187(6.5); 9.181(16.0); 9.143(14.8); 8.314(1.2); 7.933(9.1); 7.913(11.5); 7.874(5.0); 7.855(13.2); 7.842(7.0); 7.824(10.2); 7.805(4.5); 7.778(6.3); 7.759(8.1); 7.740(3.1); 3.392(0.5); 3.318(369.4); 2.717(0.3); 2.671(4.7); 2.628(0.4); 2.502(774.4); 2.328(4.5); 2.073(1.8); 0.146(2.2); 0.051(0.3); 0.008(17.6); 0.000(459.4); −0.150(2.2)

Example I-1-51:
HPLC-MS: mass (m/z): 385.0 (M + H)⁺
$^1$H-NMR(400.0 MHz, d$_6$-DMSO): δ = 13.909(10.8); 8.631(7.8); 8.626(8.5); 8.619(8.4); 8.614(8.3); 8.314(0.7); 8.289(7.7); 8.285(8.0); 8.270(8.6); 8.266(8.2); 8.048(0.5); 7.928(7.3); 7.854(1.1); 7.849(2.3); 7.835(16.0); 7.819(8.6); 7.800(2.4); 7.773(3.9); 7.753(4.7); 7.737(2.3); 7.720(0.8); 7.648(8.1); 7.635(8.0); 7.629(7.8); 7.616(7.5); 3.354(113.6); 2.892(0.3); 2.732(0.4); 2.690(2.6); 2.676(1.4); 2.671(1.9); 2.667(1.5); 2.541(7.3); 2.524(5.6); 2.507(220.5); 2.502(304.9); 2.498(230.5); 2.333(1.2); 2.329(1.7); 2.325(1.2); 2.074(0.6); 1.299(0.5); 1.259(0.8); 1.235(3.2); 1.179(0.4); 0.854(0.5); 0.146(1.1); 0.008(9.4); 0.000(224.8); −0.008(8.7); −0.150(1.0)

Example I-1-52:
HPLC-MS: mass (m/z): 469.0 (M + H)⁺
$^1$H-NMR(400.0 MHz, d$_6$-DMSO): δ = 19.853(0.4); 13.944(4.2); 12.777(0.5); 12.741(0.8); 8.965(6.6); 8.957(6.6); 8.451(4.8); 8.434(4.9); 8.313(2.2); 8.199(0.6); 8.177(0.6); 8.132(6.1); 8.046(0.9); 7.945(4.4); 7.924(12.1); 7.905(10.4); 7.852(3.7); 7.832(16.0); 7.813(8.9); 7.794(3.6); 7.766(5.0); 7.747(6.5); 7.728(3.0); 7.623(0.5); 7.609(0.6); 3.576(0.4); 3.570(0.4); 3.505(0.5); 3.435(0.8); 3.407(0.9); 3.319(939.6); 3.219(1.0); 2.891(1.3); 2.767(0.4); 2.732(1.5); 2.670(7.0); 2.628(0.8); 2.506(892.2); 2.501(1141.4); 2.497(892.8); 2.328(6.5); 2.220(0.7); 2.205(0.6); 2.073(13.1); 1.235(0.4); 0.145(0.4); 0.000(81.9)

Example I-1-53:
HPLC-MS: mass (m/z): 365.1 (M + H)⁺
$^1$H-NMR(400.0 MHz, d$_6$-DMSO): δ = 13.915(1.2); 8.948(1.7); 8.935(1.7); 8.420(1.5); 8.401(1.6); 7.948(2.0); 7.940(1.5); 7.929(3.0); 7.920(1.3); 7.908(1.2); 7.413(0.4); 7.396(1.4); 7.380(2.1); 7.377(2.1); 7.366(2.8); 7.352(2.1); 7.333(1.5); 7.317(0.6); 7.312(0.6); 3.321(432.2); 2.675(1.1); 2.670(1.6); 2.666(1.2); 2.615(16.0); 2.510(87.6); 2.506(182.6); 2.501(256.5); 2.497(197.5); 2.493(99.0); 2.332(1.1); 2.328(1.5); 2.323(1.1); 2.073(0.6); 0.146(0.4); 0.008(3.8); 0.000(101.6); −0.008(4.0); −0.150(0.5)

Example I-1-54:
HPLC-MS: mass (m/z): 381.0 (M + H)⁺
$^1$H-NMR(400.0 MHz, d$_6$-DMSO): δ = 13.934(1.2); 8.944(1.4); 8.934(1.4); 8.412(1.3); 8.394(1.4); 8.392(1.4); 7.934(1.2); 7.922(1.2); 7.915(1.1); 7.903(1.1); 7.742(1.5); 7.738(1.6); 7.723(1.7); 7.719(1.6); 7.510(0.8); 7.506(0.7); 7.492(1.0); 7.489(1.2); 7.485(1.0); 7.471(1.0); 7.466(0.9); 7.196(2.0); 7.176(1.7); 7.083(1.1); 7.081(1.0); 7.064(1.9); 7.062(1.9); 7.046(0.9); 7.044(0.9); 3.818(16.0); 3.320(33.7); 2.524(0.7); 2.511(15.4); 2.507(31.2); 2.502(42.6); 2.498(31.4); 2.493(14.9)

Example I-1-55:
HPLC-MS: mass (m/z): 435.0 (M + H)⁺
$^1$H-NMR(400.0 MHz, d$_6$-DMSO): δ = 14.003(10.5); 11.225(1.1); 8.955(10.9); 8.945(10.6); 8.943(10.7); 8.439(10.1); 8.421(10.6); 8.420(10.6); 8.314(1.3); 8.113(13.4); 8.108(12.6); 8.093(15.2); 8.089(13.1); 7.946(9.3); 7.934(9.7); 7.926(8.8); 7.914(8.5); 7.694(4.7); 7.690(5.0); 7.675(9.8); 7.670(10.1); 7.655(10.3); 7.651(9.7); 7.602(8.1); 7.599(10.4); 7.583(11.9); 7.580(15.7); 7.563(16.0); 7.561(14.1); 7.542(8.0); 7.487(3.1); 7.467(4.6); 7.395(2.1); 7.392(2.2); 7.378(2.6); 7.375(3.7); 7.357(1.8); 7.354(1.8); 7.169(2.1); 7.167(2.2); 7.149(3.7); 7.132(1.7); 7.130(1.8); 3.321(308.9); 2.676(1.7); 2.672(2.4); 2.667(1.7); 2.525(6.3); 2.512(133.7); 2.507(277.5); 2.503(383.4); 2.498(285.0); 2.494(136.5); 2.339(0.8); 2.334(1.6); 2.330(2.3); 2.325(1.6); 2.074(1.7); 1.233(0.4); 0.000(2.5)

Example I-1-56:
HPLC-MS: mass (m/z): 387.0 (M + H)⁺
$^1$H-NMR(400.0 MHz, d$_6$-DMSO): δ = 14.037(1.0); 8.953(3.9); 8.943(3.9); 8.941(3.9); 8.425(3.5); 8.423(3.6); 8.406(3.9); 8.404(3.9); 8.188(1.8); 8.171(2.1); 8.166(3.7); 8.149(3.7); 8.144(2.2); 8.127(1.8); 7.945(3.4); 7.933(3.4); 7.926(3.2); 7.914(3.1); 7.475(1.9); 7.468(1.9); 7.451(2.2); 7.446(3.3); 7.440(2.1); 7.423(1.9); 7.417(2.0); 7.294(1.6); 7.289(1.5); 7.274(3.0); 7.268(2.8); 7.252(1.5); 7.246(1.4); 3.324(39.4); 2.678(0.4); 2.673(0.5); 2.669(0.3); 2.527(1.4); 2.513(28.4); 2.509(57.9); 2.504(79.3); 2.500(58.6); 2.495(27.9); 2.336(0.4); 2.331(0.5); 2.326(0.3); 2.076(16.0); 0.000(0.5)

Example I-1-57:
HPLC-MS: mass (m/z): 369.0 (M + H)⁺
$^1$H-NMR(400.0 MHz, d$_6$-DMSO): δ = 14.038(7.5); 8.952(11.4); 8.942(11.3); 8.940(11.1); 8.428(10.2); 8.426(10.5); 8.408(11.3); 8.406(11.1); 8.314(1.2); 8.134(0.4); 8.116(5.7); 8.111(6.1); 8.096(11.5); 8.092(12.2); 8.083(1.6); 8.076(6.5); 8.072(6.3); 7.944(9.7); 7.932(9.7); 7.925(9.3); 7.913(8.8); 7.610(2.8); 7.605(3.1); 7.597(3.4); 7.592(5.9); 7.587(5.9); 7.585(4.8); 7.578(6.0); 7.575(5.4); 7.571(6.7); 7.566(4.3); 7.558(4.0); 7.554(3.7); 7.411(8.3); 7.389(15.2); 7.385(11.0); 7.382(8.1); 7.371(16.0); 7.364(7.8); 7.361(6.6); 7.352(8.3); 7.350(6.8); 6.521(0.4); 5.755(0.9); 3.321(155.6); 2.677(1.5); 2.672(2.0); 2.668(1.5); 2.526(6.0); 2.512(121.8); 2.508(244.2); 2.503(330.5); 2.499(243.4); 2.494(115.6); 2.335(1.4); 2.330(1.9); 2.325(1.4); 0.000(1.9)

Example I-1-58:
HPLC-MS: mass (m/z): 379.1 (M + H)⁺
$^1$H-NMR(400.0 MHz, d$_6$-DMSO): δ = 13.898(2.9); 8.953(2.6); 8.941(2.6); 8.434(2.4); 8.416(2.6); 8.314(0.5); 7.945(2.2); 7.933(2.2); 7.925(2.1); 7.913(2.0); 7.865(2.6); 7.862(2.8); 7.845(2.9); 7.843(2.9); 7.452(0.9); 7.448(0.9); 7.433(2.4); 7.430(2.4); 7.415(2.6); 7.412(2.6); 7.389(4.0); 7.373(1.7); 7.348(1.9); 7.345(1.7); 7.330(2.6); 7.326(2.3); 7.311(1.2); 7.308(1.1); 3.318(148.7); 3.046(1.6); 3.027(5.2); 3.009(5.3); 2.990(1.7); 2.675(0.8); 2.671(1.1); 2.666(0.8); 2.524(2.8); 2.511(62.4); 2.506(129.1); 2.502(178.4); 2.497(133.0); 2.493(63.9); 2.333(0.8); 2.329(1.1); 2.324(0.8); 2.073(0.8); 1.165(7.2); 1.146(16.0); 1.127(7.1); 0.000(1.4)

Example I-1-59:
HPLC-MS: mass (m/z): 393.1 (M + H)⁺
$^1$H-NMR(400.0 MHz, d$_6$-DMSO): δ = 13.897(1.2); 8.947(1.5); 8.936(1.5); 8.431(1.3); 8.411(1.4); 7.939(1.2); 7.927(1.2); 7.919(1.2); 7.907(1.1); 7.696(1.6); 7.694(1.7); 7.677(1.9); 7.674(1.8); 7.514(0.9); 7.498(2.3); 7.494(2.3); 7.485(1.4); 7.482(1.3); 7.468(1.5); 7.465(1.6); 7.448(0.6); 7.445(0.6); 7.322(1.1); 7.318(1.1); 7.303(1.5); 7.285(0.8); 7.281(0.8); 5.753(3.3); 3.767(0.3); 3.749(0.9); 3.732(1.2); 3.715(0.9); 3.698(0.4); 3.318(83.1); 2.675(0.5); 2.671(0.7); 2.666(0.5); 2.524(1.6); 2.511(35.9); 2.506(75.5); 2.501(105.2); 2.497(77.7); 2.493(36.7); 2.333(0.5); 2.328(0.6); 2.324(0.4); 1.207(16.0); 1.190(15.9); 0.000(5.9)

TABLE 4-continued

Example I-1-60:
HPLC-MS: mass (m/z): 437.0 (M + H)+
1H-NMR(400.0 MHz, d6-DMSO): δ = 14.067(0.5); 14.013(6.2); 8.944(10.5); 8.932(10.7); 8.434(9.3); 8.414(10.0); 8.313(1.8); 7.954(7.8); 7.933(13.8); 7.917(16.0); 7.904(7.3); 7.849(8.4); 7.843(9.5); 7.826(8.6); 7.820(9.4); 7.801(0.4); 7.793(0.4); 7.724(5.3); 7.717(5.0); 7.703(9.4); 7.697(8.7); 7.682(4.4); 7.675(4.1); 7.514(0.4); 7.493(0.4); 7.199(0.6); 7.071(0.5); 6.945(0.5); 3.419(0.4); 3.320(828.4); 3.239(0.4); 2.891(2.9); 2.732(2.6); 2.690(1.1); 2.676(3.3); 2.671(4.6); 2.667(3.5); 2.524(10.0); 2.511(260.7); 2.506(560.6); 2.502(793.5); 2.497(596.2); 2.493(289.3); 2.427(0.4); 2.400(0.3); 2.369(0.3); 2.333(3.4); 2.329(4.7); 2.324(3.5); 0.008(0.5); 0.000(12.4); −0.009(0.5)
Example I-1-61:
HPLC-MS: mass (m/z): 437.0 (M + H)+
1H-NMR(400.0 MHz, d6-DMSO): δ = 18.495(0.4); 15.214(0.4); 14.096(0.5); 14.084(0.7); 14.030(7.5); 13.955(0.4); 8.973(0.4); 8.933(12.1); 8.922(12.2); 8.428(10.2); 8.408(11.0); 8.313(3.8); 8.132(1.1); 7.978(0.5); 7.952(0.9); 7.925(9.1); 7.913(9.7); 7.905(9.3); 7.893(8.4); 7.884(5.0); 7.864(9.5); 7.851(9.6); 7.845(6.9); 7.830(5.7); 7.819(0.4); 7.703(8.0); 7.675(8.8); 7.653(6.4); 7.558(16.0); 7.540(14.1); 7.195(0.7); 7.085(0.4); 7.070(0.6); 6.941(0.6); 3.454(0.4); 3.442(0.4); 3.416(0.4); 3.408(0.5); 3.317(826.6); 3.249(0.5); 2.891(3.5); 2.731(3.1); 2.690(3.1); 2.675(5.8); 2.671(8.0); 2.666(5.9); 2.635(0.5); 2.524(17.9); 2.519(29.0); 2.511(451.3); 2.506(961.8); 2.502(1349.3); 2.497(1000.9); 2.493(474.9); 2.439(0.6); 2.422(0.5); 2.390(0.4); 2.361(0.4); 2.337(2.8); 2.333(5.8); 2.328(7.9); 2.324(5.8); 2.319(2.8); 2.251(0.4); 1.755(0.4); 1.243(0.4); 0.000(16.0)
Example I-1-62:
See Synthesis Example 11
Example I-1-63:
HPLC-MS: mass (m/z): 418.9; 420.9 (M + H)+
1H-NMR(400.0 MHz, d6-DMSO): δ = 14.035(3.0); 12.753(1.2); 8.924(2.0); 8.444(1.8); 8.312(7.8); 8.130(2.3); 7.965(1.1); 7.900(2.1); 7.748(1.0); 7.638(5.3); 7.619(8.3); 7.577(3.3); 7.560(2.9); 6.512(6.3); 4.074(1.2); 3.534(1.0); 3.314(1368.5); 3.278(3.9); 3.259(1.7); 2.891(1.2); 2.730(1.5); 2.674(11.9); 2.670(16.0); 2.666(12.7); 2.602(1.7); 2.509(980.8); 2.505(2041.9); 2.501(2876.5); 2.496(2202.0); 2.403(1.3); 2.348(1.4); 2.332(11.9); 2.328(15.9); 2.323(12.0); 2.300(1.2); 0.000(75.1)
Example I-1-64:
HPLC-MS: mass (m/z): 437.1 (M + H)+
1H-NMR(400.0 MHz, d6-DMSO): δ = 14.049(16.0); 8.952(14.0); 8.940(14.1); 8.442(12.9); 8.423(13.5); 8.313(4.7); 8.025(10.0); 8.012(10.0); 8.004(10.8); 7.990(10.5); 7.942(10.6); 7.930(10.7); 7.923(10.5); 7.911(9.7); 7.738(9.3); 7.732(11.0); 7.715(10.0); 7.709(10.6); 7.639(5.3); 7.633(5.0); 7.618(9.8); 7.596(5.1); 7.499(0.8); 7.406(0.6); 3.524(0.7); 3.460(0.9); 3.396(0.8); 3.315(1531.8); 3.256(0.8); 2.721(0.7); 2.670(12.3); 2.666(10.1); 2.631(0.9); 2.605(1.2); 2.569(1.9); 2.506(1446.8); 2.501(2088.1); 2.497(1661.7); 2.440(1.0); 2.333(8.5); 2.328(12.0); 2.324(9.3); 2.086(0.7); 1.398(12.0); 1.237(1.4); 1.227(0.7); 0.146(10.0); 0.008(82.1); 0.000(2296.1); −0.008(104.1); −0.024(3.1); −0.066(0.8); −0.150(10.1)
Example I-1-65:
See Synthesis Example 12
Example I-1-66:
See Synthesis Example 12
Example I-1-67:
See Synthesis Example 13
Example I-1-68:
HPLC-MS: mass (m/z): 364.1 (M + H)+
1H-NMR(400.0 MHz, d6-DMSO): δ = 7.946(2.2); 7.927(2.5); 7.903(0.8); 7.885(2.0); 7.874(1.0); 7.856(1.6); 7.834(1.4); 7.8131.1); 7.795(0.4); 7.411(0.4); 7.392(1.2); 7.378(1.5); 7.375(1.9); 7.363(2.5); 7.349(1.6); 7.332(1.3); 7.312(0.5); 3.379(193.6); 3.366(121.8); 2.679(0.3); 2.674(0.4); 2.613(16.0); 2.528(1.0); 2.514(26.6); 2.510(55.6); 2.506(74.4); 2.501(53.3); 2.497(25.3); 2.332(0.4)
Example I-1-69:
HPLC-MS: mass (m/z): 436.0 (M + H)+
1H-NMR(400.0 MHz, d6-DMSO): δ = 13.929(8.0); 8.314(0.7); 8.024(8.4); 8.011(8.8); 8.002(9.4); 7.989(9.1); 7.950(9.2); 7.932(13.4); 7.928(15.1); 7.922(8.4); 7.904(14.2); 7.879(5.7); 7.864(12.2); 7.842(13.3); 7.822(8.6); 7.804(2.8); 7.735(7.9); 7.728(8.9); 7.712(8.2); 7.705(8.6); 7.637(4.5); 7.631(3.9); 7.616(8.1); 7.610(6.8); 7.595(4.1); 7.588(3.4); 3.324(376.2); 2.677(1.2); 2.672(1.6); 2.667(1.2); 2.525(3.8); 2.512(92.4); 2.507(197.2); 2.503(277.4); 2.498(205.2); 2.494(96.8); 2.334(1.2); 2.330(1.6); 2.325(1.1); 2.074(16.0); 0.146(0.9); 0.008(6.3); 0.000(205.6); −0.008(6.6); −0.150(0.9)
Example I-1-70:
HPLC-MS: mass (m/z): 434.0 (M + H)+
1H-NMR(400.0 MHz, d6-DMSO): δ = 13.884(10.8); 8.316(0.4); 8.111(10.5); 8.107(11.3); 8.092(11.8); 8.087(11.8); 7.946(8.8); 7.925(14.9); 7.901(13.6); 7.879(5.6); 7.863(11.3); 7.841(11.2); 7.819(8.2); 7.801(2.7); 7.690(4.0); 7.685(4.3); 7.670(9.7); 7.666(9.9); 7.651(8.8); 7.646(8.4); 7.597(9.1); 7.578(13.8); 7.559(16.0); 7.538(7.8); 7.051(0.7); 3.324(136.0); 2.678(0.7); 2.673(1.0); 2.669(0.7); 2.526(2.2); 2.508(122.6); 2.504(170.1); 2.500(127.5); 2.331(1.0); 2.327(0.8); 2.076(1.7); 1.234(0.7); 1.216(0.8); 1.208(1.1); 1.191(1.0); 0.896(0.7); 0.879(0.7); 0.146(0.6); 0.008(3.9); 0.000(117.7); −0.008(4.3); −0.150(0.6)
Example I-1-71:
HPLC-MS: mass (m/z): 386.0 (M + H)+
1H-NMR(400.0 MHz, d6-DMSO): δ = 13.899(11.4); 8.313(1.5); 8.179(5.1); 8.162(6.3); 8.157(10.9); 8.140(10.8); 8.135(6.7); 8.118(5.5); 8.093(0.5); 7.941(10.0); 7.922(13.8); 7.905(6.9); 7.887(6.8); 7.874(7.0); 7.858(13.1); 7.835(11.5); 7.813(8.9); 7.795(3.1); 7.484(0.5); 7.469(5.3); 7.463(5.8); 7.445(6.0); 7.440(9.6); 7.435(6.4); 7.417(5.2); 7.411(5.3); 7.374(0.4); 7.291(4.9); 7.285(4.8); 7.270(9.1); 7.264(8.7); 7.249(4.7); 7.243(4.5); 7.148(0.4); 3.320(1090.3); 2.676(3.2); 2.671(4.5); 2.667(3.4); 2.524(11.0); 2.506(540.9); 2.502(757.5); 2.498(576.4); 2.333(3.1); 2.329(4.3); 2.324(3.2); 1.235(0.4); 1.216(0.4); 0.146(1.8); 0.008(12.7); 0.000(376.4); −0.008(13.9); −0.150(1.8)
Example I-1-72:
HPLC-MS: mass (m/z): 380.0 (M + H)+
1H-NMR(400.0 MHz, d6-DMSO): δ = 13.791(1.8); 7.934(1.2); 7.916(1.6); 7.890(0.7); 7.871(2.0); 7.849(1.6); 7.826(1.4); 7.806(1.0); 7.788(0.4); 7.731(1.5); 7.727(1.6); 7.712(1.6); 7.708(1.7); 7.505(0.7); 7.500(0.7); 7.482(1.3); 7.480(1.1); 7.466(0.9); 7.461(0.9); 7.191(2.1); 7.170(1.8); 7.078(1.1); 7.059(2.0); 7.042(0.9); 7.040(1.0); 3.815(16.0); 3.318(36.1); 2.524(0.8); 2.510(17.7); 2.506(36.9); 2.502(51.4); 2.497(39.2); 2.493(19.4); 0.008(2.4); 0.000(69.6); −0.008(2.7)
Example I-1-73:
HPLC-MS: mass (m/z): 368.0 (M + H)+
1H-NMR(400.0 MHz, d6-DMSO): δ = 13.899(14.7); 8.315(0.7); 8.109(5.3); 8.105(5.9); 8.090(10.3); 8.086(11.4); 8.070(5.7); 8.066(6.0); 7.943(9.7); 7.924(13.5); 7.911(7.1); 7.893(15.1); 7.876(6.4); 7.860(12.4); 7.838(11.5); 7.816(8.9); 7.798(2.9); 7.605(2.5); 7.601(2.7); 7.593(2.9); 7.587(5.6); 7.584(5.7); 7.573(5.7); 7.567(6.5); 7.562(4.1); 7.554(3.6); 7.550(3.3); 7.407(8.2); 7.386(16.0); 7.381(10.2); 7.368(15.8); 7.360(7.3); 7.349(7.2); 3.319(155.0); 2.672(2.0); 2.542(3.0); 2.507(246.6); 2.503(339.8); 2.499(266.8); 2.330(1.9); 1.235(1.3); 0.146(2.0); 0.008(15.4); 0.000(392.5); −0.149(1.9)

TABLE 4-continued

Example I-1-74:
HPLC-MS: mass (m/z): 392.1 (M + H)⁺
$^1$H-NMR(400.0 MHz, d$_6$-DMSO): δ = 13.771(2.3); 7.943(1.4); 7.921(2.3); 7.899(2.1); 7.874(0.8); 7.858(1.7); 7.835(1.7); 7.814(1.3); 7.795(0.4); 7.693(1.8); 7.676(2.0); 7.673(1.9); 7.510(1.0); 7.494(2.5); 7.491(2.5); 7.482(1.4); 7.479(1.4); 7.462(1.7); 7.445(0.6); 7.320(1.1); 7.316(1.1); 7.300(1.6); 7.283(0.8); 7.279(0.8); 3.765(0.4); 3.748(1.0); 3.731(1.3); 3.714(1.0); 3.696(0.4); 3.317(92.1); 2.675(0.5); 2.671(0.7); 2.666(0.5); 2.524(1.8); 2.506(86.6); 2.501(120.4); 2.497(91.7); 2.332(0.5); 2.328(0.7); 2.324(0.5); 1.235(0.5); 1.207(16.0); 1.190(15.9); 0.146(0.7); 0.008(4.8); 0.000(146.0); −0.008(5.8); −0.150(0.7)

Example I-1-75:
HPLC-MS: mass (m/z): 436.0 (M + H)⁺
$^1$H-NMR(400.0 MHz, d$_6$-DMSO): δ = 13.888(11.0); 8.313(0.9); 7.948(8.7); 7.937(6.5); 7.928(16.0); 7.902(10.4); 7.876(4.0); 7.860(8.8); 7.848(7.5); 7.842(15.3); 7.825(8.1); 7.819(13.2); 7.800(2.1); 7.725(3.8); 7.718(3.5); 7.704(6.7); 7.697(6.0); 7.683(3.2); 7.676(2.8); 3.319(255.2); 2.676(1.4); 2.671(2.0); 2.667(1.4); 2.525(5.0); 2.511(114.9); 2.507(240.3); 2.502(334.2); 2.498(248.7); 2.493(118.9); 2.333(1.4); 2.329(2.0); 2.324(1.4); 1.398(2.0); 1.236(0.8); 0.146(2.0); 0.008(15.3); 0.000(459.6); −0.009(16.0); −0.150(2.0)

Example I-1-76:
HPLC-MS: mass (m/z): 436.0 (M + H)⁺
$^1$H-NMR(400.0 MHz, d$_6$-DMSO): δ = 13.905(12.9); 8.314(1.8); 7.946(8.0); 7.925(16.0); 7.905(12.4); 7.889(3.4); 7.870(8.1); 7.856(16.0); 7.836(15.6); 7.817(7.3); 7.800(2.3); 7.711(6.0); 7.690(5.3); 7.682(6.4); 7.661(4.8); 7.561(11.5); 7.542(10.2); 3.732(0.8); 3.318(789.3); 2.675(3.9); 2.671(5.3); 2.666(3.9); 2.611(0.6); 2.575(1.0); 2.524(14.6); 2.511(303.2); 2.506(631.6); 2.502(876.1); 2.497(651.1); 2.493(309.5); 2.333(3.6); 2.329(5.0); 2.324(3.6); 1.398(1.4); 1.236(4.6); 1.192(0.4); 0.854(0.7); 0.146(5.2); 0.060(0.4); 0.008(40.0); 0.000(1180.2); −0.008(40.7); −0.150(5.1)

Example I-1-77:
HPLC-MS: mass(m/z): 420.0 (M + H)⁺
$^1$H-NMR(400.0 MHz, d$_6$-DMSO): δ = 13.972(9.9); 8.315(0.4); 7.956(4.9); 7.936(6.9); 7.874(3.3); 7.854(7.6); 7.834(6.5); 7.823(8.1); 7.805(3.2); 7.679(1.2); 7.658(3.2); 7.641(5.4); 7.621(3.5); 7.604(1.4); 7.317(9.1); 7.296(16.0); 7.275(7.7); 7.206(0.9); 7.079(1.0); 6.950(0.9); 3.319(518.0); 2.670(4.6); 2.638(0.4); 2.501(750.0); 2.497(611.0); 2.328(4.3); 2.074(2.5); 1.235(0.3); 0.146(0.7); 0.000(132.2); −0.150(0.7)

Example I-1-78:
See Synthesis Example 13

Example I-2-1:
HPLC-MS: mass (m/z): 420.9 (M + H)⁺
$^1$H-NMR(400.0 MHz, d$_6$-DMSO): δ = 14.207(6.4); 9.104(9.3); 9.102(9.0); 8.825(0.4); 8.717(9.3); 8.713(9.0); 7.773(1.3); 7.756(2.8); 7.752(2.6); 7.735(5.1); 7.718(2.7); 7.714(3.0); 7.697(1.3); 7.371(9.1); 7.350(16.0); 7.330(7.7); 7.233(0.5); 7.212(0.7); 5.758(1.6); 4.022(0.3); 3.490(0.5); 3.472(0.5); 3.329(18.9); 3.166(0.4); 3.148(0.4); 3.027(0.4); 2.679(0.4); 2.674(0.5); 2.670(0.4); 2.544(0.4); 2.527(1.7); 2.514(31.6); 2.510(62.9); 2.505(82.0); 2.501(58.4); 2.496(27.6); 2.336(0.4); 2.332(0.5); 2.327(0.4); 1.991(1.4); 1.357(1.2); 1.232(1.6); 1.194(0.4); 1.177(0.8); 1.165(0.6); 1.159(0.4); 1.147(1.2); 1.129(0.6); 1.025(0.5); 1.008(1.0); 0.990(0.5); 0.000(3.7)

Example I-2-2:
HPLC-MS: mass (m/z): 452.9 (M + H)⁺
$^1$H-NMR(400.0 MHz, d$_6$-DMSO): δ = 14.028(13.4); 9.117(0.6); 9.101(15.2); 9.098(15.2); 8.822(0.4); 8.715(15.5); 8.712(15.1); 8.317(0.6); 7.960(8.1); 7.939(16.0); 7.919(12.1); 7.892(5.0); 7.876(10.4); 7.858(7.1); 7.853(9.3); 7.848(8.0); 7.830(7.8); 7.811(3.1); 7.789(0.8); 7.736(0.7); 7.719(0.5); 7.656(0.4); 7.636(0.6); 7.461(0.6); 7.442(0.6); 3.326(105.2); 3.066(0.3); 2.677(1.1); 2.672(1.5); 2.668(1.1); 2.663(0.6); 2.542(1.5); 2.525(6.0); 2.512(89.4); 2.508(179.0); 2.503(235.8); 2.498(168.6); 2.494(80.8); 2.334(1.0); 2.330(1.4); 2.325(1.0); 2.321(0.5); 1.990(1.2); 1.730(0.4); 1.234(0.8); 1.193(0.4); 1.176(0.7); 1.158(0.4); 1.139(1.5); 1.121(3.2); 1.103(1.5); 1.001(1.5); 0.983(3.3); 0.965(1.5); 0.000(0.9)

Example I-2-3:
HPLC-MS: mass (m/z): 453.9 (M + H)⁺
$^1$H-NMR(400.0 MHz, d$_6$-DMSO): δ = 14.160(8.2); 9.104(15.6); 9.101(15.3); 8.966(10.0); 8.956(9.7); 8.954(9.8); 8.825(0.3); 8.719(16.0); 8.716(15.2); 8.454(9.3); 8.437(9.9); 8.434(9.8); 8.317(0.7); 7.962(8.6); 7.950(8.6); 7.942(8.3); 7.930(7.9); 5.757(6.0); 3.327(61.6); 2.677(1.2); 2.672(1.6); 2.668(1.2); 2.542(1.2); 2.525(5.5); 2.512(98.1); 2.508(195.7); 2.503(255.6); 2.499(182.1); 2.494(86.4); 2.334(1.2); 2.330(1.6); 2.325(1.2); 2.076(3.1); 1.234(0.4); 1.196(0.4); 1.178(0.7); 1.159(0.4); 0.008(2.4); 0.000(60.7); −0.009(2.0)

Example I-2-4:
HPLC-MS: mass (m/z): 385.0 (M + H)⁺
$^1$H-NMR(400.0 MHz, d$_6$-DMSO): δ = 13.995(0.4); 13.928(13.3); 13.894(0.4); 8.670(12.3); 8.659(11.8); 8.315(1.2); 8.276(0.4); 8.153(11.1); 8.132(11.8); 8.082(0.4); 7.951(9.0); 7.931(15.2); 7.909(12.8); 7.885(5.6); 7.866(10.5); 7.843(9.0); 7.821(7.9); 7.801(2.6); 7.745(0.3); 7.705(0.4); 7.654(0.5); 7.623(9.0); 7.611(9.0); 7.602(8.3); 7.591(7.4); 7.520(0.4); 4.197(0.3); 4.056(1.5); 4.038(4.0); 4.020(4.0); 4.002(1.5); 3.883(0.4); 3.745(0.5); 3.599(0.7); 3.571(0.4); 3.495(0.4); 3.477(0.4); 3.466(0.4); 3.376(0.7); 3.319(167.1); 3.055(0.3); 2.998(0.4); 2.891(0.7); 2.785(0.5); 2.767(0.5); 2.731(0.8); 2.671(5.3); 2.624(1.0); 2.505(747.9); 2.501(820.6); 2.328(4.4); 1.989(16.0); 1.900(0.3); 1.637(0.3); 1.398(1.7); 1.332(0.3); 1.298(0.8); 1.276(1.3); 1.260(1.8); 1.237(2.7); 1.193(4.6); 1.175(8.6); 1.158(4.3); 1.122(0.5); 1.029(0.3); 0.855(0.7); 0.792(0.3); 0.146(0.7); 0.004(73.3); 0.000(134.9); −0.149(0.6)

Example I-2-5:
HPLC-MS: mass (m/z): 386.9 (M + H)⁺
$^1$H-NMR(400.0 MHz, d$_6$-DMSO): δ = 14.078(1.2); 14.061(4.0); 8.956(3.9); 8.947(3.8); 8.811(0.9); 8.800(1.1); 8.670(5.6); 8.662(5.5); 8.659(5.6); 8.445(3.1); 8.425(3.5); 8.314(6.5); 8.156(4.9); 8.133(5.3); 8.023(0.8); 7.952(2.9); 7.939(3.1); 7.931(2.7); 7.919(2.6); 7.807(1.2); 7.777(0.9); 7.627(4.5); 7.616(4.1); 7.606(4.0); 7.595(4.0); 3.462(0.9); 3.446(0.9); 3.428(0.9); 3.404(0.9); 3.319(1110.5); 3.184(1.4); 2.748(1.0); 2.732(1.4); 2.675(11.6); 2.670(16.0); 2.666(12.0); 2.540(9.3); 2.524(45.3); 2.510(928.6); 2.506(1932.5); 2.501(2683.3); 2.497(2033.1); 2.493(1006.0); 2.333(10.8); 2.328(15.3); 2.324(11.4); 2.074(0.9); 1.237(1.1); 1.193(1.7); 1.175(2.9); 1.158(1.8); 1.100(2.8); 1.084(3.2); 1.072(2.7); 0.935(1.4); 0.000(12.2)

Example I-2-6:
See Synthesis Example 15

Example I-2-7:
HPLC-MS: mass (m/z): 388.0 (M + H)⁺
$^1$H-NMR(400.0 MHz, d$_6$-DMSO): δ = 14.117(6.5); 8.961(9.4); 8.949(9.4); 8.685(15.6); 8.679(16.0); 8.435(8.8); 8.416(9.4); 8.196(5.0); 8.190(4.8); 8.174(5.5); 8.169(8.2); 8.164(5.3); 8.147(5.0); 8.141(4.7); 7.955(7.9); 7.943(7.9); 7.936(7.5); 7.924(7.2); 3.322(316.5); 3.052(1.5); 3.016(1.0); 2.753(1.0); 2.676(1.4); 2.672(1.9); 2.667(1.4); 2.641(0.4); 2.525(4.9); 2.511(106.7); 2.507(227.4); 2.502(321.3); 2.498(245.0); 2.494(119.7); 2.334(1.3); 2.329(1.8); 2.325(1.3); 2.075(6.7); 1.168(0.3); 1.151(0.3); 0.146(0.4); 0.008(2.9); 0.000(88.7); −0.009(3.2); −0.150(0.4)

TABLE 4-continued

Example I-3-1:
HPLC-MS: mass (m/z): 385.0 (M + H)$^+$
$^1$H-NMR(400.0 MHz, d$_6$-DMSO): δ = 13.972(16.0); 8.577(12.3); 8.573(13.6); 8.565(13.9); 8.561(13.6); 8.318(12.7); 8.313(12.8);
8.299(14.3); 8.294(13.4); 7.951(9.6); 7.933(14.0); 7.921(8.8); 7.904(15.2); 7.883(6.8); 7.867(12.6); 7.845(13.2); 7.824(9.7); 7.806(3.6);
7.627(12.5); 7.615(12.8); 7.608(12.9); 7.596(12.2); 3.325(92.0); 2.673(1.2); 2.543(2.4); 2.508(149.9); 2.504(199.6); 2.500(157.3); 2.331(1.2);
2.076(0.4); 1.531(0.4); 0.146(0.6); 0.000(138.3); −0.150(0.6)
Example I-3-2:
HPLC-MS: mass (m/z): 386.0 (M + H)$^+$
$^1$H-NMR(400.0 MHz, d$_6$-DMSO): δ = 14.104(14.2); 8.960(12.5); 8.948(12.5); 8.689(0.3); 8.678(0.4); 8.581(14.0); 8.577(15.4); 8.569(15.1);
8.565(15.2); 8.440(11.8); 8.421(12.5); 8.326(14.5); 8.321(14.8); 8.307(16.0); 8.302(15.1); 7.953(10.5); 7.941(10.5); 7.933(10.1);
7.921(9.6); 7.888(0.4); 7.706(0.3); 7.631(15.2); 7.619(14.8); 7.611(14.7); 7.600(14.3); 3.327(68.1); 2.677(1.2); 2.673(1.6); 2.668(1.2);
2.643(2.3); 2.543(1.0); 2.526(4.6); 2.512(94.9); 2.508(197.5); 2.504(275.6); 2.499(209.1); 2.495(103.3); 2.335(1.2); 2.331(1.6); 2.326(1.2);
2.076(10.3); 1.169(2.5); 1.152(2.4); 1.102(0.5); 0.146(1.0); 0.008(8.0); 0.000(222.7); −0.008(8.9); −0.150(1.0)
Example I-3-3:
HPLC-MS: mass(m/z): 351.9, 353.8
1H-NMR(400.0 MHz, d$_6$-DMSO): δ = 14.004(10.3); 8.633(10.6); 8.628(11.4); 8.621(11.3); 8.616(11.2); 8.578(11.5); 8.573(12.4);
8.566(12.3); 8.562(12.0); 8.317(12.8); 8.312(12.5); 8.298(13.8); 8.293(12.8); 8.280(11.4); 8.275(11.4); 8.261(12.4); 8.256(11.7); 7.651(11.0);
7.639(11.1); 7.630(15.8); 7.618(16.0); 7.610(12.0); 7.598(11.4); 3.323(190.0); 2.672(2.6); 2.667(2.0); 2.525(8.0); 2.507(319.4);
2.503(432.2); 2.498(326.6); 2.334(1.8); 2.330(2.5); 2.325(1.9); 2.075(2.5); 0.146(0.7); 0.008(5.7); 0.000(145.6); −0.007(5.3); −0.150(0.7)
Example I-3-4:
HPLC-MS: mass(m/z): 409.0(M + H)$^+$
$^1$H-NMR(400.0 MHz, d$_6$-DMSO): δ = 16.430(0.7); 14.043(12.5); 12.248(0.8); 8.564(10.6); 8.553(10.9); 8.314(5.0); 8.304(10.7); 8.285(11.3);
8.140(1.0); 7.615(7.7); 7.601(9.2); 7.584(7.5); 5.755(3.1); 4.464(16.0); 3.504(0.9); 3.476(0.8); 3.394(1.5); 3.321(845.6); 3.263(1.2);
3.087(0.8); 2.914(0.7); 2.821(0.8); 2.754(0.9); 2.732(1.0); 2.712(1.1); 2.671(13.0); 2.647(1.4); 2.561(4.8); 2.541(53.9); 2.502(2145.6);
2.328(12.0); 2.075(1.2); 1.235(2.5); 0.147(2.5); 0.000(535.5); −0.048(0.8); −0.150(2.6)
Example I-3-5:
HPLC-MS: mass(m/z): 442.9, 444.9
$^1$H-NMR(400.0 MHz, d$_6$-DMSO): δ = 20.002(0.6); 13.793(12.8); 8.573(11.9); 8.569(12.6); 8.562(12.5); 8.557(12.6); 8.311(13.0);
8.306(12.8); 8.292(13.7); 8.287(12.9); 8.208(0.8); 8.190(0.9); 8.017(14.3); 7.998(15.0); 7.762(0.6); 7.671(9.5); 7.667(10.0); 7.652(14.5);
7.648(14.0); 7.624(12.6); 7.612(13.5); 7.605(12.6); 7.593(12.1); 7.579(8.0); 7.561(14.0); 7.542(6.7); 7.346(6.2); 7.342(6.3); 7.323(10.2);
7.308(5.1); 7.304(5.0); 3.471(0.6); 3.321(991.2); 2.786(0.6); 2.739(0.6); 2.675(8.5); 2.671(11.0); 2.666(8.3); 2.619(1.3); 2.541(13.6);
2.506(1401.2); 2.502(1904.3); 2.497(1434.7); 2.333(8.0); 2.328(10.9); 2.324(8.0); 2.074(16.0); 0.146(2.9); 0.008(25.4);
0.000(624.4); −0.008(22.5); −0.149(2.5)

BIOLOGICAL EXAMPLES

*Ctenocephalides felis*—In-Vitro Contact Tests Adult Cat Flea 9 mg compound is solved in 1 ml acetone and diluted with acetone to the desired concentration. 250 µl of the test solution is filled in 25 ml glass test tubes and homogeneously distributed on the inner walls by rotation and tilting on a shaking device (2 h at 30 rpm). With a compound concentration of 900 ppm, an inner surface of 44.7 cm$^2$ and a homogeneous distribution, a dose of 5 µg/cm$^2$ is achieved.

After the solvent has evaporated, each test tube is filled with 5-10 adult cat fleas (*Ctenocephalides felis*), closed with a perforated lid and incubated in a lying position at room temperature and relative humidity. After 48 hours efficacy is determined. The fleas are patted on the ground of the tubes and are incubated on a heating plate at 45-50° C. for at most 5 minutes. Immotile or uncoordinated moving fleas, which are not able to escape the heat by climbing upwards, are marked as dead or moribund.

A compound shows a good efficacy against *Ctenocephalides felis*, if at a compound concentration of 5 µg/cm$^2$ an efficacy of at least 80% is monitored. An efficacy of 100% means all fleas are dead or moribund; 0% means no fleas are dead or moribund.

In this test, for example, the following compounds from the preparation examples showed good activity of 100% at an application rate of 5 µg/cm$^2$ (=500 g/ha): I-1-4, I-1-6, I-1-7, I-1-31.

In this test, for example, the following compounds from the preparation examples showed good activity of 90% at an application rate of 5 µg/cm$^2$ (=500 g/ha): I-1-30.

*Boophilus microplus*—Injection Test

Solvent: dimethyl sulfoxide

To produce a suitable preparation of active compound, 10 mg of active compound are dissolved in 0.5 ml solvent, and the concentrate is diluted with solvent to the desired concentration.

Five adult engorged female ticks (*Boophilus microplus*) are injected with 1 µl compound solution into the abdomen. The ticks are transferred into replica plates and incubated in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 20 µg/animal: I-1-1, I-1-3, I-1-4, I-1-5, I-1-6, I-1-7, I-1-8, I-1-9, I-1-11, I-1-12, I-1-14, I-1-20, I-1-22, I-1-30, I-1-31, I-1-44, I-1-55, I-1-57.

*Ctenocephalides felis*—Oral Test

Solvent: dimethyl sulfoxide

To produce a suitable preparation of active compound, 10 mg of active compound are dissolved in 0.5 ml solvent, and the concentrate is diluted with cattle blood to the desired concentration.

Approximately 20 adult unfed cat fleas (*Ctenocephalides felis*) are placed in flea chambers. The blood chamber, sealed with parafilm on the bottom, are filled with cattle blood supplied with compound solution and placed on the gauze covered top of the flea chamber, so that the fleas are able to suck the blood. The blood chamber is heated to 37° C. whereas the flea chamber is kept at room temperature.

After 2 days mortality in % is determined. 100% means all the fleas have been killed; 0% means none of the fleas have been killed.

In this test, for example, the following compounds from the preparation examples showed good activity of 100% at an application rate of 100 ppm: I-1-6, I-1-14, I-1-20, I-1-30, I-1-31, I-1-44, I-1-55, I- 1-57.

In this test, for example, the following compounds from the preparation examples showed good activity of 98% at an application rate of 100 ppm: I-1-12.

In this test, for example, the following compounds from the preparation examples showed good activity of 95% at an application rate of 100 ppm: I-1-1.

In this test, for example, the following compounds from the preparation examples showed good activity of 90% at an application rate of 100 ppm: I-1-4, I-1-7, I-1-8.

In this test, for example, the following compounds from the preparation examples showed good activity of 70% at an application rate of 100 ppm: I-1-9, I-1-25, I-1-28.

*Lucilia cuprina*—Test
Solvent: dimethyl sulfoxide 10 mg active compound are dissolved in 0.5 ml Dimethylsulfoxid. Serial dilutions are made to obtain the desired rates.

Approximately 20 $1^{st}$ instar larvae of the Australian sheep blowfly (*Lucilia cuprina*) are transferred into a test tube containing minced horse meat and compound solution of the desired concentration.

After 2 days mortality in % is determined. 100% means all the larvae have been killed; 0% means none of the larvae have been killed.

In this test, for example, the following compounds from the preparation examples showed good activity of 100% at an application rate of 100 ppm: I-1-6, I-1-7, I-1-8, I-1-14, I-1-20, I-1-30, I-1-31, I-1-44, I-1-55, I-1-57.

In this test, for example, the following compounds from the preparation examples showed good activity of ≥70% and <100% at an application rate of 100 ppm: I-1-4, I-1-5, I-1-12, I-1-19.

*Musca domestica*—Test
Solvent: dimethyl sulfoxide

To produce a suitable preparation of active compound, 10 mg of active compound are dissolved in 0.5 ml solvent, and the concentrate is diluted with water to the desired concentration.

10 adult house flies (*Musca domestica*) are transferred into a container, containing a sponge soaked with a mixture of sugar solution and compound solution of the desired concentration.

After 2 days mortality in % is determined. 100% means all the flies have been killed; 0% means none of the flies have been killed.

In this test, for example, the following compounds from the preparation examples showed good activity of 100% at an application rate of 100 ppm: I-1-57.

In this test, for example, the following compounds from the preparation examples showed good activity of 80% at an application rate of 100 ppm: I-1-31.

*Haemonchus contortus*—Test
Solvent: dimethyl sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days the percentage of larval mortality is recorded. 100% efficacy means all larvae are killed, 0% efficacy means no larvae are killed.

In this test for example, the following compounds from the preparation examples showed good activity of 100% at an application rate of 20 ppm: I-1-2.

In this test for example, the following compounds from the preparation examples showed good activity of 80% at an application rate of 20 ppm: I-1-1, I-1-56.

*Diabrotica Balteata*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Soaked wheat seeds (*Triticum aestivum*) are placed in a multiple well plate filled with agar and some water and are incubated for 1 day to germinate (5 seeds per well). The germinated wheat seeds are sprayed with a test solution containing the desired concentration of the active ingredient. Afterwards each unit is infected with 10-20 larvae of the banded cucumber beetle (*Diabrotica balteata*).

After 7 days efficacy in % is determined. 100% means all the seedlings have grown up like in the untreated, uninfected control; 0% means none of the seedlings have grown.

In this test, for example, the following compounds from the preparation examples showed good activity of 100% at an application rate of 160 µg/well: I-1-7, I-1-19, I-1-20, I-1-44, I-1-55, I-1-57, I-1-64, I-1-70, I-1-73.

In this test, for example, the following compounds from the preparation examples showed good activity of 80% at an application rate of 160 µg/well: I-1-6, I-1-29, I-1-38, I-1-53, I-1-61, I-1-77.

*Meloidogyne incognita*—Test
Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined on the basis of the percentage of gall formation. 100% means no galls were found and 0% means the number of galls found on the roots of the treated plants was equal to that in untreated control plants.

In this test, for example, the following compounds from the preparation examples showed good activity of 100% at an application rate of 20 ppm: I-1-2, I-1-6, I-1-10, I-1-12, I-1-14, I-1-20, I-1-29, I-1-30, I-1-36.

In this test, for example, the following compounds from the preparation examples showed good activity of 90% at an application rate of 20 ppm: I-1-1, I-1-3, I-1-4, I-1-5, I-1-13, I-1-16, I-1-19, I-1-28, I-1-48.

In this test, for example, the following compounds from the preparation examples showed good activity of 70% at an application rate of 20 ppm: I-1-9, I-1-39.

*Myzus persicae*—Spray Test
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 5-6 days mortality in % is determined. 100% means all aphids have been killed and 0% means none of the aphids have been killed.

In this test, for example, the following compounds from the preparation examples showed good activity of ≥70% at an application rate of 500 g/ha: I-1-6, I-1-12, I-1-20, I-1-30, I-1-32, I-1-35, I-1-39, I-1-54, I-1-55, I-1-56, I-1-57, I-1-61, I-1-62, I-1-64, I-2-1, I-2-3, I-3-2.

*Nezara viridula*—Spray Test

Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Barley plants (*Hordeum vulgare*) infested with larvae of the southern green stink bug (*Nezara viridula*) are sprayed with a test solution containing the desired concentration of the active ingredient.

After 4 days mortality in % is determined. 100% means all the stink bugs have been killed; 0% means none of the stink bugs have been killed.

In this test, for example, the following compounds from the preparation examples showed good activity of ≥90 at an application rate of 500 g/ha: I-1-18, I-1-20, I-1-21, I-1-22, I-1-23, I-1-25, I-1-26, I-1-29, I-1-33, I-1-35, I-1-37, I-1-42, I-1-43, I-1-44, I-1-50, I-1-51, I-1-55, I-1-56, I-1-57, I-1-58, I-1-59, I-1-60, I-1-61, I-1-62, I-1-63, I-1-64, I-1-69, I-1-76.

*Nilaparvata lugens*—Spray Test

Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Rice plants (*Oryza sativa*) are sprayed with a preparation of the active ingredient of the desired concentration and the plants are infested with the brown planthopper (*Nilaparvata lugens*).

After 4 days mortality in % is determined. 100% means all planthoppers have been killed and 0% means none of the planthoppers have been killed.

In this test, for example, the following compounds from the preparation examples showed good activity of ≥70% at an application rate of 500 g/ha: I-1-20, I-1-42, I-1-50, I-1-51, I-1-61, I-1-75.

*Phaedon cochleariae*—Spray Test

Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks are sprayed with a preparation of the active ingredient of the desired concentration. Once dry, the leaf disks are infested with mustard beetle larvae (*Phaedon cochleariae*).

After 7 days mortality in % is determined. 100% means all beetle larvae have been killed and 0% means none of the beetle larvae have been killed.

In this test, for example, the following compounds from the preparation examples showed good activity of ≥80 at an application rate of 500 g/ha: I-1-1, I-1-2, I-1-3, I-1-4, I-1-5, I-1-6, I-1-7, I-1-8, I-1-9, I-1-10, I-1-11, I-1-12, I-1-13, I-1-14, I-1-18, I-1-19, I-1-20, I-1-21, I-1-22, I-1-23, I-1-24, I-1-25, I-1-26, I-1-27, I-1-28, I-1-30, I-1-31, I-1-32, I-1-35, I-1-36, I-1-37, I-1-38, I-1-39, I-1-40, I-1-41, I-1-43, I-1-44, I-1-46, I-1-47, I-1-48, I-1-50, I-1-52, I-1-53, I-1-54, I-1-55, I-1-56, I-1-57, I-1-58, I-1-59, I-1-60, I-1-61, I-1-62, I-1-64, I-1-68, I-1-69, I-1-70, I-1-71, I-1-72, I-1-73, I-1-76, I-1-78, I-2-1, I-2-2, I-2-3, I-2-4, I-2-5, I-2-6, I-3-1, I-3-2.

*Spodontera frugiperda*—Spray Test

Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means all caterpillars have been killed and 0% means none of the caterpillars have been killed.

In this test, for example, the following compounds from the preparation examples showed good activity of ≥80% at an application rate of 500 g/ha: I-1-27, I-1-28, I-1-55, I-1-57, I-1-61, I-1-62, I-1-64, I-1-69, I-1-76.

*Tetranychus urticae*—Spray Test OP-Resistant

Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

French bean (*Phaseolus vulgaris*) leaf disks infected with all instars of the two spotted spidermite (*Tetranychus urticae*), are sprayed with a preparation of the active ingredient of the desired concentration.

After 6 days mortality in % is determined. 100% means all spider mites have been killed and 0% means none of the spider mites have been killed.

In this test, for example, the following compounds from the preparation examples showed good activity of ≥70% at an application rate of 500 g/ha:

I-1-1, I-1-3, I-1-4, I-1-5, I-1-6, I-1-8, I-1-15, I-1-16, I-1-17, I-1-19, I-1-20, I-1-30, I-1-31, I-1-32, I-1-34, I-1-43, I-1-49, I-1-51, I-1-55, I-1-56, I-1-57, I-1-59, I-1-60, I-1-61, I-1-62, I-1-64, I-1-69, I-1-74, I-1-76, I-2-1, I-2-6.

*Plutella xylostella*—Spray Test

Solvent: 14 parts by weight of dimethylformamide

Emulsifier: alkylaryl polyglycol ether

To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water.

Cabbage leaves (*Brassica oleracea*) are treated by being sprayed with the preparation of the active compound of the desired concentration and are infested with larvae of the diamondback moth (*Plutella xylostella*).

After 7 days, mortality in % is determined. 100% means all the caterpillars have been killed and 0% means none of the caterpillars have been killed.

In this test, for example, the following compounds from the preparation examples showed good activity of 100% at an application rate of 100 ppm: I-1-10, I-1-11, I-1-12.

*Nezara viridula*—Spray Test

Solvent: 52.5 parts by weight of acetone 7 parts by weight of dimethylformamide

Emulsifier: alkylaryl polyglycolether

To produce a suitable preparation of active compound, 1 part by weight of active compound is mixed with the stated amount of solvent, and the concentrate is diluted with water, containing an emulsifier concentration of 1000 ppm, to the desired concentration. Ammonium salt and/or penetration enhancer in a dosage of 1000 ppm are added to the desired concentration if necessary.

Barley plants (*Hordeum vulgare*) infested with larvae of the southern green stink bug (*Nezara viridula*) are sprayed with a test solution containing the desired concentration of the active ingredient.

After 4 days mortality in % is determined. 100% means all the stink bugs have been killed; 0% means none of the stink bugs have been killed.

In this test, for example, the following compounds from the preparation examples showed good activity of of ≥90% at an application rate of 500 g/ha: I-1-1, I-1-3, I-1-4, I-1-6, I-1-7, I-1-8, I-1-10, I-1-11, I-1-12, I-1-14, I-1-15, I-1-20, I-1-25, I-1-27, I-1-29, I-1-30, I-1-31, I-1-35, I-1-42, I-1-43, I-1-44, I-1-50, I-1-51, I-1-55, I-1-56, I-1-57, I-1-58, I-1-59, I-1-60, I-1-61, I-1-62, I-1-64, I-1-65, I-1-66, I-1-67, I-1-69, I-1-73, I-2-5, I-3-1, I-3-2, I-3-3, I-3-4.

*Nilaparvata lugens*—Spray Test

Solvent: 52.5 parts by weight of acetone 7 parts by weight of dimethylformamide

Emulsifier: alkylaryl polyglycolether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water. Ammonium salt and/or penetration enhancer in a dosage of 1000 ppm are added to the desired concentration if necessary.

Rice plants (*Oryza sativa*) are treated by being sprayed with the desired concentration of the active compound and are infested with larvae of the brown planthopper (*Nilaparvata lugens*).

After 4 days mortality in % is determined. 100% means all planthoppers have been killed and 0% means none of the planthoppers have been killed.

In this test, for example, the following compounds from the preparation examples showed good activity of ≥80% at an application rate of 500 g/ha: I-1-6, I-1-20, I-1-30, I-1-42, I-1-59, I-1-61, I-1-62, I-1-65, I-2-6, I-3-5.

*Euschistus heros*—Test

Solvent: 7 parts by weight of dimethylformamide

Emulsifier: alkylaryl polyglycolether

To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water. Ammonium salt and/or penetration enhancer (rapeseed oil methyl esters) in a dosage of 1000 ppm are added to the desired concentration if necessary.

Kidney bean plants (*Phaseolus vulgaris*) are treated by being sprayed with the preparation of the active compound of the desired concentration and are infested with 10 larvae per plant of the brown stink bug (*Euschistus heros*).

After 7 days feeding control in % is determined. 100% means there is no feeding damage visible and 0% means the plant damage corresponds to that of the untreated control plants.

In this test, for example, the following compounds from the preparation examples showed good activity of ≥75% at an application rate of 100 ppm: I-1-4, I-1-6, I-1-7, I-1-14, I-1-20.

*Nezara viridula*—Test

Solvent: 7 parts by weight of dimethylformamide

Emulsifier: alkylaryl polyglycolether

To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water. Ammonium salt and/or penetration enhancer (rapeseed oil methyl esters) in a dosage of 1000 ppm are added to the desired concentration if necessary.

Cotton plants (*Gossypium hirsutum*) are treated by being sprayed with the preparation of the active compound of the desired concentration and are infested with 10 larvae per plant of the green plant bug (*Nezara viridula*).

After 2 days feeding control in % is determined. 100% means there is no feeding damage visible and 0% means the plant damage corresponds to that of the untreated control plants.

In this test, for example, the following compounds from the preparation examples showed good activity of ≥70% at an application rate of 100 ppm: I-1-4, I-1-6, I-1-7, I-1-14, I-1-20, I-1-43.

The invention claimed is:

1. A compound of formula (I-1)

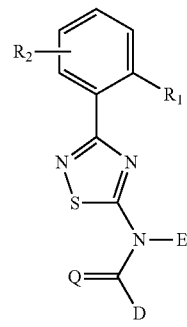

in which

D represents a radical selected from the group consisting of

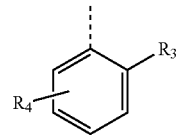
B-1

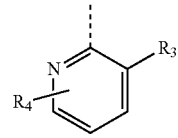
B-2

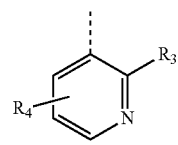
B-3

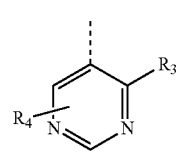
B-7

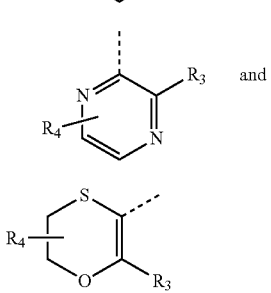
B-8 and

B-12 in which the broken line represents the bond to the carbon atom in C=Q,

E represents hydrogen, a Li-, Na-, K-, Mg-, Ca-ion, or an ammonium ion of formula

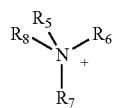

wherein $R_5$, $R_6$, $R_7$ and $R_8$ independently represent hydrogen, methyl, ethyl or benzyl, Q represents oxygen, $R_1$ represents fluorine, chlorine, bromine, iodine, cyano, nitro, methyl, ethyl, difluoromethyl, trifluoromethyl, chloro-difluoromethyl, pentafluoroethyl, cyclopropyl, methoxy, ethoxy,-difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, or trifluoroethylsulphonyl, $R_2$ represents hydrogen, fluorine, chlorine, bromine, iodine, cyano, nitro, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, or trifluoroethylsulphonyl, $R_3$ represents fluorine, chlorine, bromine, iodine, cyano, nitro, methyl, ethyl, difluoromethyl, trifluoromethyl, chloro-difluoromethyl, pentafluoroethyl, cyclopropyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, methylsulphinyl, ethylsulphinyl, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, or trifluoroethylsulphonyl, and $R_4$ represents hydrogen, fluorine, chlorine, bromine, iodine, nitro, cyano, methyl, ethyl, difluoromethyl, trifluoromethyl, chloro-difluoromethyl, pentafluoroethyl, methoxy, ethoxy, difluoromethoxy, trifluoromethoxy, chloro-difluoro-methoxy, difluoroethoxy, trifluoroethoxy, methylthio, ethylthio, trifluoromethylthio, difluoromethylthio, difluoroethylthio, trifluoroethylthio, trifluoromethylsulphinyl, difluoromethylsulphinyl, difluoroethylsulphinyl, trifluoroethylsulphinyl, methylsulphonyl, ethylsulphonyl, trifluoromethylsulphonyl, difluoromethylsulphonyl, difluoroethylsulphonyl, or trifluoroethylsulphonyl.

2. A composition comprising at least one compound according to claim 1 and one or more extenders and/or surfactants.

3. A method for controlling one or more pests, comprising allowing a compound of the formula (I) according to claim 1 to act on the pests and/or a habitat thereof, provided that methods for the therapeutic treatment of an animal body are excluded.

4. A method for controlling one or more arthropodal parasites on animals, comprising allowing a compound of the formula (I) according to claim 1 to act on the parasites and/or a habitat thereof.

5. A compound according to claim 1, wherein $R_1$ is chlorine, fluorine, difluoromethyl, or trifluoromethyl.

6. A compound according to claim 1, wherein D is B-1.

7. A compound according to claim 1, wherein D is B-2.

8. A compound according to claim 1, wherein D is B-3.

9. A compound according to claim 1, wherein D is B-7.

10. A compound according to claim 1, wherein D is B-8.

11. A compound according to claim 1, wherein D is B-12.

12. A compound according to claim 5, wherein D is B-3.

13. A compound according to claim 1, wherein $R_3$ is chlorine, fluorine, difluoromethyl, or trifluoromethyl.

14. A compound according to claim 12, wherein $R_3$ is chlorine, fluorine, difluoromethyl, or trifluoromethyl.

15. A compound according to claim 14, wherein $R_4$ is hydrogen.

16. A compound according to claim 1, of the structure

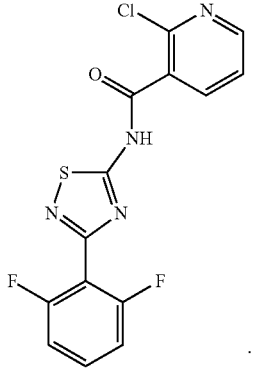 [SMILES: O=C(Nc1nc(-c2c(F)cccc2F)ns1)c1cccnc1Cl]

17. A compound according to claim 1 of the structure

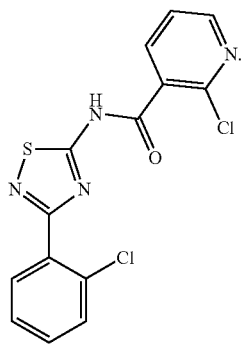 [SMILES: O=C(Nc1nc(-c2ccccc2Cl)ns1)c1cccnc1Cl]

18. A compound according to claim 1 of the structure

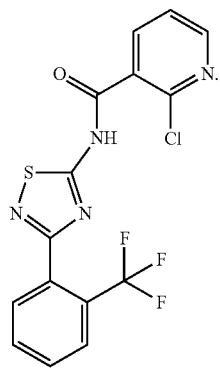 [SMILES: O=C(Nc1nc(-c2ccccc2C(F)(F)F)ns1)c1cccnc1Cl]

19. A compound according to claim 1 of the structure

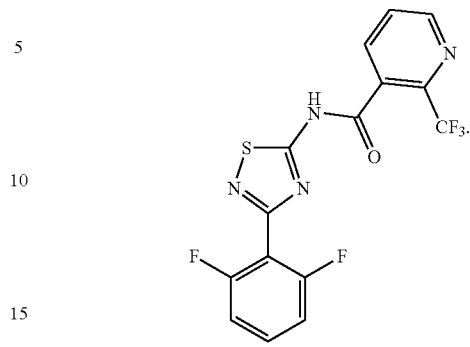

20. A compound according to claim 1, which is N-[3-(2,6-difluorophenyl)-1,2,4-thiadiazol-5-yl]-2-(trifluoromethyl)benzamide.

21. A compound according to claim 1, which is N-[3-(2,6-difluorophenyl)-1,2,4-thiadiazol-5-yl]-3-(trifluoromethyl)pyrazine-2-carboxamide.

22. A compound according to claim 1, which is 2-(difluoromethyl)-N-[3-(2,6-difluorophenyl)-1,2,4-thiadiazol-5-yl]nicotinamide.

23. A compound according to claim 1, which is 2-(trifluoromethyl)-N-{3-[2-(trifluoromethyl)phenyl]-1,2,4-thiadiazol-5-yl}nicotinamide.

24. A compound according to claim 1, which is 2-chloro-N-[3-(2,6-difluorophenyl)-1,2,4-thiadiazol-5-yl]nicotinamide.

25. A compound according to claim 1, which is sodium 3-(2,6-difluorophenyl)-N-{[2-(trifluoromethyl)pyridin-3-yl]carbonyl}-1,2,4-thiadiazol-5-aminide.

26. A compound according to claim 1, which is N-[3-(2-chlorophenyl)-1,2,4-thiadiazol-5-yl]-2-(trifluoromethyl)nicotinamide.

27. A compound according to claim 1, which is N-{3-[2-(trifluoromethoxy)phenyl]-1,2,4-thiadiazol-5-yl}-2-(trifluoromethyl)nicotinamide.

28. A compound according to claim 1, which is N-{3-[4-fluoro-2-(trifluoromethyl)phenyl]-1,2,4-thiadiazol-5-yl}-2-(trifluoromethyl)nicotinamide.

29. A compound according to claim 1, which is N-{3-[3-fluoro-2-(trifluoromethyl)phenyl]-1,2,4-thiadiazol-5-yl}-2-(trifluoromethyl)nicotinamide.

30. A compound according to claim 1, which is N-{3-[2-chloro-3-(trifluoromethyl)phenyl]-1,2,4-thiadiazol-5-yl}-2-(trifluoromethyl)nicotinamide.

31. A compound according to claim 1, which is N-{3-[5-fluoro-2-(trifluoromethyl)phenyl]-1,2,4-thiadiazol-5-yl}-2-(trifluoromethyl)nicotinamide.

* * * * *